(12) United States Patent
Filla et al.

(10) Patent No.: US 7,230,011 B2
(45) Date of Patent: Jun. 12, 2007

(54) BENZENESULFONIC ACID INDOL-5-YL ESTERS AS ANTAGONISTS OF THE 5HT$_6$ RECEPTOR

(75) Inventors: Sandra Ann Filla, Franklin, IN (US); Michael Edward Flaugh, Indianapolis, IN (US); James Ronald Gillig, Indianapolis, IN (US); Lawrence Joseph Heinz, Pittsboro, IN (US); Joseph Herman Krushinski, Jr., Brownsburg, IN (US); Bin Liu, Fishers, IN (US); Marta Maria Pineiro-Nunez, Brownsburg, IN (US); John Mehnert Schaus, Zionsville, IN (US); John Stanley Ward, Redwood City, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/466,969

(22) PCT Filed: Jan. 17, 2002

(86) PCT No.: PCT/US02/00502

§ 371 (c)(1),
(2), (4) Date: Jul. 22, 2003

(87) PCT Pub. No.: WO02/060871

PCT Pub. Date: Aug. 8, 2002

(65) Prior Publication Data

US 2004/0102481 A1 May 27, 2004

(51) Int. Cl.
*A61K 31/454* (2006.01)
*A61K 31/4545* (2006.01)
*C07D 401/04* (2006.01)
*C07D 401/14* (2006.01)

(52) U.S. Cl. ............... 514/323; 514/318; 514/339; 546/194; 546/201; 546/277.4

(58) Field of Classification Search ............... 546/201, 546/277.4, 194; 514/323, 339, 318
See application file for complete search history.

(56) References Cited

U.S. PATENT DOCUMENTS

| | | |
|---|---|---|
| 5,521,196 A | 5/1996 | Audia et al. |
| 5,521,197 A | 5/1996 | Audia |
| 5,708,008 A | 1/1998 | Audia et al. |
| 5,792,763 A | 8/1998 | Fritz et al. |
| 5,942,536 A | 8/1999 | Fritz et al. |
| 6,133,287 A | 10/2000 | Slassi et al. |

FOREIGN PATENT DOCUMENTS

| WO | WO 00/63203 | 10/2000 |
|---|---|---|
| WO | WO 01/09088 | 2/2001 |

OTHER PUBLICATIONS

Franz et al., "5-HT6 receptor antagonism potentiates, etc.," Neuropharmacology 42 (2002) 170-180.*
Glennon et al., "2-Substituted Tryptamines, etc.," J. Med. Chem. 2000, 43, 1011-1018.*
Rogers et al., "5-HT6 receptor antagonists enhance, etc.," Psychopharmacology (2001) 158: 114-119.*
Branchek et al., "5-HT6 receptors as emerging, etc.," Annu. Rev. Pharmacol. Toxicol. 2000, 40: 319-34.*
Barnes et al., "A review of central 5-HT, etc.,"Neuropharmacology, 38 (1999) 1083-1152.*
Stephen L. Gwaltney, II, et al., "Novel sulfonate Analogues of Combretastatin A-4: Potent Antimitotic Agents," *Bioorganic & Medicinal Chemistry Letters*, vol. 11, pp. 871-874 (2001).
Gwaltney et al., "Novel Sulfonate Analogues of Combretastatin A-4: Potent Antimitotic Agents," *Bioorganic & Medicinal Chemistry Letters*, vol. 11, pp. 871-874 (2001).
Bos et al., "5-HT6 receptor antagonists: lead optimization and biological evaluation of N-aryl and N-heteroaryl 4-amino-benzene sulfonamides," *Eur. J. Med. Chem.*, vol. 36, pp. 165-178 (2001).
Bourson et al., "Determination of the Role of the 5-HT6 Receptor in the Rat Brain: A Study using Antisense Iligonucleotides," *J. Pharm. And Experimental Therapeutics*, vol. 274, No. 1, pp. 173-180(1995).
Branchek et al., "5-HT6 Receptors as Emerging Targets for Drug Discovery," *Annual Rev. of Pharmacology and Toxicology*, vol. 40 pp. 319-334 (2000).
Dawson et al., et al., "In Vivo Effects of the 5-HT6 Antagonist SB-271046 on Striatal and Frontal Cortex Extracellular Concentrations of Noradrenaline, Dopamine, 5-HT, Glutamate and Aspartate," *British J. of Pharmacology*, vol. 130, pp. 23-26 (2000).
Meneses, Alfredo, "Effects of the 5-HT6 receptor antagonist Ro 04-6790 on learning consolidation," *Behavioral Brain Research*, vol. 118, pp. 107-110 (2001).

(Continued)

Primary Examiner—Patricia L. Morris
(74) *Attorney, Agent, or Firm*—Tonya L. Combs; Elizabeth A. McGraw; Manisha A. Desai

(57) ABSTRACT

The present invention relates to compounds of formula I: which are antagonists of 5-HT6 receptor.

(I)

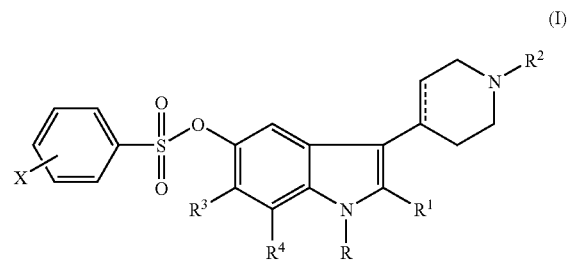

11 Claims, No Drawings

OTHER PUBLICATIONS

Ohmori et al., "Novel Polymorphism in the 5'-upstream Region of the Human 5-HT6 Receptor Gene and Schizophrenia," *Neuroscience Let.*, vol. 310, pp. 17-20 (2001).

Rogers et al., "5-HT6 receptor antagonists enhance retention of a water maze task in the rat," *Psyhopharmacology*, vol. 158, pp. 114-119 (2001).

Tsai et al., "$N_1$-(Benzenesulfonyl)tryptamines as Novel 5-$HT_6$ Antagonists," *Bioorganic & Med. Chem. Let.*, vol. 10, pp. 2295-2299 (2000).

Yoshioka et al.,"Central Distribution and Function of 5-HT6 Receptor Subtype in the Rat Brain," *Life Sciences*, vol. 62, Nos. 17/18, pp. 1473-1477 (1998).

* cited by examiner

BENZENESULFONIC ACID INDOL-5-YL ESTERS AS ANTAGONISTS OF THE 5HT$_6$ RECEPTOR

The present invention relates to the field of pharmaceutical and organic chemistry and is concerned with compounds which are antagonists of the 5-HT$_6$ receptor.

The 5-HT$_6$ receptor is a member of the G-protein coupled receptor superfamily of serotonin receptors, and, like the 5-HT$_4$ and 5-HT$_7$ receptors, it is positively coupled to adenylate cyclase.[1] The rat 5-HT$_6$ receptor was first cloned in 1993[2,3] and the cloning of the human homologue, to which it shares a 89% sequence identity, was reported in 1996.[4] The localization of 5-HT$_6$ receptors in rat brain has been studied using mRNA quantification by Northern analysis and RT-PCR, immunohistochemistry, and autoradiography.[2,3,5,6,7,8] These methods have consistently found high levels of the receptor in olfactory tubercle, hippocampus, striatum, nucleus accumbens, and cortical regions. 5-HT$_6$ receptors are either absent or present in very low levels in peripheral tissues.[2,3]

To date, there are no known high affinity, selective agonists at the 5-HT$_6$ receptor. Serotonin itself has only moderate affinity for the 5-HT$_6$ receptor (Ki=65 nM) and the most selective agonist reported to date, N,N-dimethyl-2-ethyl-5-methoxytryptamine, has Ki=81 nM and only 3.5-fold selectivity versus the 5-HT$_{2A}$ receptor.[9]

Much of the recent interest in the 5-HT$_6$ receptor is due to the observation that several psychotropic agents are high affinity antagonists at the human 5-HT$_6$ receptor.[4,10] These compounds include amitriptyline (Ki=65 nM) and the atypical antipsychotics clozapine (Ki=9.5 nM), olanzapine (Ki=10 nM), and quetiapine (33 nM). None of these compounds, however, are selective. The first selective 5-HT$_6$ receptor antagonists reported are Ro 04-6790 and Ro 63-0563. Their usefulness is limited by their moderate affinity (Ki=50 nM and 12 nM, respectively) and poor pharmacokinetics.[11] A series of 5-HT$_6$ receptor antagonists, culminating in SB-271,046, has been reported.[12] This compound has high affinity (Ki=1.2 nM) and selectivity (>200-fold versus >55 receptors, enzymes and ion channels) and is 80% bioavailable. A selective radioligand [$^{125}$I]-SB-258,585 has been used for radioligand binding and autoradiographic studies.[13,14] These compounds are useful tools for preclinical studies on the 5-HT$_6$ receptor. No clinical studies with any selective 5-HT$_6$ receptor antagonists have been reported.

The rationale for the use of selective 5-HT$_6$ receptor antagonists to treat cognitive dysfunction is based on three lines of reasoning: the ability of selective 5-HT$_6$ receptor antagonists to modulate cholinergic and glutamatergic neuronal function, clinical studies of the atypical antipsychotics clozapine and olanzapine on cognitive function, the activity of selective 5-HT$_6$ receptor antagonists in animal models of cognitive function.

Selective 5-HT$_6$ receptor antagonists modulate cholinergic and glutamatergic neuronal function. Cholinergic and glutamatergic neuronal systems play important roles in cognitive function. Cholinergic neuronal pathways are known to be important to memory formation and consolidation. Centrally acting anticholinergic agents impair cognitive function in animal and clinical studies and loss of cholinergic neurons is one of the hallmarks of Alzheimer's disease. Conversely, stimulation of cholinergic function has been known to improve cognitive performance and the only two agents currently approved for the treatment of cognitive deficit in Alzheimer's disease, tacrine and donepezil, are both acetylcholinesterase inhibitors. The glutamatergic system in the prefrontal cortex is also known to be involved in cognitive function.[26,27]

Blocking 5-HT$_6$ receptor function has been shown to elicit procholinergic effects in vivo. Administration (icv) to rats of antisense oligonucleotides targeting the 5-HT$_6$ receptor sequence induced yawning and stretching behavior that was blocked by the cholinergic antagonist atropine.[15] The selective 5-HT$_6$ receptor antagonist Ro 04-6790 induced stretching behavior in a dose-dependent manner. This behavior was blocked by the centrally acting anticholinergic agents scopolamine and atropine but not by methyl-scopolamine at doses known to be peripherally selective.[16] Ro 04-6790 was also shown to block the rotation behavior induced by scopolamine administration to rats with unilateral nigrostriatal 6-OH-DA lesions. It did not block rotational behavior induced by L-DOPA or amphetamine.[17] Ro 04-6790 reversed scopolamine induced performance deficits in the object recognition test, a model of cognitive function. Another selective 5-HT$_6$ receptor antagonist, SB-271046, potentiated the yawning behavior induced by the cholinesterase inhibitor physostigmine.[18] These studies suggest that 5-HT$_6$ receptor blockade facilitates cholinergic transmission. In vivo microdialysis studies, SB-271,046 (10 mg/kg, sc) increases glutamate release in the prefrontal cortex through a neuronal mechanism.[25]

Clinical studies of the atypical antipsychotics clozapine and olanzapine on cognitive function. The atypical antipsychotics clozapine and olanzapine are both high affinity, albeit nonselective, 5-HT$_6$ receptor antagonists.[4] On the other hand, risperidone and the typical antipsychotic haloperidol do not have significant affinity for the 5-HT$_6$ receptor. Clinical differences seen with these sets of drugs may be attributable to 5-HT$_6$ receptor blockade. Goldberg et al. reported no beneficial cognitive effect of clozapine treatment in a small (N=15) trial in treatment resistant schizophrenics.[19] In contrast, Meltzer et al [20] in a larger study of treatment-resistant schizophrenics (N=36), observed improvements in several domains of neuropsychological function at six weeks and six months following initiation of clozapine treatment. In non-treatment resistant schizophrenics, clozapine was more effective than placebo in improving cognitive function by several measures.[21] This effect was seen at six months and persisted throughout the 12 month study. The effect of olanzapine, risperidone, and haloperidol on cognitive function has been compared in a multicenter, double blind study in schizophrenics.[22] The olanzapine group showed a statistically significant improvement in cognitive function over either haloperidol or risperidone treatment. This effect was apparent after 6 weeks treatment and continued throughout the 54 weeks of the study. Animal studies suggest that these effects could be mediated through the release of acetylcholine in the prefrontal cortex.[23]

Activity of selective 5-HT$_6$ receptor antagonists in animal models of cognitive function. With the recent development of the selective 5-HT$_6$ receptor antagonists Ro-04,6790 and SB-271,046, there have been several reports on the activity of these compounds in models of cognitive function. The selective 5-HT$_6$ receptor antagonist SB-271,046 improved performance in the Morris water maze.[24] These results are consistent with the finding that chronic icv administration of antisense oligonucleotides directed toward the 5-HT$_6$ receptor sequence led to improvements in some measures of performance in the Morris water maze.[16] SB-271,046 treatment also led to improvements in the spatial alternation operant behavior test in aged rats.[24]

The compounds of the present invention are selective, high affinity antagonists of 5-HT$_6$, and thus, provide a valuable treatment for 5-HT$_6$ receptor mediated disorders.

BACKGROUND REFERENCES

1. Branchek, T. A., et al. (2000). Annu Rev Pharmacol Toxicol 40: 319-34.
2. Monsma, F. J., Jr., et al. (1993). Mol Pharmacol 43(3): 320-7.
3. Ruat, M., et al. (1993). Biochem Biophys Res Commun 193(1): 268-76.
4. Kohen, R., et al. (1996). J Neurochem 66(1): 47-56.
5. Ward, R. P., et al. (1996). J Comp Neurol 370(3): 405-14.
6. Ward, R. P., et al. (1995). Neuroscience 64(4): 1105-11.
7. Gerard, C., et al. (1997). Brain Res 746(1-2): 207-19.
8. Gerard, C., et al. (1996). Synapse 23(3): 164-73.
9. Glennon, R. A., et al. (2000). J Med Chem 43(5): 1011-8.
10. Roth, B. L., et al. (1994). J Pharmacol Exp Ther 268(3): 1403-10.
11. Sleight, A. J., et al. (1998). Br J Pharmacol 124(3): 556-62.
12. Routledge, C., et al. (2000). Br. J. Pharmacol. 130(7): 1606.
13. Hirst, W. D., et al. (1999). Br. J. Pharmacol. Suppl.((in press)).
14. Hirst, W. D., et al. (2000). Br. J. Pharmacol. 130: 1597.
15. Bourson, A., et al. (1995). J Pharmacol Exp Ther 274(1): 173-80.
16. Bentley, J. C., et al. (1999). Br J Pharmacol 126(7): 1537-42.
17. Bourson, A., et al. (1998). Br J Pharmacol 125(7): 1562-6.
18. Routledge, C., et al. (1999). Br. J. Pharmacol. 127 (Suppl.): 21P.
19. Goldberg, T. E., et al. (1993,). Br J Psychiatry 162: 43-8.
20. Hagger, C., et al. (1993). Biol Psychiatry 34(10): 702-12.
21. Lee, M. A., et al. (1994). J Clin Psychiatry 55 Suppl B: 82-7.
22. Purdon, S. E., et al. (2000). Arch Gen Psychiatry 57(3): 249-58.
23. Parada, M. A., et al. (1997). J Pharmacol Exp Ther 281(1): 582-8.
24. Rogers, D. C., et al. (1999). Br J Pharamcol 127(suppl.): 22P.
25. Dawson, L. A., et al. (2000). Br J Pharmacol 130(1): 23-6.
26. Dudkin, K. N., et al. (1996). Neurosci Behav Physiol 26(6): 545-51.
27. Koechlin, E., et al. (1999). Nature 399(6732): 148-51.

The present invention provides compounds of formula I:

formula I

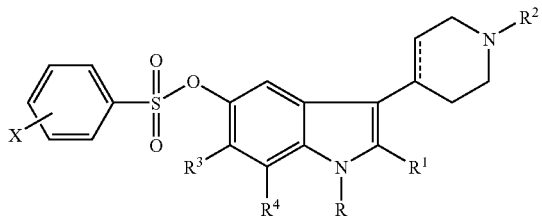

wherein

R is hydrogen, $C_1$-$C_6$ alkyl, substituted $C_1$-$C_6$ alkyl, $C_3$-$C_6$ cycloalkyl, $C_1$-$C_6$ alkylsulfonyl, phenylsulfonyl, substituted phenylsulfonyl, naphthylsulfonyl, benzylsulfonyl, or substituted benzylsulfonyl;

$R^1$ is hydrogen or $C_1$-$C_3$ alkyl or where $R^4$ is hydrogen, $C_1$-$C_6$ alkyl, or halo then $R^1$ and R may be taken together to form —$CH_2$—$CH_2$—$CH_2$— or —$CH_2$—$CH_2$—$CH_2$—$CH_2$—;

$R^2$ is hydrogen or $C_1$-$C_6$ alkyl;

$R^3$ is hydrogen or halo;

$R^4$ is hydrogen, $C_1$-$C_6$ alkyl, vinyl, allyl, $C_2$-$C_6$ alkynyl, or halo or when $R^1$ is hydrogen or $C_1$-$C_3$ alkyl then $R^4$ and R may be taken together to form —$CH_2$—$CH_2$—$CH_2$—;

X is 1 to 3 substituents independently selected from the group consisting of hydrogen, halo, $C_1$-$C_6$ alkyl, $C_1$-$C_6$ alkoxy, nitro, amino, $C_1$-$C_6$ alkylsulfonylamino, and cyano or X is 5 halo substituents;

⁞ represents either a single or a double bond; and pharmaceutically acceptable addition salts thereof.

The present invention also provides for novel pharmaceutical compositions, comprising: a compound of the formula I and a pharmaceutically acceptable diluent.

Because the compounds of formula I are antagonists of 5-HT$_6$ receptor, the compounds of formula I are useful for the treatment of a variety of disorders, including: cognitive disorders, age-related cognitive disorder, mild cognitive impairment, mood disorders (including depression, mania, bipolar disorders), psychosis (in particular schizophrenia), anxiety (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, and hypoglycemic neuronal damage, vascular dementia, multi-infarct dementia, amylotrophic lateral sclerosis, and multiple sclerosis, comprising: administering to a patient in need thereof an effective amount of a compound of formula I.

In another embodiment the present invention provides methods of treating disorders associated with the 5-HT$_6$ receptor, comprising: administering to a patient in need thereof an effective amount of a compound of formula I. That is, the present invention provides for the use of a compound of formula I or pharmaceutical composition thereof for the treatment disorders associated with the 5-HT$_6$ receptor.

DETAILED DESCRIPTION OF THE INVENTION

As used herein, the following terms have the meanings indicated:

The term "$C_1$-$C_3$ alkyl" straight or branched alkyl chain having from one to three carbon atoms, and includes methyl, ethyl, propyl, and iso-propyl.

The term "$C_1$-$C_6$ alkyl" refers to a straight or branched alkyl chain having from one to six carbon atoms, and includes methyl, ethyl, propyl, iso-propyl, butyl, iso-butyl, sec-butyl, t-butyl, pentyl, hexyl, and the like.

The term "substituted $C_1$-$C_6$ alkyl" refers to a straight or branched alkyl chain having from one to six carbon atoms and having 1 or 2 substituents selected from the group consisting of $C_3$-$C_6$ cycloalkyl, phenyl, substituted phenyl, pyridyl, and trifluoromethyl.

The term "$C_1$-$C_6$ alkoxy" refers to a straight or branched alkyl chain having from one to six carbon atoms attached through an oxygen atom, and includes methoxy, ethoxy, propoxy, iso-propoxy, butoxy, iso-butoxy, sec-butoxy, t-butoxy, pentoxy, hexoxy, and the like.

The term "$C_3$-$C_6$ cycloalkyl" refers to refers to saturated cyclic alkyl group having from three to six carbon atoms and includes, cyclopropyl, cyclobutyl, cyclopentyl, and cyclohexyl.

The term "$C_1$-$C_6$ alkylsulfonyl" refers to a radical of the formula

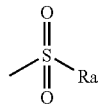

wherein $R_a$ is a $C_1$-$C_6$ alkyl.

The term "$C_1$-$C_6$ alkylsulfonylamino" refers to a radical of the formula

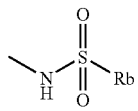

wherein $R_b$ is a $C_1$-$C_6$ alkyl.

The term "$C_3$-$C_6$ cycloalkyl" refers to a saturated cyclic alkyl group having from three to six carbon atoms and includes, cyclopropyl, cyclobutyl, cyclopentyl, and cyclohexyl.

The term "substituted phenylsulfonyl" refers to a radical of the formula

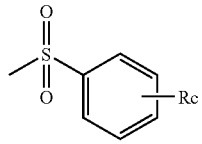

wherein $R_c$ is from 1 to 3 groups independently selected from the group consisting of hydrogen, $C_1$-$C_6$ alkyl, $C_1$-$C_6$ alkoxy, halogen, cyano, trifluoromethyl, nitro, and phenyl.

The term "substituted benzylsulfonyl" refers to a radical of the formula

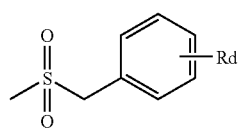

wherein $R_d$ is from 1 to 3 groups independently selected from the group consisting of hydrogen, $C_1$-$C_6$ alkyl, $C_1$-$C_6$ alkoxy, halogen, cyano, trifluoromethyl, and nitro.

The term "substituted phenyl" refers to a radical of the formula

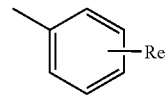

wherein $R_e$ is from 1 to 3 groups independently selected from the group consisting of hydrogen, $C_1$-$C_6$ alkyl, $C_1$-$C_6$ alkoxy, halogen, cyano, trifluoromethyl, nitro, and phenyl.

The term "$C_2$-$C_6$ alkynyl" refers to a radical of the formula

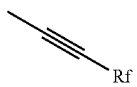

wherein $R_f$ is selected from the group consisting of hydrogen and $C_1$-$C_4$ alkyl.

The term "$C_1$-$C_4$ alkyl" refers to a straight or branched alkyl chain having from one to four carbon atoms, and includes methyl, ethyl, propyl, iso-propyl, butyl, iso-butyl, sec-butyl, and t-butyl.

The terms "halogen" and "halo" refer to a chloro, fluoro, bromo or iodo atom.

The term "pharmaceutically-acceptable addition salt" refers to an acid addition salt.

The compound of formula I and the intermediates described herein form pharmaceutically acceptable acid addition salts with a wide variety of organic and inorganic acids and include the physiologically acceptable salts which are often used in pharmaceutical chemistry. Such salts are also part of this invention. A pharmaceutically-acceptable addition salt is formed from a pharmaceutically-acceptable acid as is well known in the art. Such salts include the pharmaceutically acceptable salts listed in *Journal of Pharmaceutical Science*, 66, 2-19 (1977) which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

As with any group of pharmaceutically active compounds, some groups are preferred in their end use application. Preferred embodiments of the present invention are given below:

Compounds in which R is hydrogen or $C_1$-$C_6$ alkyl, R and $R^1$ are taken together to form —$CH_2$—$CH_2$—$CH_2$— or —$CH_2$—$CH_2$—$CH_2$—$CH_2$—, or R and $R^4$ are taken together to form —$CH_2$—$CH_2$—$CH_2$— are preferred.

Compounds in which R is hydrogen are more preferred.

When R is $C_1$-$C_6$ alkyl, compounds in which R is methyl are more preferred.

Compounds in which $R^1$ is hydrogen or $C_1$-$C_3$ alkyl are preferred.

Compounds in which $R^2$ is $C_1$-$C_6$ alkyl are preferred.

Compounds in which $R^2$ is methyl are more preferred.

When $R^3$ is halo, the compounds in which $R^3$ is fluoro are preferred.

Compounds in which $R^4$ is hydrogen, $C_1$-$C_6$ alkyl, or halo are preferred.

Compounds in which X is halo are preferred.

When X is halo, the compounds in which X is fluoro are preferred.

When X is fluoro, the compounds in which X is 2,6-difluoro are more preferred.

The compounds of formula I are prepared as described in Scheme A. In Scheme A all substituents, unless otherwise indicated, are as previously defined, and all reagents are well known and appreciated in the art.

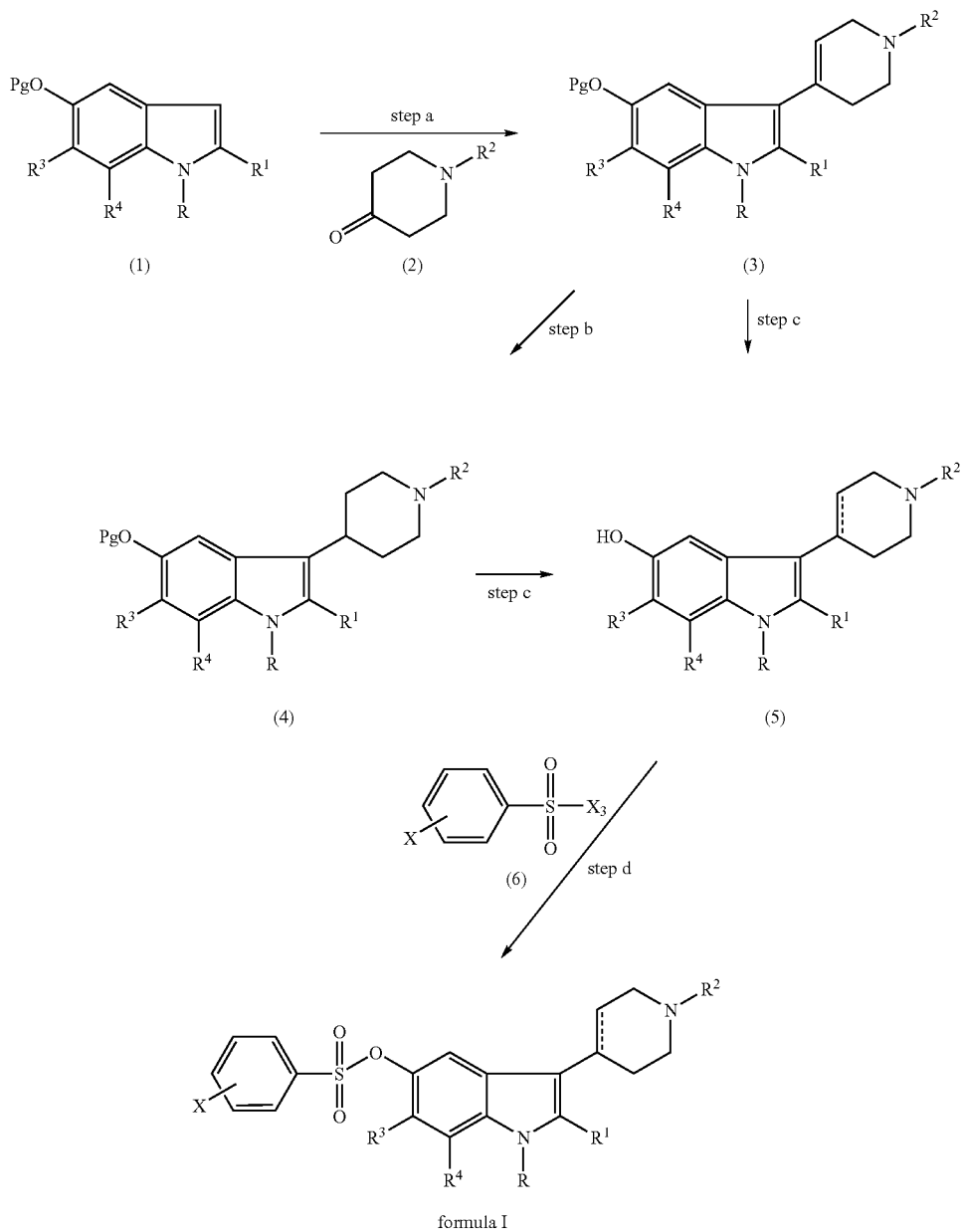

Scheme A formula I

The specific sequence of reactions depicted in Scheme A is not critical. For many of the compounds of formula I the order of these steps can be varied to provide compounds of formula I. In addition, variation with regard to the introduction the group R, the use of protecting groups, and modification to give various $R_2$ and $R_4$ groups can be used. Some of the possible variations are discussed below.

In Scheme A, step a, an appropriate indole of formula (1) is condensed with an appropriate piperidin-4-one of formula (2) to give a 3-(1,2,3,6-tetrahydropyridin-4-yl)-1H-indole of formula (3). An appropriate indole of formula (1) may be one in which Pg is an protecting group and R, $R^1$, $R^3$, and $R^4$ are as desired in the final product of formula I. The selection and use of suitable protecting groups are well known and appreciated in the art (*Protecting Groups in Organic Synthesis*, Theodora Greene (Wiley-Interscience)). Preferred protecting groups include methyl, benzyl, and dimethyl-t-butylsilyl. As one of the variations mentioned above, the indoles of formula (1) having a 5-hydroxy, are also suitable for the reaction in step a. Thus, an appropriate indole of formula (1) is also one having a 5-hydroxy, instead of the protected hydroxy depicted. Such unprotected compound of formula (1), when used, directly give compounds of formula (5). Also, as will be appreciated by the skilled person, the indoles of formula (1) in which R is hydrogen can give rise upon alkylation or sulfonation at a later point, to compounds of formula I in which R is not hydrogen. An appropriate piperidin-4-one of formula (2) is most conveniently one in which $R^2$ is as desired in the final product of formula I.

Appropriate indoles of formula (1) are generally available from commercial sources. Appropriate indoles of formula (1) can also be prepared by methods described herein and by methods described in the art, for example, Robinson, The Fischer Indole Synthesis, Wiley, N.Y. (1983); Hamel, et al., Journal of Organic Chemistry, 59, 6372 (1994); and Russell, et al., Organic Preparations and Procedures International, 17, 391 (1985). Appropriate piperidin-4-ones of formula (2) are readily available and can be prepared by the alkylation of piperidin-4-one.

For example in step a, an appropriate indole of formula (1) is condensed with an appropriate piperid-4-one of formula (2) to give a 3-(1,2,3,6-tetrahydropyridin-4-yl)-1H-indole of formula (3). When the appropriate indole of formula (1) is one in which R is hydrogen, the reaction is typically carried out in the presence of a suitable base, typically sodium hydroxide, potassium hydroxide, sodium alkoxide, (such as sodium methanolate or sodium ethanolate), or potassium alkoxide, (such as potassium methanolate, potassium ethanolate, or potassium t-butoxide). The reaction is carried out in a suitable solvent, such as methanol, ethanol, tetrahydrofuran, or mixtures of methanol or ethanol and tetrahydrofuran. Typically, about 2 molar equivalents of piperid-4-one of formula (2) are used. The reaction is generally carried out at temperatures of about 40° C. to the reflux temperature of the selected solvent. The reaction typically requires 8-72 hours. In general, the basic conditions are favored for the condensation above compounds of formula (1) in which Pg is a protecting group. The product can be isolated and purified by techniques well known in the art, such as precipitation, filtration, extraction, evaporation, trituration, chromatography, and recrystallization.

Alternately, for example in step a, an appropriate indole of formula (1) is condensed with an appropriate piperid-4-one of formula (2) to give a 3-(1,2,3,6-tetrahydropyridin-4-yl)-1H-indole of formula (3). The reaction may carried out in the presence of a suitable acid, typically phosphoric acid or sulfuric acid. The reaction is carried out in a suitable solvent, such as acetic acid and water. Typically, about 2-6 molar equivalents of the piperid-4-one of formula (2) are used. The reaction is generally carried out at temperatures of about 40° C. to 100° C. The reaction typically requires 8-72 hours. In general, the acidic conditions are favored for the condensation above compounds of formula (1) having a 5-hydroxy. The product can be isolated and purified by techniques well known in the art, such as precipitation, filtration, extraction, evaporation, trituration, chromatography, and recrystallization.

Reaction Scheme A, step b, depicts the reduction of a 3-(1,2,3,6-tetrahydropyridin-4-yl)-1H-indole of formula (3) to give a 3-(piperidin-4-yl)-1H-indole of formula (4).

For example, a 3-(1,2,3,6-tetrahydropyridin-4-yl)-1H-indole of formula (3) may be hydrogenated over a catalyst, such as palladium on carbon or platinum oxide, to give a 3-(piperidin-4-yl)-1H-indole of formula (4). Such hydrogenations are generally carried out in a solvent and a variety of solvents are suitable, for example methanol, ethanol, or isopropanol, tetrahydrofuran, or mixed solvents, such as tetrahydrofuran and ethyl acetate. The hydrogenation may be performed at an initial hydrogen pressure of 20-180 psi (137-1241 kPa), preferably from 50-60 psi (345-413 kPa). The reaction is typically carried out at temperature of about 0° C. to about 60° C., preferably at temperatures of about 40° C. to 60° C. The reaction typically requires 1 hour to 3 days. The product can be isolated and purified by techniques well known in the art, such as filtration, extraction, evaporation, trituration, precipitation, chromatography, and recrystallization.

As an alternative to hydrogenation, 3-(1,2,3,6-tetrahydropyridin-4-yl)-1H-indole of formula (3) may be converted to a 3-(piperidin-4-yl)-1H-indole of formula (4) by treatment with triethylsilane/trifluoroacetic acid, if desired. The 3-(1,2,3,6-tetrahydropyridin-4-yl)-1H-indole of formula (3) is dissolved in trifluoroacetic acid to which is added an excess, generally 1.5-10 equivalents, of triethylsilane. The reaction mixture is generally carried out at ambient temperature for about 1 to about 48 hours. The product is isolated by concentrating under reduced pressure and then treated with 2N sodium or potassium hydroxide or tartaric acid and extracting. The product can be purified by techniques well known in the art, such as filtration, extraction, evaporation, trituration, precipitation, chromatography, and recrystallization.

Another alternative to the above reduction conditions, 3-(1,2,3,6-tetrahydropyridin-4-yl)-1H-indole of formula (3) may be reduced by treatment with 1-4 equivalents of sodium borohydride with or without an acid such as acetic acid or trifluoroacetic acid. The reaction is generally carried out in a solvent, such as tetrahydrofuran. The reaction is typically carried out at temperature of from about 0° C. to about 60° C., most conveniently at ambient temperature. The reaction typically requires 1 to 3 hours. The product can be isolated and purified by techniques well known in the art, such as precipitation, filtration, extraction, evaporation, trituration, chromatography, and recrystallization.

As one of the variations discussed above, this is a convenient point in the synthesis to alkylate or sulfonate, if desired, a 3-(1,2,3,6-tetrahydropyridin-4-yl)-1H-indole of formula (3) or a 3-(piperidin-4-yl)-1H-indole of formula (4) in which R is hydrogen.

For example, a 3-(1,2,3,6-tetrahydropyridin-4-yl)-1H-indole of formula (3) or a 3-(piperidin-4-yl)-1H-indole of formula (4) is contacted with an appropriate alkylating agent or sulfonating agent. An appropriate alkylating agent or sulfonating agent is one that transfers an R group as desired in the final product of formula I. Appropriate alkylating agents are $RX_1$ in which R is an $C_1$-$C_6$ alkyl or substituted $C_1$-$C_6$ alkyl as desired and $X_1$ is a leaving group, such as bromo, chloro, iodo, or tosylate. Appropriate sulfonating agents are $R'SO_2X_2$ in which transfers a sulfonyl containing R as desired and $X_2$ is a leaving group, typically chloro, fluoro, or another group $R'SO_2O$— to form the anhydride of the sulfonating agent. Such reactions are carried out in a suitable solvent such as dimethyl sulfoxide, acetonitrile, dimethylformamide, or tetrahydrofuran at temperatures of from about −20° C. to ambient temperature. The reaction is carried out using an appropriate base such as sodium hydride or potassium hydride and may advantageously use a catalyst such as, 18-crown-6 ether. Generally, 1-4 equivalents of an appropriate alkylating agent or sulfonating agent are used. The reaction typically requires 1 to 18 hours. The product can be isolated and purified by techniques well known in the art, such as quenching, filtration, extraction, evaporation, trituration precipitation, chromatography, and recrystallization.

In Scheme A, step c, a 3-(1,2,3,6-tetrahydropyridin-4-yl)-1H-indole of formula (3) or a 3-(piperidin-4-yl)-1H-indole of formula (4) is deprotected to give a compound of formula (5). The removal of suitable protecting groups is well known and appreciated in the art (*Protecting Groups in Organic Synthesis*, Theodora Greene (Wiley-Interscience)).

In Scheme A, step d, a compound of formula (5) is contacted with an appropriate sulfonating agent of formula (6) to give a compound of formula I. An appropriate sulfonating agent of formula (6) is one in which X is, or gives rise to X, a desired in the compound of formula I and $X_3$ is a leaving group, typically fluoro or chloro, or is the anhydride of the sulfonating agent of formula (6). As one the possible variations mentioned above, the skilled person will appreciate that unprotected compounds, that is, indoles of formula (1) having a 5-hydroxy, may undergo sulfonation as described in Scheme A, step d, and subsequently undergo the chemistry of Scheme A, step a, to give a compound of formula I.

For example, a compound of formula (5) is contacted with from 1-10 equivalents of an appropriate sulfonating agent of formula (6). The reaction is generally carried out in a solvent such as dimethyl sulfoxide, acetonitrile, dimethylformamide, water, or tetrahydrofuran at temperatures of from about −20° C. to ambient temperature. The reaction is carried out using an appropriate base such as sodium hydride, potassium hydride, sodium hydroxide, or potassium hydroxide. The reaction typically requires 1 to 18 hours. The product can be isolated and purified by techniques well known in the art, such as quenching, filtration, extraction, evaporation, trituration, precipitation, chromatography, and recrystallization.

Alternately, a compound of formula (5) is contacted with from 1-10 equivalents of an appropriate sulfonating agent of formula (6) in a solvent such as dimethyl sulfoxide, acetonitrile, dimethylformamide, or tetrahydrofuran. An organic base is added such as, triethylamine, collidines, pyridine, or lutidines. The compounds of formulas (5) and (6) are generally stirred at room temperature and the organic base is added dropwise. When carried out with an organic base, the reaction typically requires 48 to 72 hours. The product can be isolated and purified by techniques described above.

The compound of formula I thus obtained can be further elaborated, if desired. For example, when step d is carried out using a compound or formula (6) in which X is nitro the compound of formula I, can be reduced by hydrogenation over 5% palladium on carbon in an appropriate solvent such as ethanol at atmospheric pressure to give the compound of formula I in which X is amino. The amino group can be further elaborated, as is well known in the art, by sulfonation to give further compounds of formula I. Also, a compound in which $R_4$ is halo, in particular bromo can undergo a variety of coupling reactions to give compounds in which $R_4$ is vinyl, allyl, or $C_2$-$C_6$ alkynyl.

Scheme A, optional step e, not shown, an acid addition salt of a compound of formula I is formed using a pharmaceutically-acceptable acid. The formation of acid addition salts is well known and appreciated in the art.

The present invention is further illustrated by the following examples and preparations. These examples and preparations are illustrative only and are not intended to limit the invention in any way.

The terms used in the examples and preparations have their normal meanings unless otherwise designated. For example, "° C." refers to degrees Celsius; "N" refers to normal or normality; "M" refers to molar or molarity; "mmol" refers to millimole or millimoles; "g" refers to gram or grams; "mL" refers to milliliter or milliliters; "mp" refers to melting point; "brine" refers to a saturated aqueous sodium chloride solution; etc. In the $^1$H NMR, all chemical shifts are given in δ, unless otherwise indicated.

PREPARATION 1

5-Methoxy-7-methyl-1H-indole

To a solution of 4-methoxy-2-methylanaline (0.36 mole, 50.0 g) in methylene chloride (450 mL) cooled to 10° C. (acetone/ice) was added a solution of 1.0 M boron trichloride in methylene chloride (0.50 mole, 500 mL) while maintaining the reaction temperature below −10° C. Chloroacetonitrile (1.82 mole, 137.6 g) was added to the reaction while maintaining the internal temperature below 0° C. This was followed by the addition of diethylaluminum chloride (0.40 mole, 48.34 g, 50 mL) while maintaining the reaction temperature below 0° C. The solution was then refluxed for 5.25 hours. The reaction was cooled to room temperature and carefully treated with 5N hydrochloric acid (0.450 L) and water (1 L). The suspension was heated to reflux and cooled to room temperature. The phases were separated and the aqueous phase was extracted with methylene chloride (3×500 mL). The combined organic phases were filtered through a pad of silica (height of silica=8 cm) in a scintered glass funnel (inner diameter of funnel=12 cm). Material eluted from silica pad with methylene chloride (3×500 mL) to afford 1-(2-amino-5-methoxy-3-methylphenyl)-2-chloroethanone plus chloroacetonitrile. The mixture was concentrated in vacuo to afford 40.1 g (51%) 1-(2-amino-5-methoxy-3-methylphenyl)-2-chloroethanone that slowly crystallized. A solution of 1-(2-amino-5-methoxy-3-methylphenyl)-2-chloroethanone (0.19 mole, 40.1 g) in 9:1 dioxane:water (935 mL) was added sodium borohydride (0.19 mole, 7.1 g). The reaction was stirred one hour at room temperature refluxed for 4.5 hours. The reaction was cooled to room temperature and treated with 1N hydrochloric acid (310 mL). This mixture was heated to 80° C. and cooled to room temperature. The reaction was treated with water (500 mL), extracted with ethyl acetate (3×500 mL) and the organic phases were combined, concentrated in vacuo to afford an oil. The oil was dissolved in methylene chloride and filtered through a pad of silica (height of silica=10 cm) in a scinter glass funnel (inner diameter of funnel=14.5 cm).

Material eluted with methylene chloride. Fractions containing the title compound were combined, concentrated in vacuo to afford 23.32 g (77%) of the title compound as an oil: mass spectrum (ion spray): m/z=161 (M); $^1$H NMR (DMSOd$_6$): 7.25 (t, J=2.93 Hz, 1H), 6.84 (d, J=2.20 Hz, 1H), 6.53 (d, J=1.46 Hz, 1H), 6.32 (dd, J=2.93, 1.83 Hz, 1H), 3.71 (s, 3H), 2.41 (s, 3H).

PREPARATION 2

5-Methoxy-6-fluoro-1H-indole

Fuming nitric acid (24 mL) was dissolved in concentrated H$_2$SO$_4$ in a round bottom flask. 3,4-Difluorobromobenzene (20 g, 104 mmol) was added dropwise via pipette with vigorous stirring. After addition was complete, the reaction was allowed to stir at room temperature for 2 hours. The reaction was poured into ice water and extracted 2×250 mL with Et$_2$O. The organic layers were collected, combined, dried over MgSO$_4$, filtered, and the solvent removed leaving a light yellow oil (24.02 g, 97% yield) of 1-bromo-4,5-difluoro-2-nitro-benzene.

1-Bromo-4,5-difluoro-2-nitro-benzene (24 g, 100 mmol) was carefully added dropwise to a solution of sodium methoxide (1.2 eq) in MeOH. After addition was complete, the reaction was stirred at room temperature for 2.5 hours. The solvent was removed in vacuo and the residue diluted with water and extracted 2×250 mL with Et$_2$O. The organic layers were combined, dried over MgSO$_4$, filtered, and the solvent removed in vacuo leaving a yellow solid of 1-bromo-4-fluoro-5-methoxy-2-nitro-benzene: $^1$H NMR (300 MHz, CDCl$_3$) 3.99 (s, 3H), 7.26 (m,1H) , 7.83 (d, 1H). MS(FD+): m/z 249, 251 (M+). Calculated for C$_7$H$_5$BrFNO$_3$: C, 33.63; H, 2.02; N, 5.60; found: C, 33.79; H, 1.98; N, 5.62. 1-Bromo-4-fluoro-5-methoxy-2-nitro-benzene (20.5 g, 82 mmol) was hydrogenated over Pt on C (sulfided) at 60 psi (413 kPa) in THF (600 mL) for 4 hours. The reaction was filtered through celite to remove the catalyst. Removal of the solvent left a brown solid of 2-bromo-5-fluoro-4-methoxy-phenylamine which was taken on without further purification. 2-Bromo-5-fluoro-4-methoxy-phenylamine (18 g, 81.8 mmol) was dissolved in pyridine (200 mL) in a 500 mL round bottom flask equipped with a stir bar, septum, pressure equalizing dropping funnel, and nitrogen line with bubbler. The solution was cooled in an ice bath and ethyl chloroformate (1.5 eq.,122.7 mmol) was added dropwise from the dropping funnel. After addition was complete, the reaction was allowed to stir overnight gradually warming to room temperature. The pyridine was removed leaving a brown residue. This residue was taken up in Et$_2$O/water and transferred to a separatory funnel. The water was extracted with Et$_2$O (2×300 mL). The organic layers were combined, dried over MgSO$_4$, filtered, concentrated in vacuo to obtain a 23.62 g (99%) of a brown solid: $^1$H NMR (300 MHz, CDCl$_3$, 1.33 (t, 3H), 3.85 (s, 3H), 4.23 (q, 2H), 7.09 (d, 1H), 7.97 (bd, 1H); MS(FD+): m/z 291, 293 (M+).

(2-Bromo-5-fluoro-4-methoxy-phenyl)-carbamic acid ethyl ester (23 g, 78.74 mmol) was converted to the ethynyl compound following a similar example in *J. Org. Chem.* 199, 62, 6507. The compound was purified by absorbing to silica gel and loading onto a pad of silica and using 7.5% EtOAc in hexanes as the mobile phase. Fractions containing the product were pooled and the solvent removed in vacuo leaving a yellow solid: mass spectra (ES+): m/z 310 (M+H)$^+$; (ES−): m/z 308 (M−H)$^-$.

A solution of sodium ethoxide (formed by dissolving NaH 11.45 g, 60% in oil, 286.2 mmol, 4 eq.) in ethanol was poured into an EtOH solution of (5-fluoro-4-methoxy-2-trimethylsilanylethynyl-phenyl)-carbamic acid ethyl ester (22.14 g, 71.55 mmol) in EtOH (250 mL). The reaction was allowed to stir at room temperature for 2 hours and heated to 75° C. overnight. The EtOH was removed in vacuo and the residue diluted with water. The aqueous suspension was extracted 2×300 mL with Et$_2$O. The organics were combined and washed with brine. The organic layer was collected, dried over MgSO$_4$, filtered, and the solvent removed in vacuo leaving a dark red oil. The oil was purified by silica gel flash column chromatography using 15% EtOAc in hexanes as the mobile phase. Removal of the solvent in vacuo from the fractions containing the product left a golden yellow oil which solidified on standing: $^1$H NMR (300 MHz, CDCl$_3$): 3.93 (s, 3H), 6.48 (m, 1H), 7.15 (m, 3H), 8.11 (bs, 1H); MS(ES+): m/z 166 (M+H)$^+$; MS(ES−): m/z 164 (M−H)$^-$; Calculated for C$_9$H$_8$FNO: C, 65.45; H, 4.88; N, 8.48; found: C, 65.17; H, 4.97; N, 8.70.

PREPARATION 3

3-(1-Methyl-1,2,3,6-tetrahydropyridin-4-yl)-5-hydroxy-1H-indole

To a solution of 1H-indol-5-ol (18.60 g, 0.14 mol) in methanol (250 ml), stirring at room temperature under nitrogen, was slowly added potassium hydroxide (31.4 g, 0.56 mol) in methanol (100 mL). 1-methyl-4-piperidone (29.0 mL, 0.24 mol) was added dropwise to the black solution. The reaction mixture was heated at 70° C. for 8 hours, cooled to room temperature, concentrated in vacuo. The resulting residue was directly purified on silica gel. Elution with a 9:1 mixture of dichloromethane and 7 N ammonia in methanol provided 21.25 g (62%) of the title compound as a tan solid: mp=182-185° C.; $^1$H NMR (400 MHz, dmso-d$_6$): 10.78 (br s, 1H), 8.64 (s, 1H), 7.22 (d, 1H, J=2.4 Hz), 7.13 (d, 1H, J=8.8 Hz), 7.10 (d, 1H, J=1.6 Hz), 6.59 (dd, 1H, J=8.8, 1.2 Hz), 5.94 (br s, 1H), 3.02-2.98 (m, 2H), 2.52 (br t, 2H, J=5.6 Hz), 2.48-2.42 (m, 2H), 2.24 (s, 3H); MS (APCI): m/e 229.1 (M+1).

PREPARATION 4

5-Benzyloxy-3-(1-methyl-1,2,3,6-tetrahydropyridin-4-yl)-1H-indole

To a solution of potassium hydroxide (22 g, 392 mmol) in methanol (160 mL) was added 5-benzyloxyindole (24.7 g, 111 mmol) followed by 1-methyl-4-piperidone (17.7 mL, 144 mmol) and methanol (80 mL). The reaction mixture was stirred at reflux for 18 h, cooled to ambient temperature and filtered. The precipitate was washed with methanol and dried under vacuum to give 31.7 g (90%) of the title compound: mp=197-199° C. dec; MS(m/e): 318 (M$^+$). Calculated for C$_{21}$H$_{22}$N$_2$O: C, 79.21; H, 6.96; N, 8.80. Found: C, 79.24; H, 6.99; N, 8.85.

PREPARATION 5

6-Fluoro-5-methoxy-3-(1-methyl-1,2,3,6-tetrahydropyridin-4-yl)-1H-indole

By a method similar Preparation 3 using 1-methyl-4piperidone (18.7 mmole, 2.11 g), potassium hydroxide (62.3 mmole, 3.49 g) 6-fluoro-5-methoxy-1H-indole (17.8 mmole, 2.94 g) to afford 4.11 g (88%) of the title compound: Mass spectrum (ion spray): m/z=261 (M+1); $^1$H NMR (DM- SOd$_6$): 7.37 (d, 1H), 7.32 (d, 1H), 7.19 (d, 1H), 6.09 (t, 1H), 3.86 (s, 3H), 3.05 (d, 2H), 2.51 (m, 2H), 2.49 (m, 2H), 2.29 (s, 3H); Calculated for C$_{15}$H$_{17}$FN$_2$O: C, 69.21; H, 6.58; N, 10.76. Found: C, 69.14; H, 6.59; N, 10.72.

PREPARATION 6

5-Methoxy-7-methyl-3-(1-methyl-1,2,3,6-tetrahydropyridin-4-yl)-1H-indole

By a method similar to Preparation 3, using 5-methoxy-7-methyl-1H-indole (0.12 mole, 20.02 g), methanol (240 mL), potassium hydroxide (0.43 mole, 24.39 g) and 1-methyl-4-piperidone (0.13 mole, 14.76 g) afforded 24.72 (78%) of the title compound: Mass spectrum (ion spray): m/z= (ES+) 257 (M+1), (ES−) 255 (M−1); $^1$H NMR (DMSOd$_6$): 7.32 (s, 1H), 7.06 (1H), 6.59 (1H), 6.05 (m, 1H), 3.75 (s, 3H), 3.04 (2H), 2.50 (m, 4H), 2.42 (s, 3H), 2.29 (s, 3H).

PREPARATION 7

7-Methoxy-9-(1-methyl-1,2,3,6-tetrahydropyridin-4-yl)-2,3-dihydro-1H-pyrrolo[1,2-a]indole To a solution of 7-methoxy-2,3-dihydro-1H-pyrrolo[1,2-a]indole (718 mg, 3.83 mmol) (Clark, R. D.; Muchowski, J. M.; Fisher, L. E.; Flippen, L. A.; Repke, D. B.; Souchet, M. Synthesis 10,871-878(1991); Ishikura, M.; Terashima, M. Tetrahedron Lett. 33, 6849-6852(1992)) in glacial AcOH (20 mL) at 60° C. was added H$_3$PO$_4$ (5.0 mL, 10 mmol, 2.0 N) and 1-methyl-4-piperidone (1.2 mL, 11.5 mmol). The reaction was heated for 1 h at 60° C., cooled to room temperature and poured into a mixture of ammonium hydroxide in ice water. This reaction mixture was extracted with ethyl acetate and washed with brine, dried over Na$_2$SO$_4$, filtered, and concentrated under reduced pressure yielded 1.07 g (99%) of the title compound as a brown oil: MS (ES+): m/e 283.0 (M+1).

PREPARATION 8

7-Methyl-3-(1-methylpiperidin-4-yl)-1H-indole-5-ol

In a round bottom flask was placed 5-methoxy-7-methyl-3-(1-methylpiperidin-4-yl)-1H-indole (3.9 mmole, 1.01 g) and pyridine hydrochloride (25 g). The flask was then placed in a preheated oil bath set at 190° C. for 45 minutes. This solution was cooled to room temperature. The resulting solidified material was dissolved in water (200 mL). The pH was adjusted to approximately 10.3, which resulted in a precipitate. The insoluble material was collected by filtration, rinsed with water to afford 0.781 g (82%) of the title compound: mass spectrum (ion spray): m/z=245 (M+1); $^1$H NMR (DMSOd$_6$): 10.40 (s, 1H), 8.45 (s, 1H), 6.93 (s, 1H), 6.68 (s, 1H), 6.40 (s, 1H), 2.90 (m, 2H), 2.60 (m, 1H), 2.36 (s, 3H), 2.26 (s, 3H), 2.08 (m, 2H), 1.90 (m, 2H), 1.70 (m, 2H); Calculated for C$_{15}$H$_{20}$N$_2$O: C, 73.74; H, 8.25; N, 11.47. Found: C, 73.76; H, 8.15; N, 11.71.

PREPARATION 9

2-Methyl-3-(1-methylpiperidin-4-yl)-5-hydroxy-1H-indole hydrochloride

By a method similar to Preparation 8, using 2-methyl-5-methoxy-3-(1-methylpiperidin-4-yl)-5-hydroxy-1H-indole (258 mg, 1.0 mmol) and 25 g of pyridine hydrochloride gave the crude product. Flash chromatography [silica gel, dichloromethane/2N NH$_3$ (methanol) (90/10)] gave 244 mg (100%) of the final product as a colorless oil. Formation of the hydrochloride salt in Et$_2$O provided a white solid: mp=175° C.; MS(m/e): 245 (M+1); Calculated for C$_{15}$H$_{20}$N$_2$O.HCl.0.3 Et$_2$O.0.3H$_2$O: C, 63.08; H, 8.04; N, 9.08. Found: C, 62.97; H, 8.11; N, 8.69.

PREPARATION 10

7-Methyl-3-(1-methylpiperdin-4-yl)-1-phenethyl-1H-indol-5-ol

By a method similar to Preparation 8, using 5-methoxy-7-methyl-3-(1-methylpiperdin-4-yl)-1-phenethy-1H-indole (0.288 g) and pyridine hydrochloride (25 g) to afford 0.143 (52%) of the title compound: mass spectrum (ion spray): m/z=349 (M+1); Calculated for C$_{23}$H$_{28}$N$_2$O-0.3H$_2$O: C, 78.06; H, 8.15; N, 7.92. Found: C, 78.24; H, 8.18; N, 8.11.

PREPARATION 11

6-Fluoro-3-(1-methylpiperidin-4-yl)-1H-indole-5-ol

By a method similar to Preparation 8, using 6-fluoro-5-methoxy-3-(1-methylpiperidin-4-yl)-1H-indole (0.410 g) and 25 g of pyridine hydrochloride gave 0.360 g (93%) the title compound: Mass spectrum (ion spray): m/z=248 (M).

PREPARATION 12

1-Benzyl-7-methyl-3-(1-methylpiperdin-4-yl)-5-hydroxy-1H-indole

By a method similar to Preparation 8, using 1-benzyl-5-methoxy-7-methyl-3-(1-methylpiperdin-4-yl)-1H-indole (1.62 g) and pyridine hydrochloride (25 g) to afford 0.936 g (60%) of the title compound: Mass spectrum (ion spray): m/z=335 (M+1).

PREPARATION 13

1-Propyl-7-methyl-3-(1-methylpiperdin-4-yl)-5-hydroxy-1H-indole

By a method similar to PREPARATION 8, using 1-propyl-5-methoxy-7-methyl-3-(1-methylpiperdin-4-yl)-1H-indole (1.24 g) and pyridine hydrochloride (25 g) to afford 1.03 g (87%) of the title compound: mass spectrum (ion spray): m/z=287 (M+1); Calculated for C$_{18}$H$_{26}$N$_2$O.0.4 H$_2$O: C, 73.63; H, 9.34; N, 9.23. Found: C, 73.70; H, 9.34; N, 9.33.

PREPARATION 14

1-Ethyl-7-methyl-3-(1-methylpiperdin-4-yl)-5-hydroxy-1H-indole

By a method similar to Preparation 8, using 1-ethyl-5-methoxy-7-methyl-3-(1-methylpiperdin-4-yl)-1H-indole (1.13 g) pyridine hydrochloride (25 g) to afford 0.996 g (93%) of the title compound: mass spectrum (ion spray): m/z=273 (M+1); Calculated for C$_{17}$H$_{24}$N$_2$O-0.6 H$_2$O: C, 72.10; H, 8.97; N, 9.89. Found: C, 72.09; H, 8.97; N, 9.85.

PREPARATION 15

1,7-Dimethyl-3-(1-methylpiperdin-4-yl)-5-hydroxy-1H-indole

By a method similar to Preparation 8, using 5-methoxy-1,7 dimethyl-3-(1-methylpiperdin-4-yl)-1H-indole (1.53 g) and pyridine hydrochloride (25 g) to afford 1.33 g (92%) of the title compound: mass spectrum (ion spray): m/z=259 (M+1); $^1$H NMR (DMSOd$_6$): 8.47 (s, 1H), 6.81 (s, 1H), 6.62 (d, J=2.20 Hz, 1H), 6.33 (d, J=1.46 Hz, 1H), 3.88 (s, 3H), 2.82 (m, 2H), 2.53-2.46 (m, 4H), 2.19 (s, 3H), 1.99 (m, 2H), 1.84 (m, 2H), 1.64 (m, 1H), 1.56 (m, 1H); Calculated for $C_{16}H_{22}N_2O$-0.6 $H_2O$: C, 71.39; H, 8.69; N, 10.41. Found: C, 71.39; H, 8.31; N, 10.33.

PREPARATION 16

9-(1-Methylpiperidin-4-yl)-2,3-dihydro-1H-pyrrolo[1,2-a]indol-7-ol

7-Methoxy-9-(1-methylpiperidin-4-yl)-2,3-dihydro-1H-pyrrole[1,2-a]indole (0.92 g, 3.23 mmol) was dissolved in HBr (8.0 mL, 49%) and heated within a range of 105-115° C. for 2.5 h. The reaction mixture was concentrated under reduced pressure and the residue was partitioned between $CH_2Cl_2$, IPA, and aq. $K_2CO_3$. The organic layer was washed with brine, dried ($K_2CO_3$), filtered, and reduced under pressure. The residue was purified by PCTLC (silica gel GF rotor; 95:5 $CHCl_3$:2M $NH_3$ in MeOH) to give 705 mg (81%) of a pale pink foam. The hydrochloride was formed in EtOAc to give the title compound as a white solid: mp>250° C.; MS (ES+): m/e 285.0 (M+1); Calculated for $C_{17}H_{22}N_2O$ 1.1HCl: Calcd: C, 65.77; H, 7.50; N, 9.06. Found: C, 65.72; H, 7.53; N, 8.93.

PREPARATION 17

3-(1-Methylpiperidin-4-yl)-5-hydroxy-1H-indole

A mixture of 5-benzyloxy-3-(1-methyl-1,2,3,6-tetrahydropyridin-4-yl)-1H-indole (16.4 g, 51.5 mmol) and 5% palladium on carbon (4.0 g) in ethanol (125 mL) and tetrahydrofuran (125 mL) was hydrogenated with an initial hydrogen pressure of 60 psi (413 kPa) at ambient temperature for 16 h. The reaction mixture was filtered and concentrated under reduced pressure. The residue was crystallized from methanol and THF to give 6.06 g (51%) of the title compound as white crystals: mp=234-237° C.; MS(m/e): 230 (M$^+$); Calculated for $C_{14}H_{18}N_2O$: Calcd: C, 73.01; H, 7.88; N, 12.16. Found: C, 72.79; H, 8.17; N, 12.33.

PREPARATION 18

1-Methyl-3-(1-methylpiperidin-4-yl)-5-hydroxy-1H-indole oxalate hemihydrate

A mixture of 5-benzyloxy-1-methyl-3-(1-methyl-1,2,3,6-tetrahydropyridin-4-yl)-1H-indole (955 mg, 2.87 mmol) and 5% palladium on carbon (240 mg) in methanol (100 mL) was hydrogenated with an initial hydrogen pressure of 60 psi (413 kPa) at ambient temperature for 16 h. The reaction mixture was filtered and concentrated under reduced pressure. The product was purified by flash chromatography (silica gel, 5% 2M ammonia in methanol/methylene chloride) to give 437 mg (62%) of homogeneous product as purple foam. The product was crystallized as the oxalic acid salt from ethyl acetate to give the title compound as a white powder: mp=68-75° C. dec.; MS(m/e): 245 (M+1); Calculated for $C_{15}H_{20}N_2O \cdot C_2H_2O_4 \cdot 0.5H_2O$: C, 57.94; H, 6.86; N, 7.95. Found: C, 58.17; H, 6.53; N, 8.04.

PREPARATION 19

5-(t-Butyldimethylsilanyloxy)-3-(1-methylpiperidin-4-yl)-1H-indol

To a solution of 3-(1-methyl-pyridin-4-yl)-5-hydroxy-1H-indole (8.0 g, 34.7 mmol) and 1-methyl-2-pyrrolidinone (10 mL) in dichloromethane (90 mL) stirring at 0° C., was added tert-butyldimethylsilyl chloride in small portions (5.50 g, 36.5 mmol), followed by imidazole also in small portions (2.48 g, 36.5 mmol). The reaction mixture was stirred for 1 hour at 0° C., then overnight at room temperature. The mixture was concentrated in vacuo to a solid residue, which was directly purified on silica gel. Elution with a 9:1 mixture of dichloromethane and methanol provided 7.60 g (63%) of the title compound as a white solid: mp=191-195° C.; $^1$H NMR (400 MHz, dmso-d$_6$): 10.46 (s, 1H), 7.02 (d, 1H, J=8.4 Hz), 6.87 (d, 1H, J=2.4 Hz), 6.74 (d, 1H, J=2.4 Hz), 6.45 (dd, 1H, J=8.6, 2.6 Hz), 2.69 (br d, 2H, J=11.2 Hz), 2.46 (tt, 1H, J=11.8, 3.6 Hz), 2.04 (s, 3H), 1.92-1.80 (m, 2H), 1.75-1.67 (m, 2H), 1.50 (qd, 2H, J=12.4, 3.6 Hz), 0.81 (s, 9H), 0.00 (s, 6H); MS (APCI): m/e 345 0.2 (M+1).

PREPARATION 20

7-Methoxy-9-(1-methylpiperidin-4-yl)-2,3-dihydro-1H-pyrrole[1,2-a]indole

To a solution of 7-methoxy-9-(1-methyl-1,2,3,6-tetrahydropyridin-4-yl)-2,3-dihydro-1H-pyrrolo[1,2-a]indole (1.07 g, 3.79 mmol) in $CH_2Cl_2$ (20 mL) was slowly added trifluoroacetic acid added. The clear solution was then cooled to 0° C. and Et$_3$SiH (0.61 mL, 3.79 mmol) was added dropwise. The reaction mixture was then allowed to stir for an additional 2 h at 0° C. The solution was concentrated under reduced pressure, dissolved in tartaric acid, washed with hexanes, basified ($K_2CO_3$), and extracted with $CH_2Cl_2$. The organic layer was dried ($K_2CO_3$), concentrated under reduced pressure, and purified by PCTLC (silica gel GF rotor; 95:5 $CHCl_3$:2M $NH_3$ in MeOH) to give 1.05 g (97%) of a yellowish foam: MS (ES+): m/e 285.0 (M+1).

PREPARATION 21

3-(1-Methylpiperidin-4-yl)-5-hydroxy-1H-indole

By a method similar to Preparation 20, using 3-(1-methyl-1,2,3,6-tetrahydropyridin-4-yl)-5-hydroxy-1H-indole (1.25 g, 5.47 mmol) in dichloromethane (5 mL) trifluoroacetic acid (5 mL), triethylsilane (875 mL, 6.0 mmol) afforded 1.14 g (90%) of the title compound as a tan solid: mp=233-237° C.; $^1$H NMR (400 MHz, dmso-d$_6$): 10.41 (br s, 1H), 8.52 (br s, 1H), 7.08 (d, 1H, J=8.0 Hz), 6.92 (d, 1H, J=2.0 Hz), 6.80 (d, 1H, J=2.0 Hz), 6.53 (dd, 1H, J=8.4, 2.0 Hz), 2.84 (br d, 2H, J=11.2 Hz), 2.63-2.50 (m, 1H), 2.19 (s, 3H), 2.08-1.97 (m, 2H), 1.85 (br d, 2H, J=12.0 Hz), 1.72-1.57 (m 2H); MS (ES+) m/e 231.0 (M+1).

PREPARATION 22

5-Benzyloxy-3-(1-methylpiperidin-4-yl)-1H-indole

By a method similar to Preparation 20, using trifluoroacetic acid (1.6 mL), 5-benzyloxy-3-(1-methyl-1,2,3,6-tetrahydropyridin-4-yl)-1H-indole (222 mg, 0.7 mmol), methylene chloride (3 mL) and triethylsilane (111 μL, 0.7 mmol) gave the tile compound as a yellow foam (210 mg) which was crystallized from ethyl acetate to give 160 mg of pale yellow crystals: mp=163-164° C.; MS(m/e): 321 (M+1), 379 (M+59); Calculated for $C_{21}H_{24}N_2O$: Calcd: C, 78.72; H, 7.55; N, 8.74. Found: C, 78.63; H, 7.64; N, 8.78.

PREPARATION 23

6-Fluoro-5-methoxy-3-(1-methylpiperidin-4-yl)-1H-indole

A suspension of 6-fluoro-5-methoxy-3-(1-methyl-1,2,3,6-tetrahydropyridin-4-yl)-1H-indole (15.7 mmole, 4.09 g) in tetrahydrofuran (30 mL) at room temperature was added sodium borohydride (31.4 mmole, 1.19 g). To this suspension was carefully added acetic acid (47.1 mmole, 2.83 g). Severe frothing occurred during the addition. The reaction was stirred at room temperature for 1.0 hours. To the heavy suspension was added 5N hydrochloric acid (30 mL). The resulting solution was stirred at room temperature for 1.0 hour. Reaction was reduced in volume, cooled to 0° C. and the pH was adjusted to >12 with 50% wt/wt sodium hydroxide. The reaction was extracted with ethyl acetate (3×25 mL), organic phases were combined, dried over sodium sulfate, filtered and concentrated in vacuo to a solid. The resulting material was subjected to Waters LC2000 normal phase chromatography, eluting with a linear gradient of 0 to 10% methanol containing 1% ammonium hydroxide:chloroform over a thirty minute period collecting 150 mL fractions. Fractions containing the title compound were combined, reduced in volume and set aside. The resulting crystals were collected by filtration to afford 2.30 g (82%) of the title compound: mass spectrum (ion spray): m/z=263 (M+1); $^1$H NMR (DMSOd$_6$): 10.65 (s, 1H), 7.16 (d, 1H), 7.13 (d, 1H), 7.03 (d, 1H), 3.83 (s, 3H), 2.81 (m, 2H), 2.63 (m, 1H), 2.20 (s, 3H), 1.98 (m, 2H), 1.86 (m, 2H), 1.62 (m, 2H); Calculated for $C_{15}H_{19}FN_2O$: C, 68.21; H, 7.33; N, 6.66. Found: C, 68.09; H, 6.95; N, 10.52.

PREPARATION 24

5-Methoxy-7-methyl-3-(1-methylpiperidin-4-yl)-1H-indole

To a suspension of 5-methoxy-7-methyl-3-(1-methyl-1,2,3,6-tetrahydropyridin-4-yl)-1H-indole (0.1 mole, 24.71 g) in tetrahydrofuran (295 mL) at room temperature was added sodium borohydride (0.2 mole, 7.29 g). Trifluoroacetic acid (0.3 mole, 32.97 g) was added over a 15 minute period. The reaction was stirred at room temperature for 1.5 hours. To the heavy suspension was added 5N hydrochloric acid (200 mL). The resulting solution was stirred at room temperature for 1.5 hours. To the reaction was added ethyl acetate (500 mL) then the pH was adjusted to >12 with 50% wt/wt sodium hydroxide. The phases were separated and the aqueous phase was extracted with ethyl acetate (2×500 mL). The organic phases were combined, dried over sodium sulfate then filtered. The filtrate was filtered through a pad of silica (height of silica=7.0 cm) in a scinter glass funnel (inner diameter of funnel=14.5 cm). After the first fraction was collected the next two fractions were eluted with chloroform (1.2 L each). The remaining fractions were eluted with 90:10:1 chloroform:methanol:ammonium hydroxide (1.2 L fractions collected). The desired fractions were combined and concentrated in vacuo to afford 18.94 g (76%) of the title compound as a white solid: mass spectrum (ion spray): m/z=259 (M+1); $^1$H NMR (DMSOd$_6$): 7.02 (d, 1H), 6.81 (d, 1H), 6.53 (d, 1H), 3.74 (s, 3H), 2.84 (m, 2H), 2.62 (m, 1H), 2.39 (s, 3H), 2.23 (s, 3H), 2.06 (m, 2H), 1.90 (m, 2H), 1.67 (m, 2H).

PREPARATION 25

5-Methoxy-2-methyl-3-(1-methylpiperidin-4-yl)-1H-indole hydrochloride

5-Methoxy-2-methyl-3-(1-methyl-1,2,3,6-tetrahydropyridin-4-yl)-1H-indole (JOC 40, 2525 (1975), (6.1 g, 23.8 mmol) was reacted with hydrogen gas in the presence of Pt$_2$O (40° C./18 h/60 psi (413 kPa)) in an ethanol solution. After filtering the catalyst, the ethanol was evaporated to 5.92 g of solid foam. Flash chromatography [silica gel, dichloromethane/2N NH$_3$ (methanol) (90/10)] gave 5.4 g (88%) of the final product as a light yellow solid. Formation of the hydrochloride salt in EtOAc/MeOH provided the title compound as a white solid: mp=241° C.; ms(m/e): 259 (M+1); Calculated for $C_{16}H_{22}N_2O \cdot HCl$: C, 65.18; H, 7.86; N, 9.50. Found: C, 64.83; H, 7.54; N, 9.32.

PREPARATION 26

5-Benzyloxy-1-methyl-3-(1-methyl-1,2,3,6-tetrahydropyridin-4-yl)-1H-indole oxalate To a solution of 5-benzyloxy-3-(1-methyl-1,2,3,6-tetrahydropyridin-4-yl)-1H-indole 1 (1.16 g, 3.64 mmol) in DMF (20 mL) was added sodium hydride (160 mg, 4.0 mmol, 60% dispersion in mineral oil). The reaction was cooled to 5° C. on an ice bath and methyl iodide (294 μL, 4.7 mmol) was added dropwise. The reaction mixture was stirred at 5° C. for 1 h, quenched with water, and extracted with ethyl acetate. The ethyl acetate extracts were washed with water, brine, dried (Na$_2$SO$_4$), filtered and concentrated under reduced pressure to give 1.2 g of a yellow oil. The product was purified by flash chromatography (silica gel, 2% 2M ammonia in methanol/methylene chloride) to provide 1.0 g (83%) of green oil. The product was crystallized as the oxalic acid salt from ethyl acetate to give the title compound as a yellow powder: mp=184-187° C. dec; ms(m/e): 333 (M+1); Calculated for $C_{22}H_{24}N_2O \cdot C_2H_2O_4$: Calcd: C, 68.23; H, 6.20; N, 6.63. Found: C, 68.20; H, 6.53; N, 6.35.

PREPARATION 27

5-Methoxy-1,7-dimethyl-3-(1-methylpiperdin-4-yl)-1H-indole

By a method similar to Preparation 26, using 5-methoxy-7-methyl-3-(1-methylpiperidin-4-yl)-1H-indo (7.89 mmol, 2.04 g), iodomethane (7.89 mmol, 1.12 g, 0.491 mL), THF (140 mL), potassium hydride (7.89 mmol, 0.904 g), 18-crown-6 (0.79 mmol, 0.209 g) purification of the crude material was by Waters LC2000 eluting with a linear gradient of 2 to 10% 2M ammonia in methanol:methylene chloride. Fractions containing the title compound combined, concentrated in vacuo to afford 1.55 g (72%) of the title compound: mass spectrum (ion spray): m/z=273 (M+1); $^1$H NMR (DMSOd$_6$): 6.89 (s, 1H), 6.77 (d, J=2.20 Hz, 1H), 6.47 (d, J=1.46 Hz, 1H), 3.91 (s, 3H), 3.72 (s, 3H), 2.87-2.80 (m, 2H), 2.65-2.52 (m, 4H), 2.18 (s, 3H), 2.05-2.02 (m, 1H), 2.02-1.97 (m, 1H), 1.89-1.84 (m, 2H), 1.67-1.62 (m, 1H), 1.59-1.54 (m, 1H); Calculated for $C_{17}H_{24}N_2O \cdot 0.1\ H_2O$: C, 74.47; H, 8.90; N, 10.22. Found: C, 74.13; H, 8.53; N, 10.25.

PREPARATION 28

5-Methoxy-7-methyl-3-(1-methylpiperdin-4-yl)-1-phenethyl-1H-indole

By a method similar to Preparation 26, using 5-methoxy-7-methyl-3-(1-methylpiperidin-4-yl)-1H-indole (5.81 mmol, 1.50 g), 35% potassium hydride (5.81 mmol, 0.665 g), toluene-4-sulfonic acid phenethyl ester (5.81 mmole, 1.60 g), additional 18-crown-6 (5.22 mmol,1.38 g) and additional toluene-4-sulfonic acid phenethyl ester (2.90 mmole, 0.802 g) were added to afford 0.31 g (15%) of the title compound: mass spectrum (ion spray): m/z=363 (M+1).

PREPARATION 29

1-Benzyl-5-methoxy-7-methyl-3-(1-methylpiperdin-4-yl)-1H-indole

By a method similar to Preparation 26, using 5-methoxy-7-methyl-3-(1-methylpiperidin-4-yl)-1H-indole (5.81 mmol, 1.50 g) and benzyl bromide (5.81 mmol, 0.993 g), THF (100 mL), 35% potassium hydride (5.81 mmol, 0.665 g), and 18-crown-6 (0.58 mmol, 0.153 g) afforded 1.63 g (81%) of the title compound: mass spectrum (ion spray): m/z=349 (M+1): Calculated for $C_{23}H_{28}N_2O \cdot 0.3H_2O$: C, 78.06; H, 8.15; N, 7.92. Found: C, 78.13; H, 7.84; N, 8.03.

PREPARATION 30

1-Propyl-5-methoxy-7-methyl-3-(1-methylpiperdin-4-yl)-1H-indole

By a method similar to Preparation 26, using 5-methoxy-7-methyl-3-(1-methylpiperidin-4-yl)-1H-indole (5.81 mmole, 1.50 g), iodopropane (5.81 mmole, 0.987 g, 0.566 mL) in THF (100 mL), potassium hydride (5.81 mmole, 0.665 g), and 18-crown-6 (0.58 mmole, 0.153 g) afforded 1.26 g (72%) of the title compound: mass spectrum (ion spray): m/z=301 (M+1);. Calculated for $C_{19}H_{28}N_2O \cdot 0.3H_2O$: C, 74.61; H, 9.43; N, 9.16. Found: C, 74.37; H, 9.03; N, 9.01.

PREPARATION 31

1-Ethyl-5-methoxy-7-methyl-3-(1-methylpiperdin-4-yl)-1H-indole

By a method similar to Preparation 26, using 5-methoxy-7-methyl-3-(1-methylpiperidin-4-yl)-1H-indole (5.81 mmole, 1.5 g) in THF (100 mL), 35% potassium hydride (5.81 mmole, 0.665 g), 18-crown-6 (0.58 mmole, 0.153 g), and iodoethane (5.81 mmole, 0.906 g, 0.464 mL) afforded 1.17 g (70%) of the title compound: mass spectrum (ion spray): m/z=287 (M+1); Calculated for $C_{18}H_{26}N_2O \cdot 0.1 H_2O$: C, 75.01; H, 9.16; N, 9.72. Found: C, 75.10; H, 9.01; N, 9.79.

PREPARATION 32

1-phenethyl-3-(1-methylpiperidin-4-yl)-5-hydroxy-1H-indole

To solution of 5-(t-butyldimethylsilanyloxy)-3-(1-methylpiperidin-4-yl)-1H-indol (285 mg, 0.83 mmol) in tetrahydrofuran (20 mL) stirring at 0° C. was treated with potassium hydride (99 mg of a 35% dispersion in oil, 0.87 mmol). The light yellow solution was stirred for 20 minutes at 0° C. Phenethyl tosylate (2.29 g, 8.30 mmol) was added and stirred at 0° C. for 3 h, and at room temperature overnight. Addition 35% potassium hydride (94 mg, 0.83 mmol) was added and the reaction was stirred at room temperature overnight. The mixture was treated with tetrabutylammonium fluoride (830 μL of a 1M solution in tetrahydrofuran, 0.83 mmol) and was stirred overnight at room temperature, before concentrating in vacuo. Purification by silica gel chromatography 9:1 dichloromethane: methanol gave 175 mg (63%) of the title compound as orange foam: MS (APCI): m/e 335.2 (M+1).

PREPARATION 33

1-(4-Fluorobenzyl)-3-(1-methylpiperidin-4-yl)-5-hydroxy-1H-indole

By a method similar to Preparation 32, using 5-(t-butyldimethylsilanyloxy)-3-(1-methylpiperidin-4-yl)-1H-indol (400 mg, 1.16 mmol), potassium hydride (139 mg of a 35% dispersion oil, 1.21 mmol) and 4-fluorobenzyl bromide (148 μL, 1.21 mmol), and chromatographic purification with a 9:1 mixture of dichloromethane and methanol provided 353 mg (90%) of the desired compound as an orange foam: $^1$H NMR (dmso-$d_6$): 8.61 (s, 1H), 7.25-7.00 (m, 6H), 6.82 (d, 1H, J=2.0 Hz), 6.54 (dd, 1H, J=8.8, 1.6 Hz), 5.20 (s, 2H), 2.84 (br d, 2H, J=11.6 Hz), 2.62-2.50 (m, 1H), 2.19 (s, 3H), 2.01 (br t, 2H, J=11.0 Hz), 1.85 (br d, 2H, J=13.2 Hz), 1.62 (qd, 2H, J=12.0, 2.4 Hz). MS (APCI): m/e 339.2 (M+1).

PREPARATION 34

1-Benzyl-3-(1-methylpiperidin-4-yl)-5-hydroxy-1H-indole

By a method similar to Preparation 32, using 5-(t-butyldimethylsilanyloxy)-3-(1-methylpiperidin-4-yl)-1H-indol (350 mg, 1.02 mmol) in tetrahydrofuran (20 mL), potassium hydride (116 mg of a 35% dispersion in oil, 1.02 mmol) and benzyl bromide (121 μL, 1.02 mmol) and after stirring at room temperature overnight, the reaction mixture was directly treated with tetrabutyl ammonium fluoride (1.02 mL of a 1M solution in tetrahydrofuran, 1.02 mmol) and stirred at room temperature for three days. The solvent was then removed in vacuo, and the resulting residue was diluted with methanol (15 mL) and directly applied to a 5 g SCX column. After thoroughly washing with methanol, the column was eluted with a 8:2 mixture of dichloromethane and 2 N ammonia in methanol. The eluent was concentrated in vacuo, and the residue was further purified on silica gel. Elution with a 0% to 2% gradient of methanol in dichloromethane provided 323 mg (99%) of the title compound as an off-white gum: $^1$H NMR (400 MHz, $CDCl_3$): 7.33-7.20 (m, 4H), 7.12-7.05 (m, 2H), 7.04 (d, 1H, J=8.4 Hz), 6.82 (s, 1H), 6.70 (dd, 1H, J=8.6, 2.6 Hz), 5.17 (s, 2H), 3.01 (br d, 2H, J=11.2 Hz), 2.71 (tt, 1H, J=11.8, 4.0 Hz), 2.38 (s, 3H), 2.22-1.98 (m, 4H), 1.98-1.88 (m, 2H): MS (ES+): m/e 321.0 (M+1).

PREPARATION 35

6-Methoxy-1,2,3,4-tetrahydroquinoline

6-Methoxyquinoline (48 g, 0.30 mol) was dissolved in 500 mL methanol and mix with $PtO_2$ (12 g, 52.8 mmol), the mixture was put in a Parr shaker heated to 40° C. under hydrogen (40 psi (275 kPa)) for 24 h. The reaction was cool to room temperature, released the pressure, and then removed the catalyst. The solvent was concentrated resulting the title compound: $^1$H NMR (300 MHz, CDCl$_3$) 1.90-1.97 (m, 2), 2.75 (t, 2H, J=6.4 Hz), 3.25 (t, 2H, J=5.5 Hz), 3.72 (s, 3H), 6.44-6.60 (m, 3H). cl PREPARATION 36

8-Methoxy-5,6-dihydro-4H-pyrrolo[3,2,1-ij]quinoline-1,2-dione

A solution of 6-methoxy-1,2,3,4-tetrahydroquinoline (10 g, 61.3 mmol) 600 mL CH$_2$Cl$_2$ was slowly added to a solution of oxalyl chloride (8.4 mL, 94.5 mmol) in 100 mL CH$_2$Cl$_2$ at 0° C. After addition the reaction mixture was at 0° C. for 0.5 h, aluminum chloride (24.5 g, 184 mmol) was than added to the reaction mixture, the resulting mixture was warmed up to room temperature, stirred over night. The reaction mixture was poured on ice, diluted with 1N HCl, the aqueous layer was extracted with CHCl$_3$ (3×150 mL), the combined organic layers was washed with brine, dried over Na$_2$SO$_4$. The solvent was concentrated, the crude product was purified by flash chromatography (Hexane/EtOAc), obtained 10.0 g (75%) of pure title compound: $^1$H NMR (300 MHz, CDCl$_3$) 2.01-2.05 (m, 2H), 2.74 (t, 2H, J=6.0 Hz), 3.73 (t, 2H, J=5.8 Hz), 3.77 (s, 3H), 6.92-6.93 (m, 2H).

PREPARATION 37

8-Methoxy-5,6-dihydro-4H-pyrrolo[3,2,1-ij]quinoline

8-Methoxy-5,6-dihydro-4H-pyrrolo[3,2,1-ij]quinoline-1, 2-dione (3.0 g, 13.8 mmol), was added to BH$_3$-THF (1.0 M, 30 mL, 30 mmol) dropwise at 0° C. After addition the reaction mixture was stirred 0° C. for 5 h, then warmed to room temperature and stirred for 12 h. The reaction was quenched by adding 5N HCl cautiously at 0° C. at until no gas evolution to pH=8. The reaction mixture was diluted with water, extracted with ether, the combined organic layers were washed with brine, dried over Na$_2$SO$_4$. The solvate was removed in vacuo and purified by flash chromatography using hexanes/ethyl acetate (9:1). After purification, 1.3 g (50%) of title compound was obtained: $^1$H NMR (300 MHz, CDCl$_3$) 2.21-2.27 (m, 2H), 2.96 (t, 2H, J=6.1 Hz), 3.83 (s, 3H), 4.13 (t, 2H, J=5.8 Hz), 6.36 (d, 1H, J=2.8 Hz), 6.62 (d, 1H, J=1.4 Hz), 6.91 (d, 1H, J=2.2 Hz), 7.05 (d, 1H, J=2.7 Hz).

PREPARATION 38

8-Methoxy-1-(1-methyl-1,2,3,6-tetrahydropyridin-4-yl)-5,6-dihydro-4H-pyrrolo[3,2,1-ij]quinoline By a method similar to Preparation 11, using 8-methoxy-5,6-dihydro-4H-pyrrolo[3,2,1-ij]quinoline (0.28 g, 1.5 mmol), and N-methylpiperidone (Aldrich, 0.68 g, 6.0 mmol) 0.12 g (27%) of title compound was obtained: $^1$H NMR (300 MHz, CDCl$_3$): 2.18-22.24 (m, 2H), 2.77 (s, 3H), 2.89-2.97 (m, 4H), 3.21 (t, 2H, J=61 Hz), 3.68-3.49 (m, 2H), 3.85 (s, 3H), 4.10 (t, 2H, J=5.7 Hz), 6.02 (m, 1H), 6.65-6.66 (m, 1H), 7.04-7.06 (m, 2H); MS (ELECTROSPRAY): m/e 283.0 (M+1).

PREPARATION 39

Benzenesulfonic acid 7-bromo-1H-indol-5-yl ester

Combine 3-bromo-4-nitrophenol (1 eq.), triethylamine (1.1 eq.) and tert-butyldimethylsilyl chloride (1.1 eq.) in methylene chloride at 0° C. After about 6 hours, pour the reaction mixture into ethyl acetate, wash with brine, dry the organic layer over Na$_2$SO$_4$ and then concentrate. Purify to give 3-bromo-4-nitro-1-tert-butyldimethylsilyloxybenzene.

Combine 3-bromo-4-nitro-1-tert-butyldimethylsilyloxy-benzene and dry THF. Cool to about −45° C. and then treat with vinylmagnesium bromide (1.2 eq.) over a few minutes. After about 45 minutes, pour the reaction mixture into saturated aq. NH$_4$Cl, extract with ether, combined the organic extracts and extract with water, dry over Na$_2$SO$_4$ and concentrate. Purify to give 7-bromo-5-(tert-butyldimethyl-silanyloxy)-1H-indole.

Combine 7-bromo-5-(tert-butyldimethylsilanyloxy)-1H-indole and methylene chloride and treat with tetrabutyl ammonium fluoride (1.0 eq.) at 0° C. After the mixture is stirred for about 1 hour, pour into ethyl acetate, wash with brine, dry the organic layer over Na$_2$SO$_4$ and concentrate. Purify to give 7-bromo-5-hydroxy-1H-indole.

Alternately, 7-bromo-5-hydroxy-1H-indole is prepared by the method of Kita et al, Heterocycles, 1992, 33 (2), 503-506).

Combine 7-bromo-5-hydroxy-1H-indole and 0.2 N NaOH (1.1 eq.) in THF. Cool to about 0° C. before adding benzenesulfonyl chloride (1.10 eq.). Allow the reaction mixture to warm to ambient temperature. After 8 hours, pour into ethyl acetate, wash with water, dry the organic layer over Na$_2$SO$_4$ and concentrate. Purify to give the title compound.

EXAMPLE 1

Benzenesulfonic acid 3-(1-methyl-1,2,3,6-tetrahydropyridin-4-yl)-1-propyl-1H-indol-5-yl ester hydrochloride

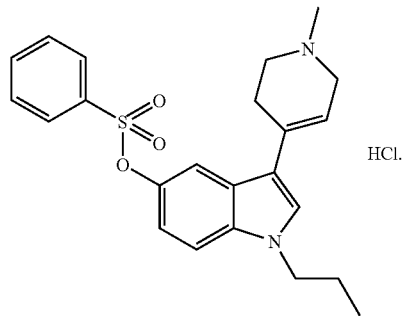

To a solution of benzenesulfonic acid 3-(1-methyl-1,2,3, 6-tetrahydropyridin-4-yl)-1H-indol-5-yl ester, from Example 46, (0.2 g, 0.54 mmol) in dimethylformamide (25 mL) at 0° C. under nitrogen was added sodium hydride in one portion (24.0 mg of a 60% dispersion in oil, 0.60 mmol). The light green mixture was stirred for 30 minutes at 0° C. and 1-propyl bromide (54 mL, 0.60 mmol) was added. After completion of the reaction, the reaction was quenched with water, extracted with ethyl acetate (2×125 mL), dried over magnesium sulfate, filtered, concentrated in vacuo to a residue that was purified on silica gel using 9:1 dichloromethane:methanol as the solvent to afford 58 mg (59%) of the title compound as an orange oil. The oil was dissolved in methanol (10 mL) and treated with ammonium chloride (11.8 mg, 0.22 mmol, dissolved in 10 mL methanol). The resulting solution was concentrated in vacuo, and triturated in a minimal amount of diethyl ether. Filtration and drying of the precipitate afforded 58 mg(59%) of the title compound as a yellow solid: mp=170-174° C.; MS (ES+): m/e 411.2 (M+1); $^1$H NMR (400 MHz, CDCl$_3$,): 7.86-7.78 (m, 2H), 7.66-7.58 (m, 1H), 7.52-7.44 (m, 2H), 7.27-7.40 (m, 1H), 7.13 (d, 1H, J=8.8 Hz), 7.04 (s, 1H), 6.81 (dd, 1H, J=8.8, 2.4 Hz), 5.71 (br s, 1H), 3.95 (t, 2H, J=6.8 Hz), 3.08-3.03 (m, 2H), 2.63 (t, 2H, J=6.0 Hz), 2.52-2.45 (m 2H), 2.38 (s, 3H), 1.78 (sextuplet, 2H, J=7.2 Hz), 0.87 (t, 3H, J=7.6 Hz; Calculated for C$_{23}$H$_{26}$N$_2$O$_3$S.HCl 2.1H$_2$0: C 56.93, H 5.56, N 5.77; Found: C 57.20, H 5.27, N 5.35.

EXAMPLE 2

Benzenesulfonic acid 1-benzyl-3-(1-methylpiperidin-4-yl)-1H-indol-5-yl ester hydrochloride

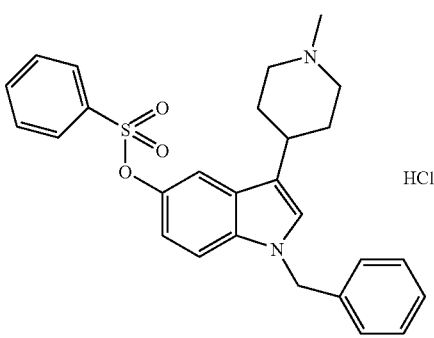

By a method similar to Example 1, using benzenesulfonic acid 3-(1-methylpiperidin-4-yl)-1H-indol-5-yl ester, from Example 34 or 45, (200 mg, 0.54 mmol), benzyl bromide (64 μL, 0.54 mmol) dimethylformamide (15 mL) and sodium hydride in one portion (22 mg of a 60% dispersion in oil, 0.54 mmol) gave 198 mg (80%) of the free base of the title compound as a gold-colored oil. The oil was dissolved in methanol (10 mL) and treated with ammonium chloride (46.0 mg, 0.86 mmol, dissolved in 10 mL methanol). The solution was concentrated in vacuo, and the resulting solid was triturated with a minimal amount of diethyl ether. Filtration and drying of the precipitate afforded 210 mg (98%) of the title hydrochloride as an off-white solid: mp=227-230° C.; $^1$H NMR (400 MHz, dmso-d$_6$): δ 10.41 (br s, 1H), 7.86-7.72 (m, 3H), 7.65-7.55 (m, 2H), 7.38 (s, 1H), 7.37 (d, 1H, J=8.8 Hz), 7.30-7.10 (m, 6H), 6.68 (br d, 1H, J=8.8 Hz), 5.31 (s, 2H), 3.42 (br d, 2H, J=11.6 Hz), 3.10-2.95 (m, 2H), 2.94-2.80 (m, 1H), 2.74 (s, 3H), 2.00-1.80 (m, 4H); MS (APCI): m/e 461.0 (M+1); Calculated (for C$_{27}$H$_{28}$N$_2$O$_3$S.HCl.0.6H$_2$0): C 63.85, H 5.99, N 5.51, Cl 7.13; Found: C 63.96, H 5.78, N 5.59, Cl 7.11.

EXAMPLE 3

2,6-Difluorobenzenesulfonic acid 1-propyl-3-(1-methylpiperidin-4-yl)-1H-indol-5-yl ester oxalate

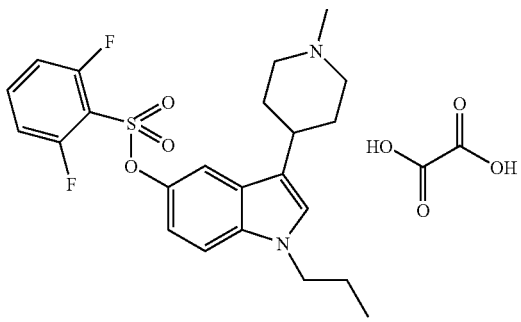

By a method similar to Example 1, using 2,6-difluorobenzenesulfonic acid 3-(1-methylpiperidin-4-yl)-1H-indol-5-yl ester, from Example 42 or 47, (175 mg) dimethylformamide (25 mL), sodium hydride (19 mg of a 60% dispersion in oil, 0.47 mmol) and 1-bromopropane (43 mL, 0.47 mmol) gave 66 mg (34%) of the free base of the title compound as a gold oil. The oil was dissolved in ethyl acetate (10 mL) and treated with oxalic acid (13.2 mg, 0.15 mmol, dissolved in 10 mL of ethyl acetate). An off-white precipitate formed immediately, which was filtered and dried to provide 70 mg (89%) of the title compound as an off white solid: mp=185-189° C.; MS (ES+): m/e 449 (M+1); $^1$H NMR (400 MHz, dmso-d$_6$): 7.94-7.82 (m, 1H), 7.43 (d, 1H, J=8.8 Hz), 7.37 (t, 2H, J=8.8 Hz), 7.29 (d, 1H, J=2.4 Hz), 7.28 (s, 1H), 6.78 (dd, 1H, J=9.0, 2.2 Hz), 4.03 (t, 2H, J=7.2 Hz), 3.35 (br d, 2H, J=12.0 Hz), 3.02-2.80 (m, 3H), 2.70 (s, 3H), 2.00-1.88 (m, 2H), 1.84-1.68 (m, 2H), 1.68 (sextuplet, 2H, J=6.8 Hz), 0.77 (t, 3H, J=6.8 Hz); Calculated (for C$_{23}$H$_{26}$F$_2$N$_2$O$_3$S.C$_2$H$_2$O$_4$): C 55.75, H 5.24, N 5.20; Found: C 55.63, H 5.17, N 5.13.

EXAMPLE 4

Benzenesulfonic acid 1-ethyl-3-(1-methylpiperidin-4-yl)-1H-indol-5-yl ester oxalate

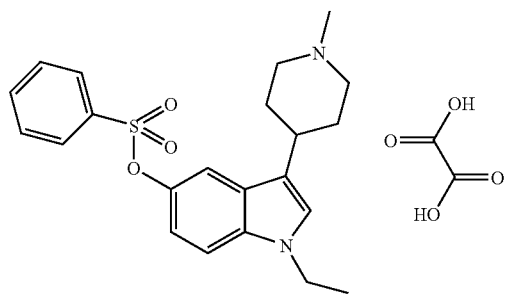

By a method similar to Example 1, using benzenesulfonic acid 3-(1-methylpiperidin-4-yl)-1-H-indol-5-yl ester, from Example 34 or 45, (350 mg, 0.94 mmol), dimethylformamide (20 mL), sodium hydride (42 mg of a 60% dispersion in oil, 1.0 mmol) and ethyl iodide (76 mL, 0.94 mmol) provided 265 mg (70%) of the free base of the desired compound as a golden oil. The oil was dissolved in ethyl acetate (10 mL) and treated with oxalic acid (59.8 mg, 0.66 mmol), dissolved in 10 mL of ethyl acetate), upon which a precipitate formed immediately. Filtration and drying of the precipitate provided 235 mg (72%) of the title oxalate as an off-white solid: mp=127-130° C.; $^1$H NMR (400 MHz, dmso-d$_6$): 7.84-7.74 (m, 3H), 7.66-7.58 (m, 2H), 7.37 (d, 1H, J=8.8 Hz), 7.26 (s, 1H), 7.14 (d, 1H, J=2.0 Hz), 6.68 (dd, 1H, J=8.8, 2.4 Hz), 4.09 (q, 2H, J=7.2 Hz), 3.39 (br d, 2H, J=11.2 Hz), 2.98 (br t, 2H, J=11.4 Hz), 2.90-2.78 (m, 1H), 2.73 (s, 3H), 1.98-1.88 (m, 2H), 1.84-1.70 (m, 2H), 1.27 (t, 3H, J=7.2 Hz); MS (ES+): m/e 399.1 (M+1); Calculated (for $C_{22}H_{26}N_2O_3S \cdot C_2H_2O_4 \cdot 0.6H_2O$): C 57.72, H 5.89, N 5.60; Found: C 57.65, H 5.75, N 5.96.

EXAMPLE 5

Benzenesulfonic acid 1-propyl-3-(1-methylpiperidin-4-yl)-1H-indol-5-yl ester hydrochloride

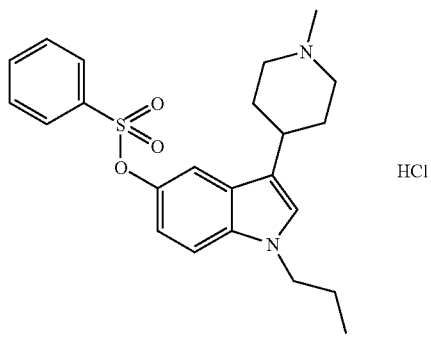

By a method similar to Example 1, using benzenesulfonic acid 3-(1-methyl-pyridin-4-yl)-1H-indol-5-yl ester, from Example 34 or 45, (0.25 g, 0.67 mmol) in tetrahydrofuran (20 mL), sodium hydride (30.0 mg of a 60% dispersion in oil, 0.74 mmol), 1-propyl bromide (67 mL, 0.74 mmol) provided 182 mg (65%) of the desired benzenesulfonic acid 3-(1-methyl-pyridin-4-yl)-1-propyl-1H-indol-5-yl ester free base as a gold oil. The oil was dissolved in methanol (10 mL), treated with ammonium chloride (23.3 mg, 0.44 mmol), and dissolved in 10 mL methanol. The resulting solution was concentrated in vacuo, and triturated in a minimal amount of diethyl ether. Filtration followed by drying of the resulting precipitate afforded 180 mg (90%) of the title hydrochloride as a tan solid: mp=194-197° C.; MS (ES+) m/e 413.1 (M+1); $^1$H NMR (400 MHz, dmso-d$_6$): 7.84-7.74 (m, 3H), 7.66-7.58 (m, 2H), 7.36 (d, 1H, J=8.8 Hz), 7.15 (br s, 1H), 6.90 (d, 1H, J=2.0 Hz), 6.72 (dd, 1H, J=8.8, 2.2 Hz), 3.99 (t, 2H, J=7.0 Hz), 2.78 (br d, 2H, J=11.6 Hz), 2.52-2.40 (m, 1H), 2.16 (s, 3H), 1.92 (br t, 2H, J=10.8 Hz), 1.74-1.60 (m, 4H), 1.58-1.40 (m, 2H), 0.77 (t, 3H, J=7.4 Hz); Calculated (for $C_{23}H_{28}N_2O_3S \cdot HCl \cdot 1.15H_2O$): C 58.81, H 6.71, N 5.96; found: C 58.64, H 6.31, N 6.36.

EXAMPLE 6

Benzenesulfonic acid 1-methyl-3-(1-methylpiperidin-4-yl)-1H-indol-5-yl ester oxalate

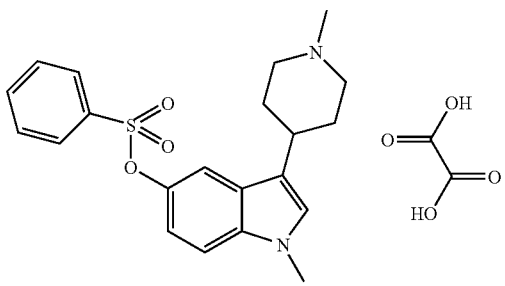

By a method similar to Example 1, using benzenesulfonic acid 3-(1-methylpiperidin-4-yl)-1H-indol-5-yl ester, from Example 34 or 45, (300 mg, 0.81 mmol) in tetrahydrofuran (20 mL) potassium hydride (100 mg of a 35% dispersion in oil, 0.88 mmol), methyl iodide (50 mL, 0.81 mmol), 18-crown-6 ether (30 mg, 0.11 mmol) provided 246 mg (79%) of the free base of the desired product as an off-white gum. The gum was dissolved in ethyl acetate (10 mL) and treated with oxalic acid (57.5 mg, 0.64 mmol, dissolved in 10 mL ethyl acetate), upon which a precipitate formed immediately. Filtration and drying of the precipitate provided 286 mg (94%) of the title oxalate as a white solid: mp=135-142° C.; $^1$H NMR (400 MHz, dmso-d$_6$): 7.82-7.73 (m, 3H), 7.65-7.57 (m, 2H), 7.31 (d, 1H, J=8.8 Hz), 7.19 (br s, 1H), 7.14 (d, 1H, J=2.0 Hz), 6.68 (dd, 1H, J=8.8, 2.4 Hz), 3.67 (s, 3H), 3.39 (br d, 2H, J=12.4 Hz), 2.98 (br t, 2H, J=12.0 Hz), 2.91-2.79 (m, 1H), 2.73 (s, 3H), 1.98-1.86 (m, 2H), 1.84-1.68 (m, 2H). MS (ES+): m/e 385.0 (M+1); Calculated (for $C_{21}H_{24}N_2O_3S \cdot C_2H_2O_4 \cdot 0.6H_2O$): C 56.91, H 5.64, N 5.77; Found: C 56.89, H 5.32, N 5.42.

EXAMPLE 7

2,6-Difluorobenzenesulfonic acid 1-ethyl-3-(1-methylpiperidin-4-yl)-1H-indol-5-yl ester oxalate

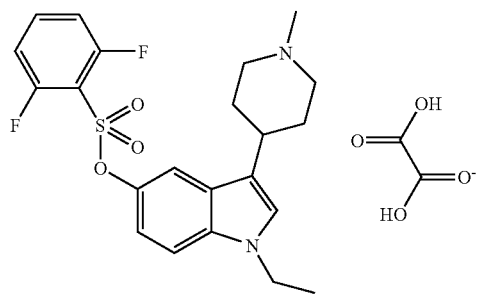

By a method similar to Example 1, using 2,6-difluorobenzenesulfonic acid 3-(1-methylpiperidin-4-yl)-1H-indol-5-yl ester, from Example 42 or 47, (425 mg, 1.05 mmol), tetrahydrofuran (20 mL), potassium hydride (120 mg of a 35% dispersion in oil, 1.05 mmol), ethyl iodide (84 mL, 1.05 mmol) and 18-crown-6 ether (40 mg, 0.15 mmol) provided 274 mg (60%) of the free base of the desired product as a colorless film. The film was dissolved in ethyl acetate (10 mL) and treated with oxalic acid (17.1 mg, 0.63 mmol, dissolved in 10 mL ethyl acetate), upon which a precipitate formed immediately. Filtration and drying of the precipitate provided 297 mg (90%) of the title oxalate as an off-white solid: mp=161-165° C.; $^1$H NMR (400 MHz, dmso-d$_6$): 7.93-7.83 (m, 1H), 7.43 (d, 1H, J=9.6 Hz), 7.37 (t, 2H, J=8.8 Hz), 7.29 (s, 1H), 7.28 (d, 1H, J=2.4 Hz), 6.80 (dd, 1H, J=8.8, 2.0 Hz), 4.10 (q, 2H, J=7.2 Hz), 3.36 (br d, 2H, J=11.6 Hz), 3.02-2.90 (m, 2H), 2.92-2.83 (m, 1H), 2.70 (s, 3H), 2.00-1.88 (m, 2H), 1.85-1.70 (m, 2H), 1.27 (t, 3H, J=7.2 Hz). MS (ES+): m/e 435.1 (M+1); Calculated (for C$_{22}$H$_{24}$F$_2$N$_2$O$_3$S.0.9C$_2$H$_2$O$_4$.0.1H$_2$O): C 55.26, H, 5.07, N 5.42; Found: C 55.44, H 4.94, N 5.50.

EXAMPLE 8

2,6-Difluorobenzenesulfonic acid 1-benzyl-3-(1-methylpiperidin-4-yl)-1H-indol-5-yl ester oxalate

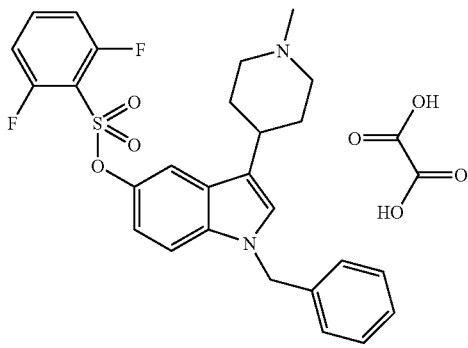

By a method similar to Example 1, using 2,6-difluorobenzenesulfonic acid 3-(1-methylpiperidin-4-yl)-1H-indol-5-yl ester, from Example 42 or 47, (250 mg, 0.62 mmol), tetrahydrofuran (20 mL), potassium hydride (77 mg of a 35% dispersion in oil, 0.68 mmol) benzyl bromide (73 mL, 0.62 mmol) and 18-crown-6 ether (25 mg, 0.09 mmol) provided 100 mg (30%) of the free base of the desired product as a colorless film. The film was dissolved in ethyl acetate (10 mL) and treated with oxalic acid (18.1 mg, 0.20 mmol, dissolved in 10 mL ethyl acetate), upon which a precipitate formed immediately. Filtration and drying of the precipitate provided 107 mg (90%) of the title oxalate as a tan solid: mp 205-208° C.; $^1$H NMR (400 MHz, dmso-d$_6$): 7.92-7.82 (m, 1H), 7.47-7.30 (m, 5H), 7.30-7.10 (m, 5H), 6.77 (dd, 1H, J=8.8, 1.6 Hz), 5.32 (s, 2H), 3.39 (br d, 2H, J=12.0 Hz), 3.06-2.86 (m, 3H), 2.72 (s, 3H), 2.02-1.92 (m, 2H), 1.86-1.70 (m, 2H). MS (ES+): m/e 497.0 (M+1). MS (ES): m/e 435.1 (M+1); Calculated (for C$_{27}$H$_{26}$F$_2$N$_2$O$_3$S.C$_2$H$_2$O$_4$): C 59.38, H 4.81, N 4.78; Found: C 59.03, H 4.93, N 4.55.

EXAMPLE 9

Benzenesulfonic acid 1-phenethyl-3-(1-methylpiperidin-4-yl)-1H-indol-5-yl ester oxalate

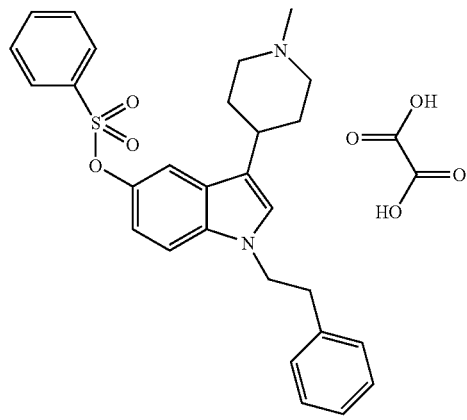

By a method similar to Example 1, using benzenesulfonic acid 3-(1-methylpiperidin-4-yl)-1H-indol-5-yl ester, from Example 42 or 47, (300 mg, 0.81 mmol), tetrahydrofuran (20 mL), potassium hydride (102 mg of a 35% dispersion in oil, 0.89 mmol) and toluene-4-sulfonic acid phenethyl ester (447 mg, 1.62 mmol) provided 132 mg (34%) of the free base of the desired product as a colorless oil. The oil was dissolved in ethyl acetate (10 mL) and treated with oxalic acid (25.0 mg, 0.28 mmol, dissolved in 10 mL ethyl acetate upon which a precipitate formed immediately. Filtration and drying of the precipitate provided 150 mg (96%) of the title oxalate as a white solid: mp=208-212° C.; $^1$H NMR (400 MHz, dmso-d$_6$): 7.84-7.74 (m, 3H), 7.66-7.58 (m, 2H), 7.38 (d, 1H, J=9.2 Hz), 7.24-7.08 (m, 7H), 6.65 (dd, 1H, J=9.0, 2.2 Hz), 4.27 (t, 2H, J=7.6 Hz), 3.42-3.30 (m, 2H), 3.04-2.88 (m, 4H), 2.88-2.76 (m, 1H), 2.71 (s, 3H), 1.94-1.83 (m, 2H), 1.80-1.63 (m, 2H); MS (ES+): m/e 475.1 (M+1); Calculated (for C$_{28}$H$_{30}$N$_2$O$_3$S.C$_2$H$_2$O$_4$.0.4H$_2$O): C 63.00, H 5.78, N 4.89; Found: C 63.09, H 5.64, N 4.86.

EXAMPLE 10

Benzenesulfonic acid 1-(3-phenylpropyl)-3-(1-methylpiperidin-4-yl)-1H-indol-5-yl ester oxalate

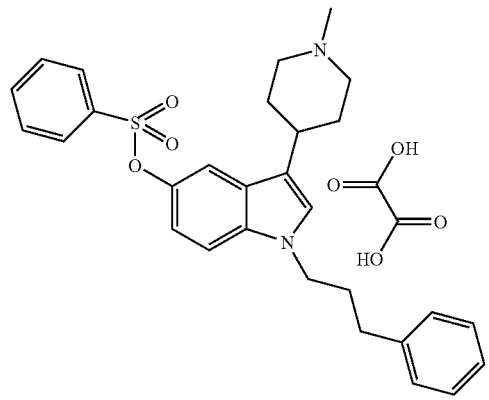

By a method similar to Example 1, using benzenesulfonic acid 3-(1-methylpiperidin-4-yl)-1H-indol-5-yl ester, from Example 34 or 45, (250 mg, 0.67 mmol), tetrahydrofuran (20 mL), potassium hydride (77 mg of a 35% dispersion in oil, 0.67 mmol), 1-bromo-3-phenylpropane (113 mL, 0.74 mmol) provided 105 mg (32%) of the free base of the desired product as a colorless oil. The oil was dissolved in ethyl acetate (1.0 mL) and treated with oxalic acid (19.3 mg, 0.21 mmol, dissolved in 10 mL ethyl acetate), upon which a precipitate formed immediately. Filtration and drying of the precipitate provided 110 mg (88%) of the title oxalate as a white solid: mp=188-191° C.; $^1$H NMR (400 MHz, dmso-$d_6$): 7.84-7.74 (m, 3H), 7.62 (br t, 2H, J=7.8 Hz), 7.33 (d, 1H, J=8.8 Hz), 7.29-7.19 (m, 3H), 7.19-7.08 (m, 4H), 6.67 (dd, 1H, J=8.8, 1.6 Hz), 4.08 (t, 2H, J=7.4 Hz), 3.50-3.34 (m, 2H), 3.10-2.94 (m, 2H), 2.92-2.80 (m, 1H), 2.76 (s, 3H), 2.54-2.44 (m, 2H), 2.06-1.88 (m, 4H), 1.86-1.72 (m, 2H); MS (ES+): m/e 475.1 (M+1). MS (ES+): m/e 489.0 (M+1); Calculated (for $C_{29}H_{32}N_2O_3S \cdot C_2H_2O_4$): C 64.34, H 5.92, N 4.84; found: C 64.23, H 5.78, N 5.01.

EXAMPLE 11

Benzenesulfonic acid 1-(propylsulfonyl)-3-(1-methylpiperidin-4-yl)-1H-indol-5-yl ester oxalate

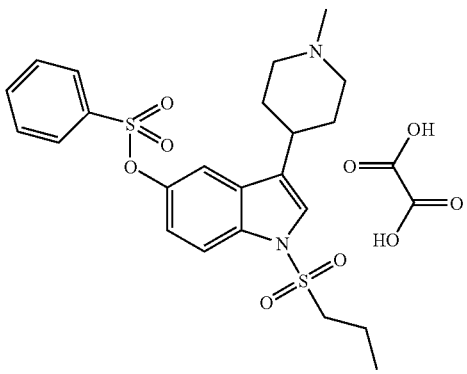

By a method similar to Example 1, using benzenesulfonic acid 3-(1-methylpiperidin-4-yl)-1H-indol-5-yl ester, from Example 34 or 45, (200 mg, 0.54 mmol), tetrahydrofuran (5 mL), potassium hydride (68 mg of a 35% dispersion in oil, 0.60 mmol) and 1-propanesulfonyl chloride (121 mL, 1.08 mmol) provided 67 mg (26%) of the free base of the desired compound as a tan gum. The gum was dissolved in ethyl acetate (10 mL) and treated with oxalic acid (12.6 mg, 0.14 mmol, dissolved in 10 ml ethyl acetate), upon which formation of precipitate was observed. Filtration and drying of the precipitate afforded 72 mg (89%) of the title oxalate as a tan solid: mp=139-142° C.; $^1$H NMR (400 MHz, dmso-$d_6$): 7.88-7.73 (m, 4H), 7.63 (t, 2H, J=7.8 Hz), 7.42 (s, 1H), 7.35 (d, 1H, J=2.4 Hz), 6.98 (dd, 1H, J=9.0, 2.2 Hz), 3.54 (t, 2H, J=7.2 Hz), 3.38 (br d, 2H, J=10.8 Hz), 3.04-2.84 (m, 3H), 2.72 (s, 3H), 2.00-1.88 (m 2H), 1.86-1.72 (m, 2H), 1.48 (sextuplet, 2H, J=7.2 Hz), 0.80 (t, 3H, J=7.2 Hz); MS (ES+): m/e 477.0 (M+1); Calculated (for $C_{23}H_{28}N_2O_5S_2 \cdot C_2H_2O_4$): C 52.99, H 5.34, N 4.94; found: C 53.20, H 5.33, N 4.89.

EXAMPLE 12

Benzenesulfonic acid 1-(isopropylsulfonyl)-3-(1-methylpiperidin-4-yl)-1H-indol-5-yl ester oxalate

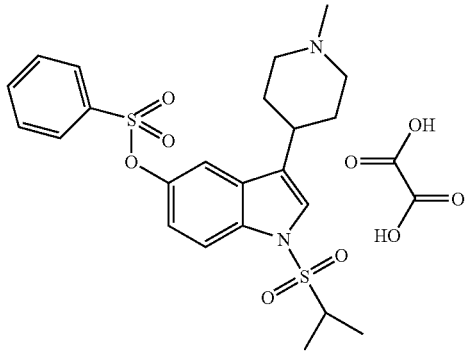

By a method similar to Example 1, using benzenesulfonic acid 3-(1-methylpiperidin-4-yl)-1H-indol-5-yl ester, from Example 34 or 45, (200 mg, 0.54 mmol), tetrahydrofuran (5 mL), potassium hydride (68 mg of a 35% dispersion in oil, 0.60 mmol), isopropylsulfonyl chloride (121 mL, 1.08 mmol) provided 76 mg (30%) of the free base of the desired compound as a tan gum. This gum was converted to 82 mg (91%) of the title oxalate, isolated as a white solid: mp=134-138° C. $^1$H NMR (400 MHz, dmso-$d_6$,): 7.86-7.73 (m, 4H), 7.67-7.60 (m, 2H), 7.42 (s, 1H), 7.35 (d, 1H, J=2.4 Hz), 6.97 (dd, 1H, J=9.0, 2.2 Hz), 3.75 (septuplet, 1H, J=7.2 Hz), 3.35 (br d, 2H, J=12.4 Hz), 3.00-2.84 (m, 3H), 2.70 (s, 3H), 1.98-1.87 (m 2H), 1.87-1.70 (m, 2H), 1.13 (d, 6H, J=6.8 Hz); MS (ES+): m/e 477.0 (M+1); Calculated (for $C_{23}H_{28}N_2O_5S_2 \cdot C_2H_2O_4$): C 52.99, H 5.34, N 4.94; found: C 53.16, H 5.20, N 4.86.

EXAMPLE 13

Benzenesulfonic acid 1-ethylsulfonyl-3-(1-methylpiperidin-4-yl)-1H-indol-5-yl ester oxalate

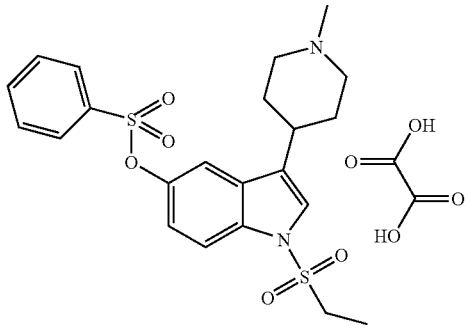

By a method similar to Example 1, using benzenesulfonic acid 3-(1-methylpiperidin-4-yl)-1H-indol-5-yl ester, from Example 34 or 45, (200 mg, 0.54 mmol), tetrahydrofuran (5 mL), potassium hydride (68 mg of a 35% dispersion in oil, 0.60 mmol), ethylsulfonyl chloride (102 mL, 1.08 mmol) provided 230 mg (92%) of the free base of the desired compound as a colorless gum. This gum was converted to 248 mg (90%) of the title oxalate, isolated as an off-white solid: mp 121-126° C.; $^1$H NMR (400 MHz, dmso-$d_6$,): 7.88-7.73 (m, 4H), 7.64 (t, 2H, J=7.8 Hz), 7.43 (s, 1H), 7.36 (d, 1H, J=2.4 Hz), 6.98 (dd, 1H, J=8.8, 2.4 Hz), 3.58 (q, 2H, J=7.2 Hz), 3.38 (br d, 2H, J=11.6 Hz), 3.04-2.86 (m, 3H), 2.72 (s, 3H), 2.00-1.90 (m 2H), 1.88-1.74 (m, 2H), 1.01 (t,

EXAMPLE 14

Benzenesulfonic acid 1-methylsulfonyl-3-(1-methylpiperidin-4-yl)-1H-indol-5-yl ester oxalate

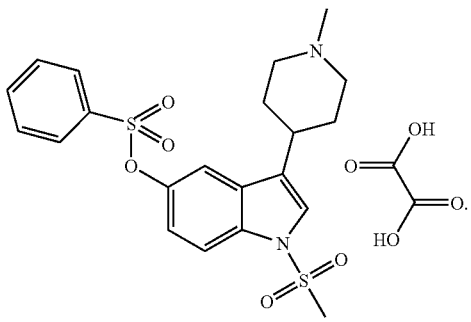

By a method similar to Example 1, using benzenesulfonic acid 3-(1-methylpiperidin-4-yl)-1H-indol-5-yl ester, from example 34 or 45, (200 mg, 0.54 mmol), tetrahydrofuran (5 mL), potassium hydride (68 mg of a 35% dispersion in oil, 0.60 mmol), methylsulfonyl chloride (42 mL, 0.54 mmol) provided 37 mg (15%) of the free base of the desired compound as a colorless gum. This gum was converted to 38 mg (86%) of the title oxalate, isolated as an off-white solid: mp=95-99° C. $^1$H NMR (400 MHz, dmso-d$_6$,): 7.88-7.74 (m, 4H), 7.64 (t, 2H, J=7.8 Hz), 7.41 (s, 1H), 7.33 (d, 1H, J=2.8 Hz), 7.00 (dd, 1H, J=9.0, 2.2 Hz). 3.46-3.36 (m, 2H), 3.43 (s, 3H), 3.00 (br t, 2H, J=11.4 Hz), 2.91 (br t, 2H, J=11.4 Hz), 2.74 (s, 3H), 2.00-1.90 (m 2H), 1.90-1.76 (m, 2H); MS (ES+): m/e 449.0 (M+1); MS (APCI): m/e 449.1 (m+1); Calculated for C$_{21}$H$_{24}$N$_2$O$_5$S$_2$.C$_2$H$_2$O$_4$.0.5H$_2$0: calcd: C, 50.44; H, 4.97; N, 5.11; found: C, 50.47; H, 4.66; N, 4.97.

EXAMPLE 15

Benzenesulfonic acid 1-benzylsulfonyl-3-(1-methylpiperidin-4-yl)-1H-indol-5-yl ester oxalate

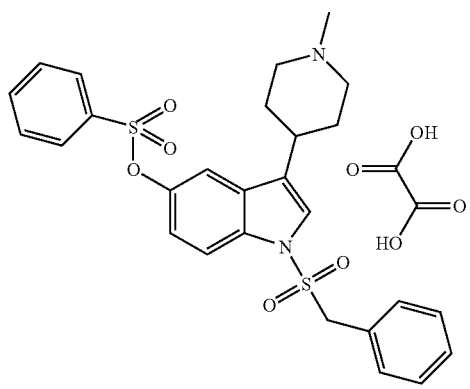

By a method similar to Example 1, using benzenesulfonic acid 3-(1-methylpiperidin-4-yl)-1H-indol-5-yl ester, from example 34 or 45, (200 mg, 0.54 mmol), tetrahydrofuran (5 mL), potassium hydride (68 mg of a 35% dispersion in oil, 0.60 mmol), α-toluenesulfonyl chloride (225 mg, 1.08 mmol) provided 30 mg (10%) of the free base of the desired compound as a tan gum. This gum was converted to 30 mg (85%) of the title oxalate, isolated as an off-white solid: mp=120-124° C.; $^1$H NMR (400 MHz, dmso-d$_6$,): 7.86-7.77 (m, 3H), 7.65 (t, 2H, J=7.6 Hz), 7.48 (d, 1H, J=9.2 Hz), 7.28 (br s, 1H), 7.21 (d, 1H, J=7.6 Hz), 7.09 (t, 2H, J=7.6 Hz), 7.00 (br s, 1H), 6.88-6.80 (m, 3H), 4.95 (s, 2H), 3.50-3.30 (m, 2H), 3.10-2.90 (m, 2H), 2.90-2.75 (m, 1H), 2.74 (s, 3H), 1.90-1.78 (m 2H), 1.78-1.62 (m, 2H); MS (ES+): m/e 525.0 (M+1);

Calculated (for C$_{27}$H$_{28}$N$_2$O$_5$S$_2$.C$_2$H$_2$O$_4$): C 56.67, H 4.92, N 4.56; found: C 56.71, H 4.88, N 4.35.

EXAMPLE 16

Benzenesulfonic acid 1-(naphth-1-ylsulfonyl)-3-(1-methylpiperidin-4-yl)-1H-indol-5-yl ester oxalate

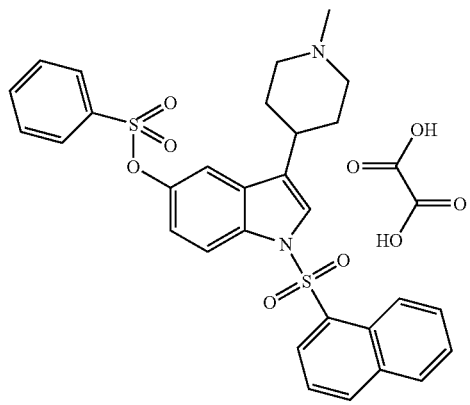

By a method similar to Example 1, using benzenesulfonic acid 3-(1-methylpiperidin-4-yl)-1H-indol-5-yl ester, from example 34 or 45, (200 mg, 0.54 mmol), tetrahydrofuran (5 mL), potassium hydride (68 mg of a 35% dispersion in oil, 0.60 mmol), naphth-1-ylsulfonyl chloride (245 mg, 1.08 mmol) provided 86 mg (28%) of the free base of the desired compound as a tan gum. This gum was converted to 92 mg (92%) of the title oxalate, isolated as a tan solid: mp=121-125° C.; $^1$H NMR (400 MHz, dmso-d$_6$,): 8.59 (d, 1H, J=8.0 Hz), 8.39 (d, 1H, J=7.2 Hz), 8.30 (d, 1H, J=7.6 Hz), 8.06 (d, 1H, J=8.4 Hz), 7.99 (s, 1H), 7.82-7.52 (m, 9H), 7.27 (d, 1H, J=2.0 Hz), 6.83 (dd, 1H, J=9.0, 2.2 Hz), 3.48-3.30 (m, 2H), 3.07-2.80 (m, 3H), 2.75 (s, 3H), 1.95-1.70 (m, 4H); MS (APCI): m/e 561.1 (M+1); Calculated (for C$_{30}$H$_{28}$N$_2$O$_5$S$_2$.C$_2$H$_2$O$_4$.0.7H$_2$O): C 57.94, H 4.77, N 4.22; found: 57.98, H 4.45, N 4.01.

EXAMPLE 17

Benzenesulfonic acid 1-butyl-3-(1-methylpiperidin-4-yl)-1H-indol-5-yl ester oxalate

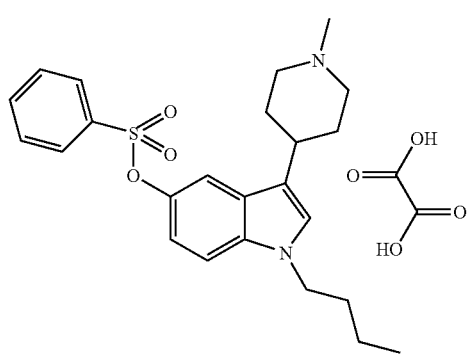

By a method similar to Example 1, using benzenesulfonic acid 3-(1-methylpiperidin-4-yl)-1H-indol-5-yl ester, from example 34 or 45, (0.50 g, 1.35 mmol), tetrahydrofuran (20 mL) potassium hydride (161 mg of a 35% dispersion in oil, 1.42 mmol) and 1-iodobutane (161 mL, 1.42 mmol) provided 305 mg (53%) of the free base of the desired product as a golden oil. The oil was dissolved in ethyl acetate (10 mL) and treated with oxalic acid (64.3 mg, 0.71 mmol, dissolved in 10 mL ethyl acetate), upon which a precipitate formed immediately. Filtration and drying of the precipitate provided 315 mg (85%) of the title oxalate as an off-white solid: mp=193-198° C.; MS (APCI): m/e 427.2 (M+1); $^1$H NMR (400 MHz, dmso-$d_6$): 7.84-7.74 (m, 3H), 7.62 (t, 2H, J=7.4 Hz), 7.37 (d, 1H, J=8.8 Hz), 7.23 (s, 1H), 7.13 (br s, 1H), 6.68 (br d, 1H, J=8.8), 4.04 (t, 2H, J=7.0 Hz), 3.36 (br d, 2H, J=11.6 Hz), 2.93 (br t, 2H, J=11.8 Hz), 2.88-2.78 (m, 1H), 2.70 (s, 3H), 1.98-1.84 (m, 2H), 1.83-1.68 (m, 2H), 1.63 (quintuplet, 2H, J=7.2 Hz), 1.18 (sextuplet, 2H, J=7.2 Hz), 0.82 (t, 3H, J=7.4 Hz); Calculated (for $C_{24}H_{30}N_2O_3S.C_2H_2O_4$): C 60.45, H 6.24, N 5.42; found: C 60.36, H 5.91, N 5.41.

EXAMPLE 18

Benzenesulfonic acid 1-(4-fluorobenzyl)-3-(1-methylpiperidin-4-yl)-1H-indol-5-yl ester oxalate

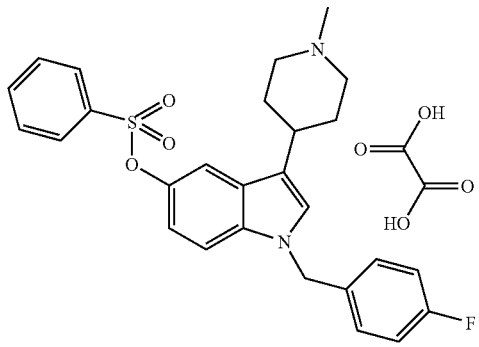

By a method similar to Example 1, using benzenesulfonic acid 3-(1-methylpiperidin-4-yl)-1H-indol-5-yl ester, from example 34 or 45, (0.40 g, 1.08 mmol) in tetrahydrofuran (20 mL) potassium hydride (129 mg of a 35% dispersion in oil, 1.11 mmol), 4-fluorobenzyl bromide (141 mL, 1.11 mmol) provided 340 mg (66%) of the free base of the desired product as a golden oil. The oil was dissolved in ethyl acetate (10 mL) and treated with oxalic acid (63.9 mg, 0.71 mmol, dissolved in 10 mL ethyl acetate), upon which a precipitate formed immediately. Filtration and drying of the precipitate provided 371 mg (91%) of the title oxalate as a white solid: mp=181-184° C.; $^1$H NMR (400 MHz, dmso-$d_6$): 7.84-7.73 (m, 3H), 7.66-7.58 (m, 2H), 7.41 (s, 1H), 7.39 (d, 1H, J=8.8 Hz), 7.26-7.19 (m, 2H), 7.18 (d, 1H, J=1.6 Hz), 7.14-7.06 (m, 2H), 6.66 (dd, 1H, J=9.0, 2.2 Hz), 5.29 (s, 2H), 3.52-3.38 (m, 2H), 3.12-2.96 (m, 2H), 2.94-2.82 (m, 1H), 2.77 (s, 3H), 2.02-1.90 (m, 2H), 1.86-1.70 (m, 2H); MS (APCI): m/e 479.1 (M+1); Calculated (for $C_{27}H_{27}FN_2O_3S.C_2H_2O_4.\bullet 1.4H_2O$): C 58.65, H 5.39, N 4.71; found: C 58.87, H 4.72, N 4.56.

EXAMPLE 19

Benzenesulfonic acid 1-(2,4-difluorobenzyl)-3-(1-methylpiperidin-4-yl)-1H-indol-5-yl ester oxalate

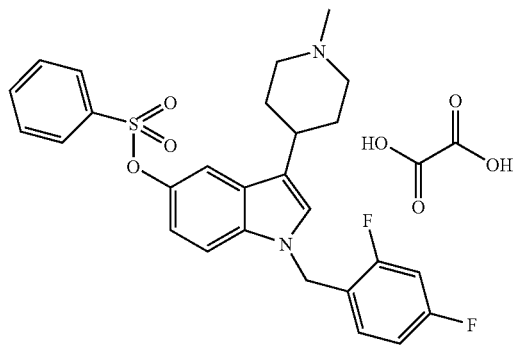

By a method similar to Example 1, using benzenesulfonic acid 3-(1-methylpiperidin-4-yl)-1H-indol-5-yl ester, from example 34 or 45, (0.40 g, 1.08 mmol), tetrahydrofuran (20 mL), potassium hydride (129 mg of a 35% dispersion in oil, 1.11 mmol), 2,4-difluorobenzyl bromide (146 mL, 1.11 mmol) provided 357 mg (66%) of the free base of the desired product as a golden oil. The oil was dissolved in ethyl acetate (10 mL) and treated with oxalic acid (64.7 mg, 0.71 mmol, dissolved in 10 mL ethyl acetate), upon which a precipitate formed immediately. Filtration and drying of the precipitate provided 390 mg (92%) of the title oxalate as a white solid: mp=141-144° C.; $^1$H NMR (400 MHz, dmso-$d_6$): 7.86-7.72 (m, 3H), 7.61 (t, 2H, J=7.8 Hz), 7.39 (d, 1H, J=8.8 Hz), 7.29 (s, 1H), 7.22 (td, 1H, J=9.6, 2.6 Hz), 7.17-7.08 (m, 2H), 6.98 (td, 1H, J=8.4, 2.6 Hz), 6.72 (dd, 1H, J=9.0, 2.2 Hz), 5.33 (s, 2H), 3.28 (br d, 2H, J=11.6 Hz), 2.88-2.72 (m, 3H), 2.63 (s, 3H), 1.93-1.82 (m, 2H), 1.81-1.64 (m, 2H); MS (APCI): m/e 497.1 (M+1); Calculated (for $C_{27}H_{26}F_2N_2O_3S.C_2H_2O_4$): C 59.38, H 4.81, N 4.78; found: C 59.41, H 4.63, N 4.79.

EXAMPLE 20

Benzenesulfonic acid 1-(2-fluorobenzyl)-3-(1-methylpiperidin-4-yl)-1H-indol-5-yl ester hydrochloride

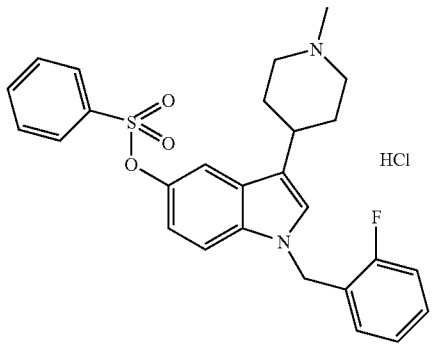

By a method similar to Example 1, using benzenesulfonic acid 3-(1-methylpiperidin-4-yl)-1H-indol-5-yl ester, from example 34 or 45, (0.40 g, 1.08 mmol), tetrahydrofuran (20 mL) potassium hydride (130 mg of a 35% dispersion in oil, 1.13 mmol) and 2-fluorobenzyl bromide (137 mL, 1.13 mmol) provided 63 mg (12%) of the free base of the desired product as a colorless oil. The oil was dissolved in methanol (10 mL) and treated with ammonium chloride (7.0 mg, 0.13 mmol, dissolved in 10 mL of methanol). The solvent was removed in vacuo, providing a solid residue, which was taken up in diethyl ether and sonicated for 5 minutes. Filtration and drying of the precipitate provided 61 mg (91%) of the title hydrochloride as a -white solid: mp=222-224° C.; $^1$H NMR (400 MHz, dmso-d$_6$): 7.81 (d, 2H, J=7.2 Hz), 7.76 (t, 1H, J=7.4 Hz), 7.61 (t, 2H, J=7.6 Hz), 7.39 (d, 1H, J=8.8 Hz), 7.35-7.24 (m, 2H), 7.24-7.12 (m, 2H), 7.12-6.98 (m, 2H), 6.72 (br d, 1H, J=7.6 Hz), 5.40 (s, 2H), 3.48-3.30 (m, 2H, overlapping with H$_2$O), 3.10-2.92 (m, 2H), 2.92-2.80 (m, 1H), 2.72 (s, 3H), 1.98-1.80 (m, 4H); MS (ES+): m/e 479.2 (M+1). Calculated (for C$_{27}$H$_{27}$FN$_2$O$_3$S.HCl.0.7H$_2$O): C 61.57, H 5.43, N 5.31; found: C 61.45, H 5.50, N 5.34.

EXAMPLE 21

Benzenesulfonic acid 1-(3-fluorobenzyl)-3-(1-methyl piperidin-4-yl)-1H-indol-5-yl ester hydrochloride

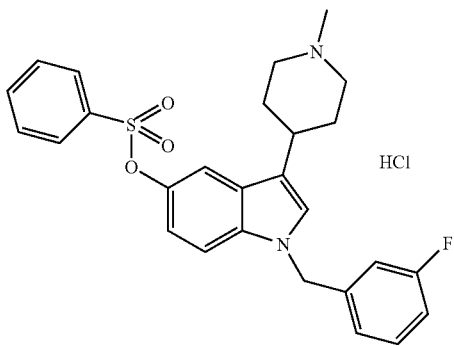

By a method similar to Example 1, using benzenesulfonic acid 3-(1-methylpiperidin-4-yl)-1H-indol-5-yl ester, from example 34 or 45, (0.40 g, 1.08 mmol), tetrahydrofuran (20 mL) potassium hydride (130 mg of a 35% dispersion in oil, 1.13 mmol) and 3-fluorobenzyl bromide (139 mL, 1.13 mmol) provided 309 mg (60%) of the free base of the desired product as yellow foam. The foam was further purified by preparative reverse-phase HPLC, which provided 293 mg (88%) of the title hydrochloride as an off-white solid: mp=103-105° C.; $^1$H NMR (400 MHz, dmso-d$_6$): 10.35 (br s, 1H), 7.81 (d, 2H, J=7.2 Hz), 7.76 (t, 1H, J=8.4 Hz), 7.61 (t, 2H, J=8.0 Hz), 7.42 (s, 1H), 7.38 (d, 1H, J=9.2 Hz), 7.35-7.25 (m, 1H), 7.23 (s, 1H), 7.10-6.93 (m, 3H), 6.68 (br d, 1H, J=9.2 Hz), 5.33 (s, 2H), 3.43 (br d, 2H, J=11.2 Hz), 3.10-2.95 (m, 2H), 2.95-2.80 (m, 1H), 2.74 (s, 3H), 2.00-1.80 (m, 4H); MS (ES+): m/e 479.1 (M+1); Calculated (for C$_{27}$H$_{27}$FN$_2$O$_3$S.HCl..0.5H$_2$O): C 62.00, H 5.39, N 5.35; found: C 61.14, H 5.33, N 5.28.

EXAMPLE 22

Benzenesulfonic acid 1-isobutyl-3-(1-methylpiperidin-4-yl)-1H-indol-5-yl ester hydrochloride

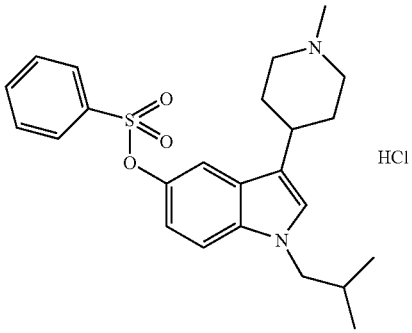

By a method similar to Example 1, using benzenesulfonic acid 3-(1-methylpiperidin-4-yl)-1H-indol-5-yl ester, from example 34 or 45, (0.35 g, 0.9 mmol), tetrahydrofuran (20 mL) potassium hydride (113 mg of a 35% dispersion in oil, 1.0 mmol) and toluene-4-sulfonic acid isobutyl ester (1.08g, 4.7 mmol) and isopropylmethyl tosylate (0.65 g, 0.28 mmol) provided 106 mg (26%) of the free base of the desired product as a colorless oil. The oil was dissolved in methanol (10 mL) and treated with ammonium chloride (13.3 mg, 0.25 mmol, dissolved in 10 mL methanol). The resulting solution was placed in an ultrasound bath for 15 minutes; then it-was concentrated in vacuo to a residue, which was triturated with 9:1 diethyl ether-acetonitrile, upon which immediate formation of a precipitate was observed. Sonication for 5 minutes, followed by filtration and drying of the solid afforded 83 mg (72%) of the title hydrochloride as a tan solid: mp=188-191° C.; $^1$H NMR (400 MHz, dmso-d$_6$): 10.84 (br s, 1H), 7.82 (d, 2H, J=8.0 Hz), 7.76 (t, 1H, J=7.4 Hz), 7.62 (t, 2H, J=7.8 Hz), 7.38 (d, 1H, J=9.2 Hz), 7.24-7.12 (m, 2H), 6.70 (d, 1H, J=7.6 Hz), 3.86 (d, 2H, J=7.2 Hz), 3.40 (br d, 2H, J=11.6 Hz), 3.10-2.94 (m, 2H), 2.92-2.78 (m, 1H), 2.72 (s, 3H), 2.08-1.90 (m, 1H), 1.98-1.80 (m, 4H), 0.76 (d, 6H, J=6.0 Hz); MS (APCI): m/e 427.2 (M+1); Calculated (for C$_{24}$H$_{30}$N$_2$O$_3$S.HCl): C 62.26, H 6.75, N 6.05; found: C 62.08, H 6.70, N 6.44.

EXAMPLE 23

Benzenesulfonic acid 1-cyclohexylmethyl-3-(1-methylpiperidin-4-yl)-1H-indol-5-yl ester hydrochloride

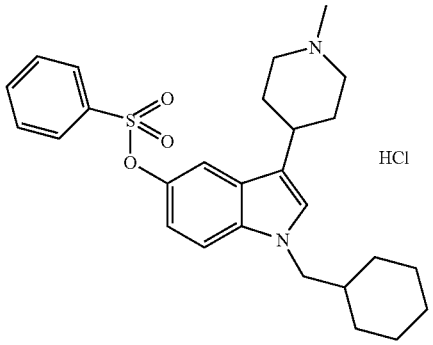

By a method similar to Example 1, using benzenesulfonic acid 3-(1-methylpiperidin-4-yl)-1H-indol-5-yl ester, from example 34 or 45, (0.30 g, 0.81 mmol) tetrahydrofuran (20 mL) potassium hydride (97 mg of a 35% dispersion in oil, 0.85 mmol) and cyclohexylmethyl bromide (226 mL, 1.62 mmol) and after 2 hours at 0° C. provided 120 mg (31%) of the free base of the desired compound as a colorless oil. The oil was dissolved in methanol (5 mL) and treated with ammonium chloride (13.7 mg, 0.25 mmol, dissolved in 10 mL methanol). The resulting solution was placed in an ultrasound bath for 5 minutes before concentrating it in vacuo to a solid residue, which was triturated with diethyl ether and sonicated for 5 minutes. Filtration and drying of the precipitate afforded 111 mg (86%) of the title hydrochloride as a white solid: mp=98-101° C.; $^1$H NMR (400 MHz, DMSO-$d_6$): 7.83 (d, 2H, J=8.0 Hz), 7.76 (t, 1H, J=7.4 Hz), 7.62 (t, 2H, J=7.6 Hz), 7.37 (d, 1H, J=8.8 Hz), 7.17 (d, 2H, J=8.8 Hz), 6.71 (br d, 1H, J=7.6 Hz), 3.88 (d, 2H, J=6.8 Hz), 3.45-3.22 (m, 2H, overlapping with H$_2$O), 3.09-2.93 (m, 2H), 2.90-2.78 (m, 1H), 2.70 (s, 3H), 1.98-1.82 (m, 4H), 1.75-1.48 (m, 4H), 1.48-1.38 (m, 2H), 1.23-0.98 (m, 3H), 0.98-0.82 (m, 2H); MS (APCI): m/e 467.2 (M+1); Calculated (for $C_{27}H_{34}N_2O_3S$·HCl·1.6H$_2$O): C 61.08, H 7.06, N 5.27; found: C 61.26, H 6.77, N 5.25.

EXAMPLE 24

Benzenesulfonic acid 1-(4-phenylbutyl)-3-(1-methylpiperidin-4-yl)-1H-indol-5-yl ester hydrochloride

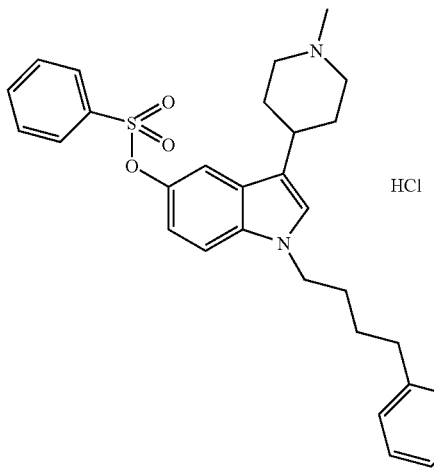

By a method similar to Example 1, using benzenesulfonic acid 3-(1-methylpiperidin-4-yl)-1H-indol-5-yl ester, from example 34 or 45, (0.30 g, 0.81 mmol) in tetrahydrofuran (20 mL) potassium hydride (97 mg of a 35% dispersion in oil, 0.85 mmol) and 1-chloro-4-phenylbutane (1.37 g, 8.1 mmol) provided 32 mg (8%) of the free base of the title compound as a colorless film. The film was dissolved in methanol (10 mL) and treated with ammonium chloride (3.4 mg, 0.06 mmol, dissolved in 10 mL methanol). The resulting solution was placed in an ultrasound bath for 2 minutes and concentrated in vacuo to a residue, which was triturated with diethyl ether. Sonication for 2 minutes, filtration, and drying of the precipitate afforded 27 mg (79%) of the title hydrochloride as a white solid: mp=158-161° C.; $^1$H NMR (400 MHz, dmso-$d_6$): 7.81 (d, 2H, J=7.2 Hz), 7.56 (t, 1H, J=7.2 Hz), 7.61 (t, 2H, J=7.4 Hz), 7.36 (d, 1H, J=8.8 Hz), 7.26-7.04 (m, 7H), 6.69 (d, 1H, J=8.8 Hz), 4.07 (t, 2H, J=6.8 Hz), 3.47-3.28 (m, 2H, overlapping with H$_2$O), 3.10-2.93 (m, 2H), 2.93-2.78 (m, 1H), 2.71 (s, 3H), 2.51 (t, 2H, J=7.4 Hz), 1.98-1.80 (m, 4H), 1.74-1.60 (m, 2H), 1.53-1.40 (m, 2H); MS (ES+): m/e 503.0 (M+1); Calculated (for $C_{30}H_{34}N_2O_3S$·HCl·1.5H$_2$O): C 63.64, H 6.77, N 4.95; found: C 63.53, H 6.32, N 4.72.

EXAMPLE 25

Benzenesulfonic acid 1-(pyrid-2-ylmethyl)-3-(1-methylpiperidin-4-yl)-1H-indol-5-yl ester trifluoroacetate

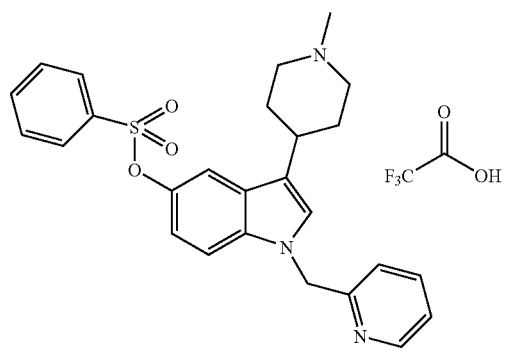

By a method similar to Example 1, using benzenesulfonic acid 3-(1-methylpiperidin-4-yl)-1H-indol-5-yl ester, from example 34 or 45, (0.20 g, 0.54 mmol) tetrahydrofuran (20 mL), potassium hydride (62 mg of a 35% dispersion in oil, 0.54 mmol) and 2-picolyl chloride free base (obtained by SCX purification of 443 mg, 2.7 mmol, of commercial 2-picolyl chloride hydrochloride) as a solution in tetrahydrofuran (3 mL) provided 28 mg (11%) of the free base of the title compound as a colorless film. The film was further purified by reverse-phase HPLC, which provided 25 mg (71%) of the corresponding trifluoroacetate salt as a white, filmy solid: MS (APCI): m/e 462.1 (M+1); $^1$H NMR (400 MHz, CDCl$_3$): 8.54 (dd, 1H, J=4.8, 1.2 Hz), 7.86-7.78 (m, 2H), 7.66-7.57 (m, 1H), 7.55-7.44 (m, 3H), 7.20-7.10 (m, 2H), 7.06 (d, 1H, J=8.8 Hz), 6.97 (s, 1H), 6.73-6.64 (m, 2H), 5.32 (s, 2H), 2.97 (br d, 2H, J=12.0 Hz), 2.66 (tt, 1H, J=11.8, 3.6 Hz), 2.35 (s, 3H), 2.11 (td, 2H, J=12.0, 1.2 Hz), 1.92 (br d, 2H, J=13.2 Hz), 1.74 (qd, 2H, J=12.4, 3.2 Hz).

EXAMPLE 26

Benzenesulfonic acid 1-(2,2,2-trifluoroethyl)-3-(1-methylpiperidin-4-yl)-1H-indol-5-yl ester

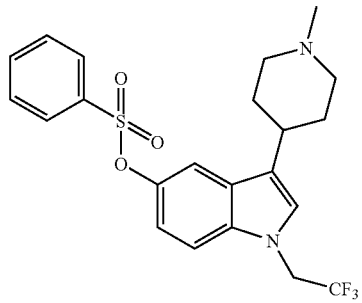

By a method similar to Example 1, using benzenesulfonic acid 3-(1-methylpiperidin-4-yl)-1H-indol-5-yl ester, from example 34 or 45, (435 mg, 1.17 mmol) dimethylformamide (10 mL), sodium hydride (47 mg of a 60% dispersion in oil, 1.17 mmol). 2,2,2-trifluoroethyl trifluoromethanesulfonate (273 mg, 1.17 mmol) provided 213 mg (40%) of the title compound as a white solid: mp=126-129° C.; $^1$H NMR (400 MHz, CDCl$_3$): 7.86-7.78 (m, 2H), 7.67-7.60 (m, 1H), 7.48 (t, 2H, J=7.6 Hz), 7.18-7.10 (m, 2H), 6.86 (s, 1H), 6.81 (dd, 1H, J=9.0, 2.2 Hz), 4.52 (q, 2H, J=8.8 Hz), 2.94 (br d, 2H, J=11.2 Hz), 2.61 (tt, 1H, J=12.0, 3.6 Hz), 2.33 (s, 3H), 2.08 (td, 2H, J=11.6, 2.0 Hz), 1.88 (br d, 2H, J=13.2 Hz), 1.70 (qd, 2H, J=12.4, 3.4 Hz); MS (APCI): m/e 453.1 (M+1); Calculated (for C$_{22}$H$_{23}$F$_3$N$_2$O$_3$S): C 58.40, H 5.12, N 6.19; found: C 58.00, H 5.05, N 6.02.

EXAMPLE 27

Benzenesulfonic acid 1-isopropyl-3-(1-methylpiperidin-4-yl)-1H-indol-5-yl ester oxalate

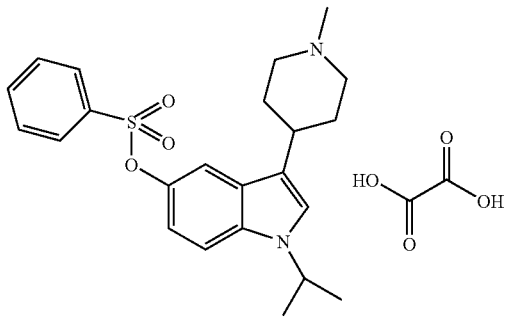

To a solution of toluene-4-sulfonic acid isopropyl ester (1.45 g, 6.7 mmol) in dimethylformamide (20 mL) stirring at 0° C., was added benzenesulfonic acid 3-(1-methylpiperidin-4-yl)-1H-indol-5-yl ester, from example 34 or 45, (250 mg, 0.67 mmol). The cold reaction mixture was then treated with sodium hydride in one portion (30 mg of a 60% dispersion in oil, 0.74 mmol), upon which the solution turned light yellow and then green. The mixture was diluted with methanol (20 mL) and directly applied to a 10 g SCX column. After thoroughly washing with methanol, the column was eluted with a 9:1 mixture of dichloromethane and 2 N ammonia in methanol. The eluent was concentrated in vacuo to a residue, which was further purified on silica gel. Elution with a 9:1 mixture of dichloromethane and methanol provided 171 mg (61%) of the free base of the title compound as an off-white foam. The foam was dissolved in ethyl acetate (10 mL) and treated with oxalic acid (37.3 mg, 0.41 mmol, dissolved in 10 mL of ethyl acetate). A precipitate formed immediately, which was filtered and dried to provide 186 mg (89%) of the title oxalate as an off-white solid: mp=103-107° C.; $^1$H NMR (400 MHz, dmso-d$_6$): 7.86-7.79 (m, 2H), 7.77 (br t, 1H, J=7.6 Hz), 7.68-7.58 (m, 2H), 7.41 (d, 1H, J=8.8 Hz), 7.33 (br s, 1H), 7.11 (br d, 1H, J=2.0 Hz), 6.68 (dd, 1H, J=9.2, 2.0 Hz), 4.63 (septuplet, 1H, J=6.8 Hz), 3.36 (br d, 2H, J=10.8 Hz), 3.02-2.88 (m, 2H), 2.88-2.77 (m, 1H), 2.71 (s, 3H), 1.98-1.87 (m, 2H), 1.87-1.70 (m, 2H), 1.36 (d, 6H, J=6.4 Hz.); MS (ES+): m/e 413.1 (M+1); Calculated (for C$_{23}$H$_{28}$N$_2$O$_3$S.C$_2$H$_2$O$_4$.0.8H$_2$0): C 58.08, H 6.16, N 5.42; found: C 58.14, H 5.86, N 5.56.

EXAMPLE 28

Benzenesulfonic acid 1-cyclopentyl-3-(1-methylpiperidin-4-yl)-1H-indol-5-yl ester oxalate

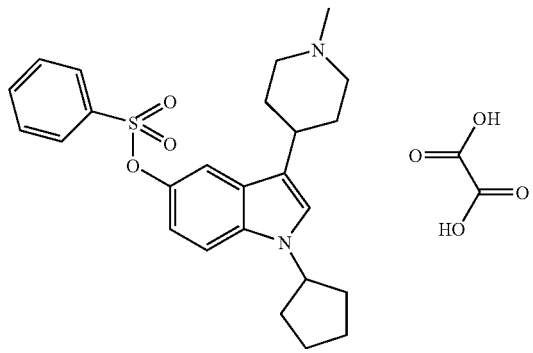

By a method similar to Example 27, using toluene-4-sulfonic acid cyclopentyl ester (1.95 g, 8.1 mmol), dimethylformamide (20 mL), benzenesulfonic acid 3-(1-methylpiperidin-4-yl)-1H-indol-5-yl ester, from example 34 or 45, (250 mg, 0.67 mmol), sodium hydride (36 mg of a 60% dispersion in oil, 0.89 mmol) provided 158 mg (44%) of the free base of the desired compound as a colorless gum. The gum was dissolved in ethyl acetate (10 mL) and treated with oxalic acid (32.4 mg, 0.36 mmol, dissolved in 10 mL ethyl acetate), upon which a precipitate formed immediately. Filtration and drying of the precipitate provided 162 mg (85%) of the title oxalate as an off-white solid: mp=202-205° C.; $^1$H NMR (400 MHz, dmso-d$_6$): 7.84-7.74 (m, 3H), 7.62 (t, 2H, J=7.6 Hz), 7.41 (d, 1H, J=9.2 Hz), 7.30 (s, 1H), 7.13 (d, 1H, J=2.4 Hz), 6.68 (dd, 1H, J=9.0, 2.2 Hz), 4.80-4.70 (m, 1H), 3.38 (br d, 2H, J=11.2 Hz), 2.98 (br t, 2H, J=11.2 Hz), 2.90-2.78 (m, 1H), 2.73 (s, 3H), 2.12-2.00 (m, 2H), 1.98-1.86 (m, 2H), 1.86-1.68 (m, 6H), 1.68-1.56 (m, 2H); MS (ES+): m/e 439.1 (M+1); Calculated (for C$_{25}$H$_{30}$N$_2$O$_3$S.C$_2$H$_2$O$_4$): C 61.35, H 6.10, N 5.30; found: C 61.30, H 6.16, N 5.02.

EXAMPLE 29

Benzenesulfonic acid 1-butyl-3-(1-methylpiperidin-4-yl)-1H-indol-5-yl ester hydrochloride

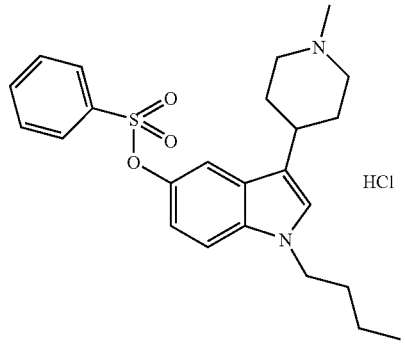

The oxalate salt of benzenesulfonic acid 1-butyl-3-(1-methylpiperidin-4-yl)-1H-indol-5-yl ester, from example 17, (0.25 g) was dissolved in methanol (25mL) and directly applied to a 2 g SCX column. After thoroughly washing with methanol, the column was eluted with a 2:1 mixture of dichloromethane and 2 N ammonia in methanol. The eluent was concentrated in vacuo to provide 204 mg of the corresponding free base as a golden oil. The oil was dissolved in methanol (10 mL) and treated with ammonium chloride (25.6 mg, 0.47 mmol, dissolved in 10 mL methanol). The resulting solution was concentrated in vacuo, and the residue triturated with a minimal amount of diethyl ether-acetonitrile. Filtration and drying of the precipitate provided 183 mg (82%) of the title hydrochloride as a white solid: mp=169-172 C; MS (APCI): m/e 427.2 (M+1); Calculated (for $C_{24}H_{30}N_2O_3S \cdot HCl \cdot 0.2H_2O$): C 61.77, H 6.78, N 6.00; found: C 61.72, H 6.52, N 5.92.

EXAMPLE 30

Benzenesulfonic acid 1-(4-fluorobenzyl)-3-(1-methylpiperidin-4-yl)-1H-indol-5-yl ester hydrochloride

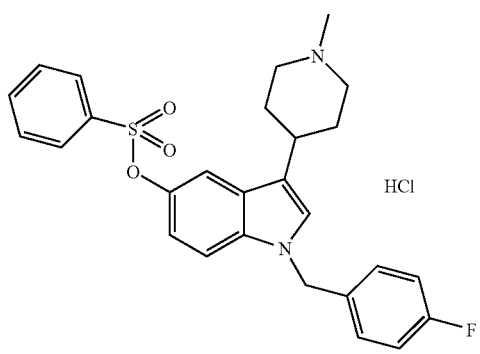

The oxalate salt of benzenesulfonic acid 1-(4-fluorobenzyl)-3-(1-methylpiperidin-4-yl)-1H-indol-5ester, from example 18, (0.30 g) was dissolved in methanol (25 mL) and directly applied to a 2 g SCX column. After thoroughly washing with methanol, the column was eluted with a 2:1 mixture of dichloromethane and 2 N ammonia in methanol. The eluent was concentrated in vacuo to provide 244 mg of the corresponding free base as a golden oil. The oil was dissolved in methanol (10 mL) and treated with ammonium chloride (27.2 mg, 0.51 mmol, dissolved in 10 mL methanol). The resulting solution was concentrated in vacuo, and the residue triturated with a minimal amount of diethyl ether. Filtration and drying of the precipitate provided 226 mg (86%) of the title hydrochloride as a white solid: mp=169-172° C.; MS (APCI): m/e 479.2 (M+1); Calculated (for $C_{27}H_{27}FN_2O_3S \cdot HCl \cdot 0.8H_2O$): C 61.25, H 5.63, N 5.29; found: C 61.20, H 5.42, N 5.68.

EXAMPLE 31

2,6-Difluorobenzenesulfonic acid 2-methyl-3-(1-methylpiperidin-4-yl)-1H-indol-5-yl ester

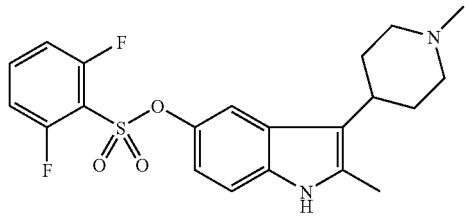

A solution of 2-methyl-3-(1-methylpiperidin-4-yl)-5-hydroxy-1H-indole (4.05 mmol, 0.989 g) in THF (12 mL) and 1M sodium hydroxide (4.09 mL) was treated with 2,6-difluorobenzenesulfonyl chloride (4.46 mmol, 0.948 g).

After stirring one hour at room temperature the reaction was diluted with water (25 mL) and extracted with ethyl acetate (3×25 mL). The organic phases were combined, concentrated in vacuo to afford foam. The free amine was converted to the hydrochloride salt. Acetyl chloride (approximately 1.2 eq) was added to a cooled solution of ethanol (0° C.). After stirring approximately five minutes, this solution was added to a solution of the free amine in ethanol. The biphasic solution was concentrated in vacuo to foam. The foam was dissolved in acetone, crystals formed, collected by filtration to afford 1.12 g (60%) of the title compound: mp=138° C. (decomposes); mass spectrum (ion spray): m/z=420 (M−1); Calculated for $C_{21}H_{22}F_2N_2O_3S \cdot HCl \cdot 0.2H_2O \cdot 0.6C_3H_6O$: C, 55.28; H, 5.49; N, 5.66. Found: C, 55.42; H, 5.46; N, 5.30

EXAMPLE 32

2,6-Difluorobenzenesulfonic acid 6-fluoro-3-(1-methylpiperidin-4-yl)-1H-indol-5-yl ester

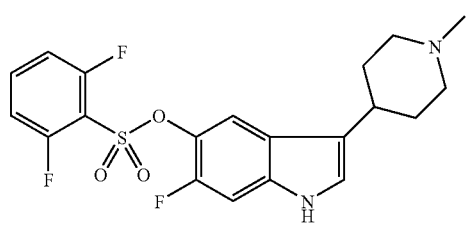

By a method similar to Example 31, using 0.2N sodium hydroxide (2.4 mmol, 12.2 mL), 2,6-difluorobenzenesulfonyl chloride (2.9 mmol, 0.625 g), 6-fluoro-3-(1-methylpiperidin-4-yl)-1H-indole-5-ol (2.4 mmol, 0.608 g) in THF (7.7 mL). The crude isolated product was subjected to normal phase silica gel radial chromatography, 4 mm plate eluting with 9:1 methylene chloride:2M ammonia in methanol at 10 mL/minute. Fractions containing product combined, concentrated in vacuo to a white solid. The title compound was crystallized from methylene chloride to afford 0.282 g (27%) of the title compound: mp=202° C.; Mass spectrum (ion spray): m/z=425 (M+1); $^1$H NMR (DMSOd$_6$): 11.10 (s, 1H), 7.91 (m, 1H), 7.40 (m, 2H), 7.26-7.16 (m, 3H), 2.78 (m, 2H), 2.52 (m, 1H), 2.20 (s, 3H), 1.96 (m, 2H), 1.69 (m, 2H), 1.51 (m, 2H); Calculated for $C_{20}H_{19}F_3N_2O_3S$: C, 56.12; H, 4.57; N, 6.54. Found: C, 56.13; H, 4.56; N, 6.48.

EXAMPLE 33

2,6-Difluorobenzenesulfonic acid 9-(1-methylpiperidin-4-yl)-2,3-dihydro-1H-pyrrolo[1,2-a]indo ester hydrochloride

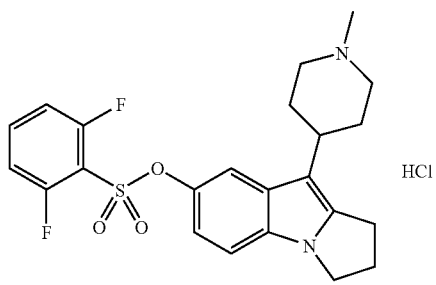

By a method similar to Example 31, using 9-(1-methylpiperidin-4-yl)-2,3-dihydro-1H-pyrrolo[1,2-a]indol-6ol (270 mg, 1.0 mmol) in NaOH (6.5 mL, 1.3 mmol, 0.2 N), THF (3.0 mL). and 2,6-difluorobenzenesulfonyl chloride gave a crude residue that was purified by PCTLC (silica gel GF rotor; 95:5 CHCl$_3$:2M NH$_3$ in MeOH) and the hydrochloride formed in EtOAc affording 388 mg (81%) of the title compound as a white powder: mp=149° C. (transition) and 229° C.; MS (ES+): m/e 447.1 (M+1); Calculated for C$_{23}$H$_{24}$F$_2$N$_2$O$_3$S.HCl: Calcd: C, 57.20; H, 5.22; N, 5.80. Found: C, 56.90; H, 5.07; N, 5.74.

EXAMPLE 34

Benzenesulfonic acid 3-(1-methylpiperidin-4-yl)-1H-indol-5-yl ester

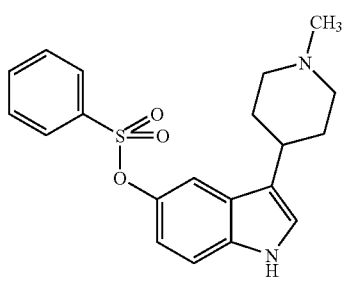

By a method similar to Example 31, using benzenesulfonyl chloride (280 µL, 2.2 mmol), 3-(1-methylpiperidin-4-yl)-5-hydroxy-1H-indole (418 mg, 1.8 mmol) in 0.2 N sodium hydroxide (10 mL, 2.0 mmol) and THF (6 mL) gave 650 mg of an off white solid. The crude product was recrystallized from ethyl acetate to give 505 mg (75%) of tan needles: mp=192-194° C.; MS(m/e): 370 (M$^+$); Calculated for C$_{20}$H$_{22}$N$_2$O$_3$S: C, 64.84; H, 5.99; N, 7.56. Found: C, 64.92; H, 6.19; N, 7.67.

EXAMPLE 35

2,4-Difluorobenzenesulfonic acid 3-(1-methylpiperidin-4-yl)-1H-indol-5-yl ester

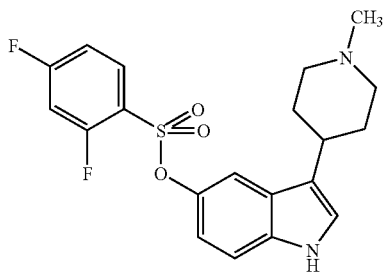

By a method similar to Example 31, using 2,4-difluorobenzenesulfonyl chloride (463 mg, 2.2 mmol) was added to a solution of 3-(1-methylpiperidin-4-yl)-5-hydroxy-1H-indole (418 mg, 1.8 mmol) in 0.2 N sodium hydroxide (10 mL, 2.0 mmol) and THF (5 mL) gave 735 mg of product. The crude product was recrystallized from ethyl acetate/ hexanes to give 680 mg (92%) of white crystals: mp=163-164° C.; MS(m/e): 406 (M$^+$); Calculated for C$_{20}$H$_{20}$F$_2$N$_2$O$_3$S: C, 59.10; H, 4.96; N, 6.89. Found: C, 58.86; H, 4.94; N, 6.95.

EXAMPLE 36

4-Iodobenzenesulfonic acid 3-(1-methylpiperidin-4-yl)-1H-indol-5-yl ester

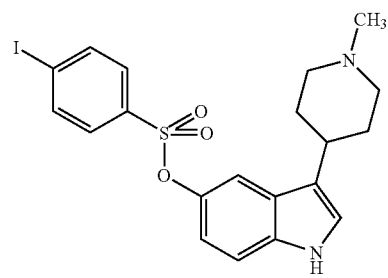

By a method similar to Example 31, using 4-Iodobenzenesulfonyl chloride (347 mg, 1.15 mmol) in THF (4 mL), 3-(1-methylpiperidin-4-yl)-5-hydroxy-1H-indole (220 mg, 0.96 mmol) in 0.2 N sodium hydroxide (5.2 mL, 1.05 mmol) and THF (4 mL) gave 470 mg of an off white solid. The crude product was recrystallized from ethyl acetate/hexanes to give 404 mg (85%) of tan crystals: mp=174-176° C.; MS(m/e): 495 (M−1); Calculated for C$_{20}$H$_{21}$IN$_2$O$_3$S: Calcd: C, 48.40; H, 4.26; N, 5.64. Found: C, 48.74; H, 4.20; N, 5.59.

EXAMPLE 37

4-Chlorobenzenesulfonic acid 3-(1-methylpiperidin-4-yl)-1H-indol-5-yl ester

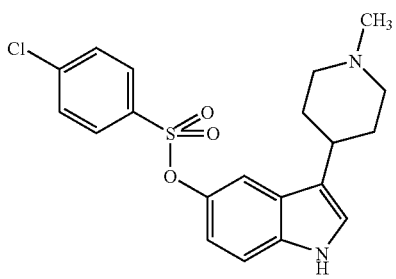

By a method similar to Example 31, using 4-chlorobenzenesulfonyl chloride (242 mg, 1.15 mmol) and 3-(1-methylpiperidin-4-yl)-5-hydroxy-1H-indole (220 mg, 0.96 mmol), 0.2 N sodium hydroxide (5.5 mL, 1.1 mmol) gave 380 mg of a white solid. The crude product was recrystallized from ethyl acetate/hexanes to give 300 mg (78%) of the title compound as an off white powder: mp=182-183.5° C.; MS(m/e): 404 (M$^+$); Calculated for C$_{20}$H$_{21}$ClN$_2$O$_3$S: C,59.33; H, 5.23; N, 6.92. Found: C, 59.24; H, 5.22; N, 6.90.

EXAMPLE 38

4-Methoxybenzenesulfonic acid 3-(1-methylpiperidin-4-yl)-1H-indol-5-yl ester

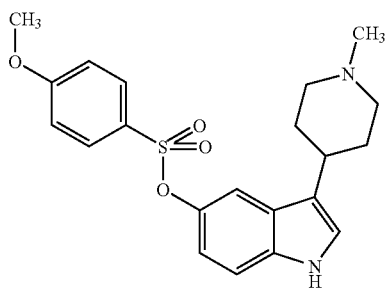

By a method similar to Example 31, using 4-methoxybenzenesulfonyl chloride (248 mg, 1.2 mmol) and 3-(1-methylpiperidin-4-yl)-5-hydroxy-1H-indole (230 mg, 1.0 mmol), 0.2 N sodium hydroxide (5.5 mL, 1.1 mmol) gave 225 mg of crude product. The crude product was recrystallized from ethyl acetate to give 195 mg (49%) of the title compound as a white powder: mp=186-187° C.; MS(m/e): 400 (M+); Calculated for $C_{21}H_{24}N_2O_4S$: Calcd: C, 62.98; H, 6.04; N, 6.99. Found: C, 63.10; H, 6.18; N, 7.04.

EXAMPLE 39

4-Methylphenylsulfonic acid 3-(1-methylpiperidin-4-yl)-1H-indol-5-yl ester

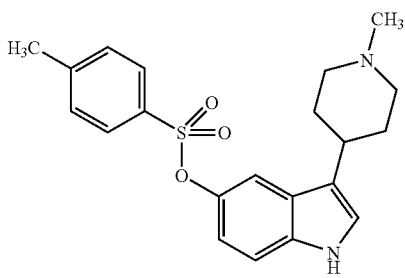

By a method similar to Example 31, using 4-methylbenzenesulfonyl chloride (228 mg, 1.2 mmol) and 3-(1-methylpiperidin-4-yl)-5-hydroxy-1H-indole (230 mg, 1.0 mmol), 0.2 N sodium hydroxide (5.5 mL, 1.1 mmol) gave 400 mg of crude product. The crude product was recrystallized from ethyl acetate to give 305 mg (79%) of a white powder: mp=186-187° C. MS(m/e): 384 (M+); Calculated for $C_{21}H_{24}N_2O_3S$: Calcd: C, 65.60; H, 6.29; N, 7.29. Found: C, 65.50; H, 6.35; N, 7.23.

EXAMPLE 40

2-Fluorobenzenesulfonic acid 3-(1-methylpiperidin-4-yl)-1H-indol-5-yl ester

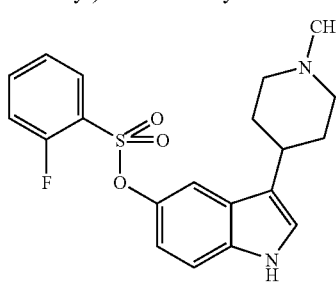

By a method similar to Example 31, using 2-fluorobenzenesulfonyl chloride (234 mg, 1.2 mmol) added dropwise to a solution of 3-(1-methylpiperidin-4-yl)-5-hydroxy-1H-indole (231 mg, 1.0 mmol) in 0.2 N sodium hydroxide (5.5 mL, 1.1 mmol) and THF (5 mL) gave 448 mg of the title compound as a crystalline solid. The product was recrystallized from ethyl acetate/hexanes to give 320 mg (82%) of the title compound an off white powder: mp=180-182° C.; MS(m/e): 389 (M+1); Calculated for $C_{20}H_{21}FN_2O_3S$: Calcd: C, 61.84; H, 5.45; N, 7.21. Found: C, 61.83; H, 5.57; N, 7.26.

EXAMPLE 41

2,3,4-Trifluorobenzenesulfonic acid 3-(1-methylpiperidin-4-yl)-1H-indol-5-yl ester

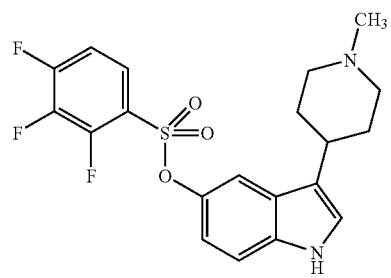

By a method similar to Example 31, using 2,3,4-trifluorobenzenesulfonyl chloride (280 mg, 1.2 mmol) and 3-(1-methylpiperidin-4-yl)-5-hydroxy-1H-indole (231 mg, 1.0 mmol) and 0.2 N sodium hydroxide (5.5 mL, 1.1 mmol) gave 449 mg of a purple foam. The crude product was purified by radial chromatography (silica gel, 2000 micron rotor, 100/10 methylene chloride/methanol then 100/10/0.5 methylene chloride/methanol/ammonium hydroxide) to give 418 mg (98%) of homogeneous product. The product was crystallized from ethyl acetate/hexanes to give 280 mg of the title compound as a white powder: mp=160-162° C.; MS(m/e): 424 (M+); Calculated for $C_{20}H_{19}F_3N_2O_3S$: C, 56.60; H, 4.51; N, 6.60. Found: C, 56.53; H, 4.78; N, 6.51.

EXAMPLE 42

2,6-Difluorobenzenesulfonic acid 3-(1-methylpiperidin-4-yl)-1H-indol-5-yl ester

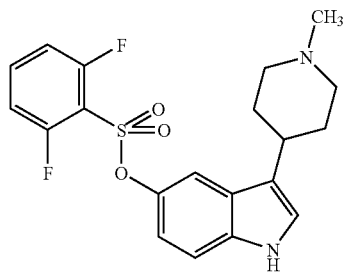

By a method similar to Example 31, using 2,6-difluorobenzenesulfonyl chloride (256 mg, 1.2 mmol) and 3-(1-methylpiperidin-4-yl)-5-hydroxy-1H-indole (231 mg, 1.0 mmol), and 0.2 N sodium hydroxide (5.5 mL, 1.1 mmol) gave 400 mg (98%) of the title compound as an off white powder were obtained. The product was recrystallized from ethyl acetate/methanol/hexanes: mp=214-215° C.; MS(m/e): 407 (M+1); Calculated for $C_{20}H_{20}F_2N_2O_3S$: C, 59.10; H, 4.96; N, 6.89. Found: C, 59.07; H, 5.16; N, 6.73.

EXAMPLE 43

4-Nitrobenzenesulfonic acid 3-(1-methylpiperidin-4-yl)-1H-indol-5-yl ester

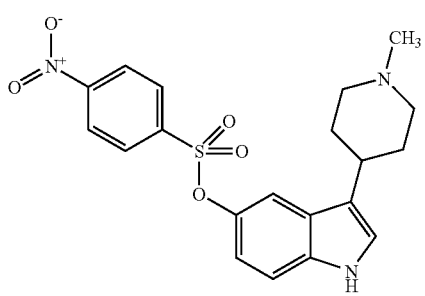

By a method similar to Example 31, using 4-nitrobenzenesulfonyl chloride (997 mg, 4.05 mmol) was added to a mixture of 3-(1-methylpiperidin-4-yl)-5-hydroxy-1H-indole (777 mg, 3.4 mmol) in 0.2 N sodium hydroxide (18.6 mL, 3.7 mmol) and THF (20 mL) gave 1.4 g of an orange foam. The product was crystallized from ethyl acetate/hexanes to give 485 mg (35%) of an orange powder. The mother liquors were purified by flash chromatography (silica gel, 5%,7% 2M ammonia in methanol/methylene chloride) to give 800 mg (57%) of the title compound as yellow foam: Total yield was 92%: mp=171-172° C.; MS(m/e): 416 (M+1), 414 (M−1); Calculated for $C_{20}H_{21}N_3O_5S$: C, 57.82; H, 5.09; N, 10.11. Found: C, 57.35; H, 4.96; N, 9.88.

EXAMPLE 44

2,6-Difluorobenzenesulfonic acid 3-(1-methyl-1,2,3,6-tetrahydropyridin-4-yl)-1H-indol-5-yl ester

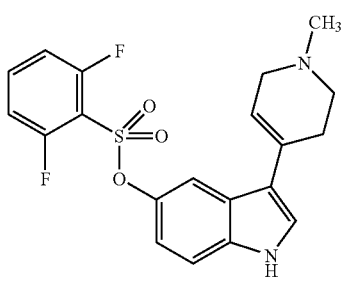

By a method similar to Example 31, using a solution of 2,6-difluorobenzenesulfonyl chloride (380 mg, 1.79 mmol) in THF (5 mL) was added to a mixture of 3-(1-methyl-1,2,3,6-tetrahydropyridin-4-yl)-5-hydroxy-1H-indole (340 mg, 1.49 mmol) in 0.2 N sodium hydroxide (8.2 mL, 1.64 mmol) and THF (5 mL) gave 170 mg (28%) of homogeneous product as a tan solid. The product was crystallized from ethyl acetate to give 96 mg (16%) of the title compound as a yellow powder: mp 183° C. dec; MS(m/e): 405 (M+1), 403 (M−1); Calculated for $C_{20}H_{18}F_2N_2O_3S$: C, 59.40; H, 4.49; N, 6.93. Found: C, 59.22; H, 4.24; N, 6.65.

EXAMPLE 45

Benzenesulfonic acid 3-(1-methylpiperidin-4-yl)-1H-indol-5-yl ester and

Benzenesulfonic acid 1-benzenesulfonyl-3-(1-methylpiperidine-4-yl)-1H-indol-5-yl ester

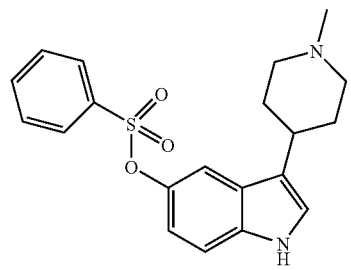

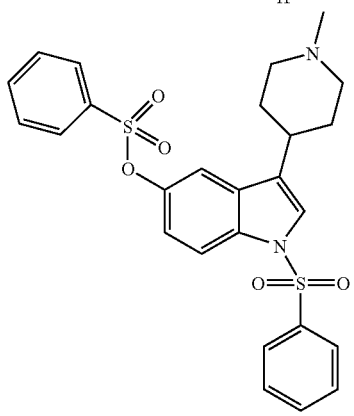

To a solution of 3-(1-methylpiperidin-4-yl)-5-hydroxy-1H-indole (4.75 g, 20.6 mmol) in dimethylformamide (25 mL), stirring at 0° C. under nitrogen, was added sodium hydride in one portion (0.83 g of a 60% dispersion in oil, 20.6 mmol). The green solution turned brown; after stirring for 30 minutes at 0° C. benzenesulfonyl chloride (2.63 mL, 20.6 mmol) was added in one portion, then the reaction mixture was allowed to stir until the reaction was complete. The solution was poured into water (125 mL), then extracted with ethyl acetate (4×125 mL). The combined organic extracts were dried over magnesium sulfate, filtered, and concentrated in vacuo to a residue which was further purified on silica gel. Elution with a 9:1 mixture of dichloromethane and 2 N ammonia in methanol provided 5.40 g (70%) of benzenesulfonic acid 3-(1-methylpiperidin-4-yl)-1H-indol-5-yl ester as a tan solid: mp=189-194° C.; $^1$H NMR (400 MHz, dmso-d$_6$): 10.97 (br s, 1H), 7.85-7.72 (m, 3H), 7.65-7.54 (mm, 2H), 7.24 (d, 1H, J=8.8 Hz), 7.11 (d, 1H, J=2.0 Hz), 6.88 (d, 1H, J=1.2 Hz), 6.69 (dd, 1H, J=8.8, 1.6 Hz), 2.77 (br d, 2H, J=11.2 Hz), 2.52-2.40 (m, 1H), 2.16 (s, 3H), 1.91 (br t, 2H, J=11.2 Hz), 1.67 (br d, 2H, J=12.0 Hz), 1.58-1.44 (m, 2H); MS(ES+): m/e 371.0 (M+1).

Benzenesulfonic acid 1-benzenesulfonyl-3-(1-methylpiperidin-4-yl)-1H-indol-5-yl ester was also obtained as a side product Chromatography provided 290 mg (3%) of the aforementioned compound as a gold-colored oil. A solution of the oil in methanol (10 mL) was treated with ammonium chloride (30.3 mg, 0.56 mmol, dissolved in 10 mL of methanol). Concentration in vacuo, followed by trituration in a minimal amount of diethyl ether, filtration, and drying of the resulting precipitate afforded 272 mg (87%) of benzenesulfonic acid 1-benzenesulfonyl-3-(1-methylpiperidin-4-yl)-1H-indol-5-yl ester as a tan solid: mp=123-127° C.; MS (ES+): m/e 511.0 (M+1); $^1$H NMR (400 MHz, dmso-$d_6$): 7.98-7.92 (m, 2H), 7.90-7.84 (m, 1H), 7.82-7.74 (m, 3H), 7.70-7.64 (m, 1H), 7.64-7.52 (m, 5H), 7.04-6.98 (m, 2H), 2.77 (br d, 2H, J=10.8 Hz), 2.52-2.40 (m, 1H), 2.17 (s, 3H), 1.91 (br t, 2H, J=10.8 Hz), 1.68-1.58 (m, 2H), 1.56-1.42 (m, 2H); Calculated (for $C_{26}H_{26}N_2O_5S_2 \cdot HCl \cdot 1.5H_2O$): C 54.39, H 5.26, N 4.88, Cl 6.17; found: C 54.21, H 4.93; N 5.06; Cl 6.38.

EXAMPLE 46

Benzenesulfonic acid 3-(1-methyl-1,2,3,6-tetrahydropyridin-4-yl)-1H-indol-5-yl ester and Benzenesulfonic acid 1-(benzenesulfonyl) acid 3-(1-methyl1,2,3,6-tetrahydropyridin-4-yl)-1H-indol-5-yl ester hydrochloride

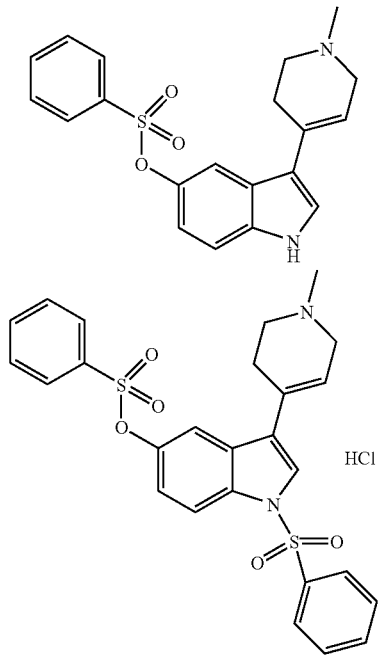

By a method similar to Example 45, using 3-(1-methyl-1,2,3,6-tetrahydropyridin-4-yl)-5-hydroxy-1H-(1.25 g, 5.47 mmol) in dimethylformamide (20 mL), sodium hydride (0.22 g of a 60% dispersion in oil, 5.47 mmol), and benzenesulfonyl chloride (699 µL, 5.47 mmol) provided 700 mg (35%) of Benzenesulfonic acid 3-(1-methyl-1,2,3,6-tetrahydropyridin-4-yl)-1H-indol-5-yl ester as a tan solid: mp=186-190° C.; MS (APCI): m/e 369.3 (M+1); $^1$H NMR (400 MHz, dmso-$d_6$): 11.32 (br s, 1H), 7.90-7.80 (m, 2H), 7.77 (t, 1H, J=7.2 Hz), 7.62 (t, 2H, J=7.6 Hz), 7.41 (d, 1H, J=2.4 Hz), 7.30 (d, 1H, J=8.8 Hz), 7.13 (d, 1H, J=2.4 Hz), 6.74 (dd, 1H, J=8.8, 2.4 Hz), 5.60 (br s, 1H), 2.97-2.91 (m, 2H), 2.49 (br t, 2H, J=5.6 Hz), 2.42-2.36 (m, 2H), 2.24 (s, 3H).

Benzenesulfonic acid 1-benzenesulfonyl-3-(1-methyl-1,2,3,6-tetrahydropyridin-4-yl)-1H-indol-5-yl ester hydrochloride 450 mg (16%) was isolated by chromatography as a gold colored oil which was dissolved in methanol (10 mL) and treated with ammonium chloride (65.3 mg, 1.22 mmol, added as a solution in 10 mL of methanol). The solution was concentrated in vacuo, and the residue was triturated in a minimal amount of diethyl ether. Separation of the supernatant followed and drying of the precipitate afforded 270 mg (56%) of benzenesulfonic acid 1-benzenesulfonyl-3-(1-methyl-1,2,3,6-tetrahydropyridin-4-yl)-1H indol-5yl ester hydrochloride as a white solid: mp=257-260° C.; $^1$H NMR (400 MHz, dmso-$d_6$,): 10.62 (br s, 1H), 8.06 (s, 1H), 8.02-7.99 (m, 2H), 7.92 (d, 1H, J=9.2 Hz), 7.83-7.79 (m, 3H), 7.72-7.66 (mm, 1H), 7.65-7.56 (m, 4H), 7.38 (d, 1H, J=2.0 Hz), 6.97 (dd, 1H, J=8.8, 2.4 Hz), 5.93 (br s, 1H), 3.97-3.85 (m, 1H), 3.76-3.62 (m, 1H), 3.60-3.48 (m, 1H), 3.28-3.15 (m, 1H), 2.88-2.72 (m, 2H), 2.82 (s, 3H); IR (KBr): 3431, 3145, 2671, 2539, 1583, 1577, 1455, 1448, 1351, 1195, 1175, 1166 cm$^{-1}$; MS (APCI): m/e 509.4 (M+1); Calculated (for $C_{26}H_{24}N_2O_5S_2 \cdot 0.9HCl \cdot 0.1H_2O$): C 57.49, H 4.66, N 5.16; found: C 57.85, H 4.73, N 5.30.

EXAMPLE 47

2,6-Difluorobenzenesulfonic acid 3-(1-methylpiperidin-4-yl)-1H-indol-5-yl ester and 2,6-Difluorobenzenesulfonic acid 1-(2,6-difluorobenzenesulfonyl)-3-(1-methylpiperidin-4-yl)-1H-indol-5-yl ester hydrochloride

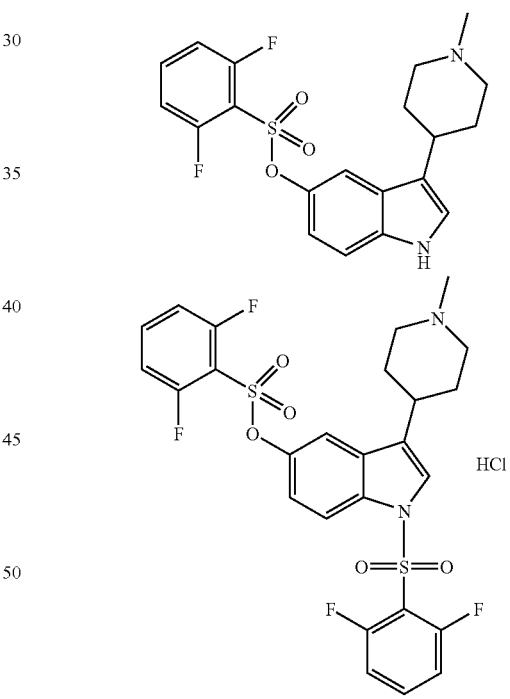

By a method similar to Example 45, using 3-(1-methyl-pyridin-4-yl)-5-hydroxy-1H-indole (1.50 g, 6.5 mmol) in dimethylformamide (40 mL), sodium hydride (0.29 g of a 60% dispersion in oil, 7.2 mmol), 2,6-difluorobenzenesulfonyl chloride (1.52 g, 7.2 mmol) provided 1.35 g (51%) of 2,6-difluorobenzenesulfonic acid 3-(1-methylpiperidin-4-yl)-1H-indol-5-ylester as an off-white solid: mp 235-238° C.; MS(ES+): m/e 407.0 (M+1); $^1$H NMR (400 MHz, dmso-$d_6$): 11.04 (br s, 1H), 7.92-7.82 (m, 1H), 7.42-7.33 (m, 2H), 7.29 (d, 1H, J=8.8 Hz), 7.15 (d, 1H, J=2.0 Hz), 7.06 (d, 1H, J=2.0 Hz), 6.79 (dd, 1H, J=8.8, 1.8 Hz), 2.78 (br d, 2H, J=11.2 Hz), 2.56-2.46 (m, 1H), 2.16 (s, 3H), 1.93 (br t, 2H, J=11.8 Hz), 1.74-1.64 (m, 2H), 1.60-1.46 (m, 2H).

2,6-Difluorobenzenesulfonic acid 1-(2,6-difluorobenzenesulfonyl)-3-(1-methylpiperidin-4-yl)-1H-indol-5-yl ester was also obtained. Chromatography provided 236 mg (6%) of the aforementioned compound as a yellow solid. The free base was dissolved in methanol (10 mL) and treated with ammonium chloride (21.6 mg, 0.41 mmol, dissolved in 10 mL of methanol). The resulting solution was concentrated in vacuo, and the residue was triturated with a minimal amount of diethyl ether. Filtration and drying of the precipitate provided 219 mg (87%) of 2,6-difluorobenzenesulfonic acid 1-(2,6-difluoro-benzenesulfonyl)-3-(1-methylpiperin-4-yl)-1H-indol-5-yl ester as an off-white solid: mp 95-98° C.; MS (ES+): m/e 583.0 (M+1); $^1$H NMR (400 MHz, dmso-d$_6$): 7.96-7.84 (m, 1H), 7.84-7.74 (m, 1H), 7.71 (d, 1H, J=9.2 Hz), 7.62-7.52 (mm, 2H), 7.42-7.28 (m, 4H), 7.10 (br d, 1H, J=8.8 Hz), 3.40-3.22 (br m, 2H, overlapping with H$_2$O), 3.04-2.82 (br m, 3H), 2.68 (br s, 3H), 2.00-1.78 (br m, 4H); Calculated (for C$_{26}$H$_{22}$F$_4$N$_2$O$_5$S$_2$.HCl.0.6H$_2$O): C 49.58, H 3.87, N 4.44, Cl 5.62; found: C 49.58, H 3.76, N 4.51, Cl 5.48.

EXAMPLE 48

2,6-Difluorobenzenesulfonic acid 1-phenethyl-3-(1-methylpiperidin-4-yl)-1H-indol-5-yl ester hydrochloride

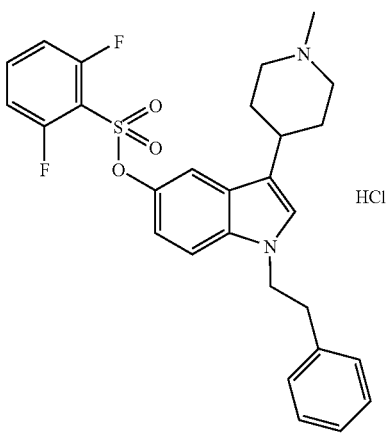

To a solution of 1-phenethyl-3-(1-methylpiperidin-4-yl)-5-hydroxy-1H-indole (175 mg, 0.52 mmol) and 2,6-difluorobenzenesulfonyl chloride (133 mg, 0.58 mmol) in tetrahydrofuran (20 mL), stirring at room temperature, was added 2,6-lutidine dropwise (134 mL, 1.16 mmol). The reaction mixture was stirred for 72 hours at room temperature, before diluting it with methanol (15 mL) and applying it directly to a 5 g SCX column. After thoroughly washing with methanol, the column was eluted with a 9:1 mixture of dichloromethane and 2 N ammonia in methanol. The eluent was concentrated in vacuo to a residue, which was purified on silica gel. Elution with a 9:1 mixture of dichloromethane and methanol provided 191 mg (64%) of the free base of the desired compound as a tan gum. The gum was further purified by preparative reverse-phase HPLC, which provided 156 mg (44%) of the title hydrochloride as an off-white solid: mp=209-212° C.; $^1$H NMR (400 MHz, dmso-d$_6$): 10.55 (br s, 1H), 7.95-7.82 (m, 1H), 7.48-7.34 (m, 3H), 7.30 (s, 1H), 7.25-7.08 (m, 6H), 6.76 (br d, 1H, J=8.4 Hz), 4.29 (t, 2H, J=7.4 Hz), 3.41 (br d, 2H, J=12.4 Hz), 3.10-2.97 (m, 2H), 2.96 (t, 2H, J=7.0 Hz), 2.94-2.82 (m, 2H), 2.72 (s, 3H), 1.96-1.75 (m, 4H); MS (APCI): m/e 511.2 (M+1); Calculated (for C$_{28}$H$_{28}$F$_2$N$_2$O$_3$S.HCl.0.6H$_2$O): C 60.39, H 5.28, N 5.03; found: C 60.43, H 5.41, N 5.14.

EXAMPLE 49

2,6-Difluorobenzenesulfonic acid 1-(4-fluorobenzyl)-3-(1-methylpiperidin-4-yl)-1H-indol-5-yl ester hydrochloride

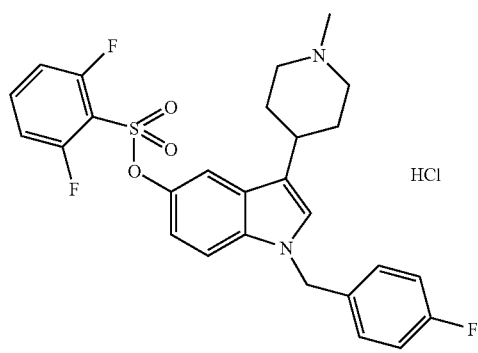

By a method similar to Example 48, using 1-(4-fluorobenzyl)-3-(1-methylpiperidin-4-yl)-5-hydroxy-1H-indole (325 mg, 0.96 mmol), 2,6-difluorobenzenesulfonyl chloride (306 mg, 1.44 mmol) in tetrahydrofuran (20 mL), 2,6-lutidine dropwise (335 mL, 2.88 mmol) gave 323 mg (65%) which provided 303 mg (93%) of the corresponding hydrochloride salt as a white solid: mp=114-118° C.; $^1$H NMR (400 MHz, dmso-d$_6$): 10.43 (br s, 1H), 7.93-7.82 (m, 1H), 7.50-7.30 (m, 5H), 7.28-7.18 (m, 2H), 7.15-7.03 (m, 2H), 6.78 (dd, 1H, J=8.8, 1.6 Hz), 5.31 (s, 2H), 3.42 (br d, 2H, J=11.2 Hz), 3.14-2.98 (m, 2H), 2.98-2.87 (m, 1H), 2.73 (s, 3H), 2.03-1.80 (mm, 4H); MS (ES+): m/e 515.1 (M+1); Calculated (for C$_{27}$H$_{25}$F$_3$N$_2$O$_3$S.HCl 1.5H$_2$O): C 56.20, H 4.89, N 4.85; found: C 56.11, H 4.53, N 4.64.

EXAMPLE 50

2,6-Difluorobenzenesulfonic acid 1-benzyl-3-(1-methylpiperidin-4-yl)-1H-indol-5-yl ester hydrochloride

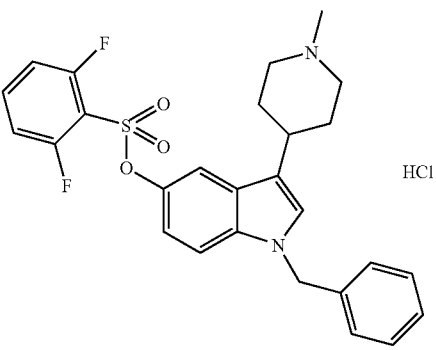

By a method similar to Example 48, using 1-benzyl-3-(1-methylpiperidin-4-yl)-5-hydroxy-1H-indole (320 mg, 1.0 mmol), 2,6-difluorobenzenesulfonyl chloride (234 mg, 1.1 mmol) in tetrahydrofuran (20 mL), 2,6-lutidine (255 μL, 2.2 mmol) provided 382 mg (77%) of the free base of the desired compound as a colorless oil. A portion of this oil (182 mg) was dissolved in methanol (10 mL) and treated with ammonium chloride (19.6 mg, 0.37 mmol, dissolved in 10 mL methanol). The resulting solution was placed in an ultrasound bath for 5 minutes before removing the solvent in vacuo. The resulting residue was triturated with diethyl ether. Filtration and drying of the precipitate afforded 160 mg (82%) of the title hydrochloride as a white solid: mp=225-227° C.; $^1$H NMR (400 MHz, dmso-$d_6$): 7.93-7.82 (m, 1H), 7.46-7.30 (mm, 5H), 7.30-7.12 (m, 5H), 6.78 (dd, 1H, J=8.8, 2.0 Hz), 5.33 (s, 2H), 3.42-3.24 (m, 2H, overlapping with H$_2$O), 3.04-2.84 (m, 3H), 2.68 (s, 3H), 2.00-1.78 (m, 4H); MS (ES+): m/e 496.9 (M+1); Calculated (for $C_{27}H_{26}F_2N_2O_3S \cdot HCl$): C 60.84, H 5.11, N 5.26; found: C 60.69, H 5.00, N 5.26.

EXAMPLE 51

4-Fluorobenzenesulfonic acid 3-(1-methylpiperidin-4-yl)-1H-indol-5-yl ester

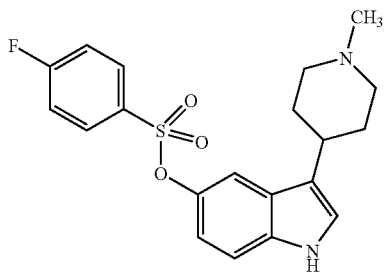

To a solution of 3-(1-methylpiperidin-4-yl)-5-hydroxy-1H-indole (500 mg, 2.2 mmol) and triethylamine (333 μL, 2.4 mmol) in THF (5 mL) and DMF (5 mL) was added 4-fluorobenzenesulfonyl chloride (465 mg, 2.4 mmol). The reaction mixture was stirred at ambient temperature for 18 h. The reaction mixture was cooled on an ice bath and diluted with ethyl acetate. The diluted reaction mixture was washed with cold 0.2 N NaOH, cold water, brine, dried (Na$_2$SO$_4$), filtered and concentrated under reduced pressure to give a white foam. The foam was crystallized from ethyl acetate to give 360 mg of a white powder. The mother liquors were purified by radial chromatography (silica gel, 2000 micron rotor, 5% methanol and 0.5% ammonium hydroxide in methylene chloride then 10% methanol and 0.5% ammonium hydroxide in methylene chloride) to give 297 mg (78%) total yield of a clear oil. The oil was crystallized from ethyl acetate/hexanes to give a white powder: mp 170-172° C.; MS(m/e): 388 (M$^+$); Calculated for $C_{20}H_{21}FN_2O_3S$: C, 61.84; H, 5.45; N, 7.21. Found: C, 62.13; H, 5.58; N, 7.25.

EXAMPLE 52

2,6-Difluorobenzenesulfonic acid 1-methyl-3-(1-methylpiperidin-4-yl)-1H-indol-5-yl ester oxalate

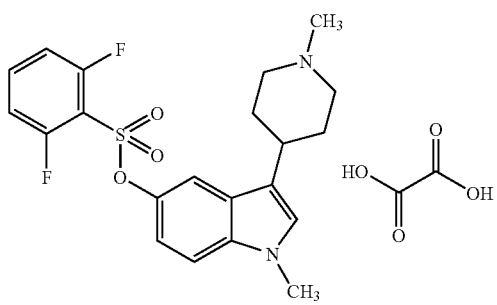

A solution of 2,6-difluorobenzenesulfonyl chloride (312 mg, 1.47 mmol) in methylene chloride (2 mL) was added to a solution of 1-methyl-3-(1-methylpiperidin-4-yl)-5-hydroxy-1H-indole (327 mg, 1.34 mmol) and triethylamine (226 μL, 1.6 mmol) in tetrahydrofuran (10 mL), methylene chloride (2 mL) and DMF (6 mL). The reaction mixture was stirred at ambient temperature for 1 h. The reaction mixture was diluted with water and ethyl acetate, basified with saturated NaHCO$_3$, and extracted with ethyl acetate. The ethyl acetate extracts were washed with water, brine, dried (NaSO$_4$), filtered and concentrated under reduced pressure to give 550 mg of a white solid. The product was purified by flash chromatography (silica gel, 5%,10% 2M ammonia in methanol/methylene chloride) to give 440 mg (78%) of homogeneous title compound as a white foam. The product was crystallized as the oxalic acid salt from ethyl acetate to give a white powder: mp=195-198° C. dec; MS(m/e): 421 (M+1); Calculated for $C_{23}H_{22}F_2N_2O_3S \cdot C_2H_2O_4$: C, 54.11; H, 4.74; N, 5.49. Found: C, 53.86; H, 4.62; N, 5.29.

EXAMPLE 53

4-Aminobenzenesulfonic acid 3-(1-methylpiperidin-4-yl)-1H-indol-5-yl ester

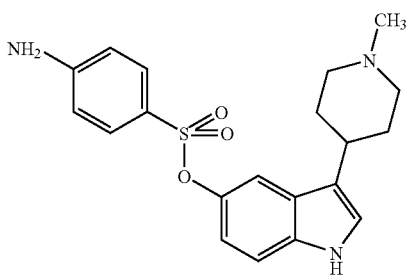

A mixture of 4-nitrobenzenesulfonic acid 3-(1-methylpiperidin-4-yl)-1H-indol-5-yl ester (800 mg, 1.92 mmol) and 5% palladium on carbon (230 mg) in ethanol (100 mL) was hydrogenated at atmospheric pressure at ambient temperature for 1 h. The reaction mixture was filtered and concentrated under reduced pressure. The crude product was purified by flash chromatography (silica gel, 10, 11, 12, 15% 2M ammonia in methanol/methylene chloride) to give 580 mg (78%) of homogeneous product as a yellow oil that crystallized upon standing: mp=$^{217}$-219° C. dec; MS(m/e): 386 (M+1), 384 (M-1); Calculated for $C_{20}H_{23}N_3O_3S$: C, 62.32; H, 6.01; N, 10.90. Found: C, 62.30; H, 5.91; N, 10.69.

EXAMPLE 54

4-Methylsulfonylaminobenzenesulfonic acid 3-(1-methylpiperidin-4-yl)-1H-indol-5-yl ester hydrochloride

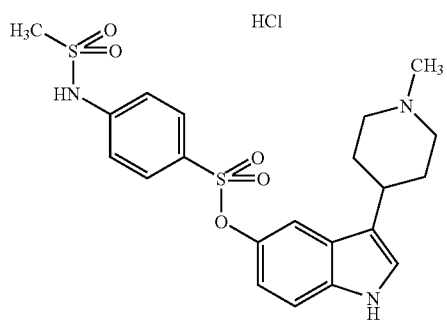

Methylsulfonyl chloride (130 μL, 1.68 mmol) was added dropwise to a solution of 4-aminobenzenesulfonic acid 3-(1-methylpiperidin-4-yl)-1H-indol-5-yl ester (480 mg, 1.25 mmol) and diisopropylethylamine (434 μL, 2.49 mmol) in THF (20 mL) and stirred at ambient temperature for 1 h. The reaction mixture was stored at 5° C. for 18 h. The THF solution was decanted from the yellow glass that had formed. The yellow glass was dissolved in ethyl acetate and water. The ethyl acetate layer contained unreacted starting material and was dried ($Na_2SO_4$), filtered and concentrated under reduced pressure to give 330 mg of 4-aminobenzenesulfonic acid 3-(1-methylpiperidin-4-yl)-1H-indol-5-yl ester. The aqueous layer was basified with 1N NaOH and was extracted with ethyl acetate. The ethyl acetate extracts were dried ($Na_2SO_4$), filtered and concentrated under reduced pressure to give 79 mg of crude product. The crude product was purified by radial chromatography (silica gel, 1000 micron rotor, 5%-20% methanol/1% ammonium hydroxide/methylene chloride) to give 51 mg (8.8%) of homogeneous product as a clear foam. Methylsulfonyl chloride (73 μL, 0.94 mmol) was added to a solution of the recovered 4-aminobenzenesulfonic acid 3-(1-methylpiperidin-4-yl)-1H-indol-5-yl ester (330 mg, 0.86 mmol) and pyridine (76 μL, 0.94 mmol) in methylene chloride (10 mL) and dimethylformamide (2 mL). The reaction mixture was stirred at ambient temperature for 18 h. The reaction mixture was concentrated onto silica gel under reduced pressure and purified by flash chromatography (silica gel, 5%-15% 2M ammonia in methanol/methylene chloride) to give 210 mg of a yellow solid. This product was repurified by radial chromatography (silica gel, 2000 micron rotor, 10% methanol/ 1% ammonium hydroxide/methylene chloride) to give 62 mg (16%) of homogeneous product as a yellow film. Both lots of the product (4-methylsulfonylaminobenzenesulfonic acid 3-(1-methylpiperidin-4-yl)-1H-indol-5-yl ester) were combined and crystallized as the hydrochloric acid salt from ethyl acetate to give 91 mg of the title compound as a white powder: mp=238° C. dec; MS(m/e): 464 (M+1), 462 (M-1); Calculated for $C_{21}H_{25}N_3O_5S_2$·HCl: C, 50.44; H, 5.24; N, 8.40. Found: C, 50.04; H, 5.18; N, 8.19.

EXAMPLE 55

2,6-Difluorobenzenesulfonic acid 7-methyl-3-(1-methylpiperidin-4-yl)-1H-indol-5-yl ester

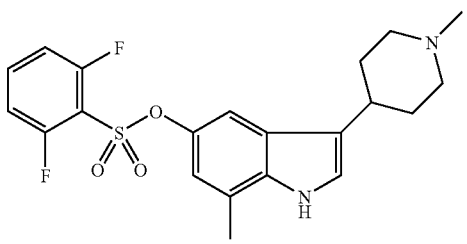

By a method similar to Example 31, using 7-methyl-3-(1-methylpiperidin-4-yl)-1H-indole-5-ol (3.1 mmol, 0.756 g), tetrahydrofuran (10 mL), 0.2N sodium hydroxide (3.1 mmol, 15.5 mL) and 2,6-difluorobenzenesulfonyl chloride (3.7 mmol, 0.7895 g) in tetrahydrofuran (10 mL) afforded the title compound as a fractional salt of 2,6-difluorobenzene sulfonic acid. The material was dissolved in methanol and 5N sodium hydroxide (1 eq) was added. The mixture was then applied to a Mega Bond Elute SCX column. The column was treated with one column volume of the following: methylene chloride, methanol, 3:1 methylene chloride: methanol. The product was eluted with 3:1 methylene chloride: 2M ammonium in methanol. Fractions containing the title compound were concentrated in vacuo to an oil. The oil was dissolved in diethyl ether, then placed in freezer (approximately -4° C.). The resulting crystals were collected by filtration to afford 0.296 g of the title compound. The filtrate was concentrated in vacuo and resubjected to SCX chromatography as described above. An additional 0.313 g of material was collected. A total of 0.609 g (47%) of the title compound was isolated: MS (ion spray): m/z=421(M+1); $^1$H NMR (DMSOd$_6$): 11.04 (s, 1H), 7.90 (m, 1H), 7.40 (m, 2H), 7.16 (1H), 6.88 (1H), 6.69 (1H), 2.78 (m, 2H), 2.54 (m, 1H), 2.39 (s, 3H), 2.19 (s, 3H), 1.94 (m, 2H), 1.65 (m, 2H), 1.51 (m, 2H); Calculated for $C_{21}H_{22}F_2N_2O_3S$: C, 59.99; H, 5.27; N, 6.66. Found: C, 59.96; H, 5.21; N, 6.65.

EXAMPLE 56

2,6-Difluorobenzenesulfonic acid 1,7-dimethyl-3-(1-methylpiperidin-4-yl)-1H-indol-5-yl ester

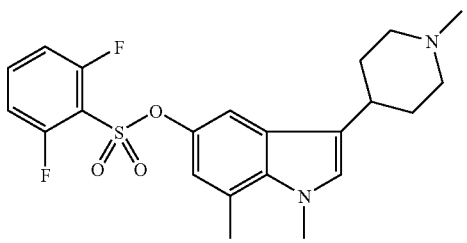

A suspension of 1,7-dimethyl-3-(1-methylpiperdin-4-yl)-5-hydroxy-1H-indole (1.0 eq, 1.98 mmol, 0.511 g) in THF (5.0 mL) at room temperature was added 60% sodium hydride (1.2 eq, 2.37 mmol, 0.095 g). After stirring five minutes 2,6-difluorobenzenesulfonyl chloride (1.1 eq, 2.18 mmol, 0.384 g) was added. The reactions were stirred at room temperature for 3 hours. The reaction was treated with water (25 mL) and 1N sodium hydroxide (2 mL) then extracted with ethyl acetate (2×25 mL). The organic phases were combined, washed with water (25 mL) then brine (25 mL), dried over sodium sulfate, filtered and concentrated in vacuo to an oil. This material was subjected to radial chromatography, 4 mm plate, eluting with 9:1 chloroform: 2M ammonia in methanol. Fractions containing product were combined, concentrated in vacuo to afford an oil. The title compound was crystallized from diethyl ether to afford 0.592 g (59%) of the title compound: mp=139° C.; Mass spectrum (ion spray): m/z=439 (M+1); $^1$H NMR (DMSOd$_6$): 7.95-7.85 (m, 1H), 7.43-7.37 (m, 2H), 7.05 (s, 1H), 6.84 (d, J=2.20 Hz, 1H), 6.64 (d, J=1.46 Hz, 1H), 3.96 (s, 3H), 2.79 (m, 2H), 2.64 (s, 3H), 2.50-2.40 (m, 1H), 2.19 (s, 3H), 1.96 (m, 1H), 1.92 (m, 1H), 1.69-1.56 (m, 2H), 1.53 (m, 1H), 1.44 (m, 1H); Calculated for $C_{22}H_{26}N_2F_2O_3S$: C, 60.89; H, 5.57; N, 6.45. Found: C, 60.67; H, 5.64; N, 6.54.

EXAMPLE 57

2,6-Difluorobenzenesulfonic acid 7-methyl-1-ethyl-3-(1-methylpiperidin-4-yl)-1H-indol-5-yl ester hydrochloride

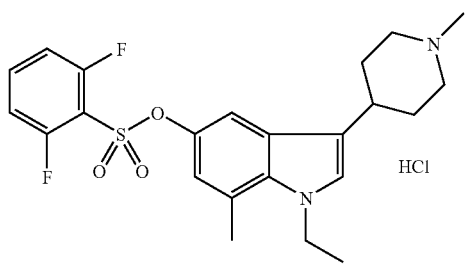

By a method similar to Example 56, using 1-ethyl-7-methyl-3-(1-methylpiperdin-4-yl)-5-hydroxy-1 H-indole (2.22 mmol, 0.605 g), sodium hydride (2.67 mmol, 0.107 g), and 2,6-diflurobenzenesulfonyl chloride (2.44 mmol, 0.519 g) afforded the free amine which was converted to the hydrochloride salt. Acetyl chloride (approximately 1.2 eq) was added to a cooled solution of ethanol (0° C.). After stirring approximately five minutes, this solution was added to a solution of the free amine in diethyl ether. The insoluble material was collected by filtration to afford 0.844 g (78%) of the title compound: MS (ion spray): m/z=449 (M+1); $^1$H NMR (DMSOd$_6$): 7.93-7.87 (m, 1H), 7.46-7.38 (m, 2H), 7.23 (s, 1H), 7.10 (d, J=1.46 Hz, 1H), 6.63 (d, J=1.09 Hz, 1H), 4.30 (q, 2H), 3.47-3.43 (m, 2H), 3.11-3.01 (m, 2H), 2.93-2.79 (m, 1H), 2.76 (s, 3H), 2.59 (s, 3H), 1.96-1.76 (m, 4H), 1.30 (t, J=7.14 Hz, 3H); Calculated for $C_{23}H_{26}F_2N_2O_3S\cdot HCl$: C, 56.96; H, 5.61; N, 5.78. Found: C, 56.97; H, 5.70; N, 5.78.

EXAMPLE 58

2,6-Difluorobenzenesulfonic acid 7-methyl-1-propyl-3-(1-methylpiperidin-4-yl)-1H-indol-5-yl ester hydrochloride

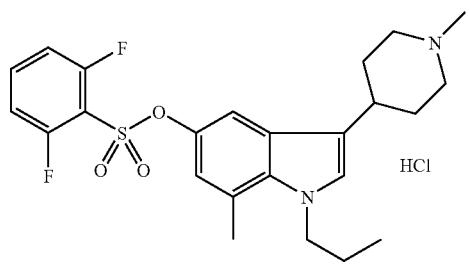

By a method similar to Example 56, using 1-propyl-7-methyl-3-(1-methylpiperdin-4-yl)-5-hydroxy-1H indole (0.619 g), sodium hydride (2.59 mmol, 0.104 g, 60% dispersion in mineral oil), and 2,6-diflurobenzenesulfonyl chloride (2.38 mmol, 0.505 g) afforded 0.589 g (55%) of the free base which was converted to the hydrochloride salt to give the title compound: MS (ion spray): m/z=463 (M+1); $^1$H NMR (DMSOd$_6$): 7.97-7.87 (m, 1H), 7.42 (dd, J=8.78, 3.11 Hz, 2H), 7.22 (s, 1H), 6.63 (s, 1H), 4.22 (t, J=7.32 Hz, 2H), 3.49-3.39 (m, 2H), 3.13-2.93 (m, 2H), 2.90-2.79 (m, 1H), 2.76 (s, 3H), 2.50 (s, 3H), 1.97-1.78 (m, 4H), 1.68 (q, J=14.27, 7.32 Hz, 2H), 0.84 (t, J=7.51 Hz, 3H); Calculated for $C_{24}H_{28}F_2N_2O_3S\cdot HCl$: C, 57.77; H, 5.86; N, 5.61. Found: C, 57.38; H, 5.79; N, 5.58.

EXAMPLE 59

2,6-Difluorobenzenesulfonic acid 1-benzyl-7-methyl-3-(1-methylpiperidin-4-yl)-1H-indol-5-yl ester

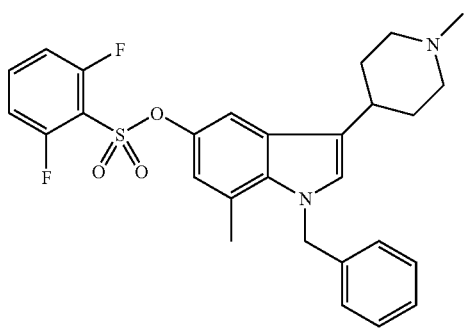

By a method similar to Example 56, using 1-benzyl-7-methyl-3-(1-methylpiperdin-4-yl)-5-hydroxy-1H-indole (1.81 mmol, 0.604 g) in THF (4.5 mL), sodium hydride (2.17 mmol, 0.087 g, 60% dispersion in mineral oil), and 2,6-difluorobenzenesulfonyl chloride (1.99 mmol, 0.422 g) afforded 0.411 g (45%) of the title compound: mp=158° C.; mass spectrum (ion spray): m/z=511 (M+1); $^1$H NMR (DMSOd$_6$): 7.96-7.86 (m, 1H), 7.41 (dd, J=5.73, 3.48 Hz, 2H), 7.31-7.19 (m, 4H), 6.94 (d, J=2.20 Hz, 1H), 6.82 (d, J=6.59 Hz, 2H), 6.62 (d, J=1.87 Hz, 1H), 5.55 (s, 2H), 2.81-2.77 (m, 2H), 2.56-2.42 (m, 1H), 2.36 (s, 3H), 2.20 (s, 3H), 1.96 (m, 2H), 1.72-1.67 (m, 2H), 1.53 (m, 2H);

Calculated for C$_{28}$H$_{28}$F$_2$N$_2$O$_3$S-0.3H$_2$O: C, 65.17; H, 5.59; N, 5.43. Found: C, 65.27; H, 5.47; N, 5.49.

EXAMPLE 60

2,6-Difluorobenzenesulfonic acid 7-methyl-1-phenethyl-3-(1-methylpiperidin-4-yl)-1H-indol-5yl ester hydrochloride

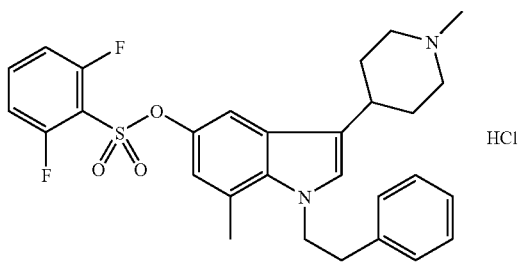

By a method similar to Example 56, using 7-methyl-3-(1-methylpiperdin-4-yl)-1-phenethyl-1H-indol-5-ol (0.55 mmol, 0.190 g) in THF (1.4 mL), sodium hydride (0.65 mmol, 0.026 g, 60% dispersion in mineral oil), and 2,6-diflurobenzenesulfonyl chloride (0.60 mmol, 0.128 g) afforded 0.136 g (44%) of the title compound: MS (ion spray): m/z=511 (M+1); $^1$H NMR (DMSOd$_6$): 7.97-7.87 (m, 1H), 7.45-7.38 (m, 2H), 7.29-7.17 (m, 2H), 7.13 (d, 2H), 6.63 (d, J=1.10 Hz, 1H), 4.53 (t, J=7.50 Hz, 2H), 3.47-3.39 (m, 2H), 3.11-2.95 (m, 4H), 2.87-2.69 (m, 4H), 2.60 (s, 3H), 1.94-1.71 (mm, 4H); Calculated for C$_{28}$H$_{28}$F$_2$N$_2$O$_3$S-1.9 H$_2$O: C, 61.73; H, 5.88; N, 5.14. Found: C, 61.43; H, 5.51; N, 4.93.

EXAMPLE 61

Benzenesulfonic Acid 1,7-dimethyl-3-(1-methylpiperidin-4-yl)-1H-indol-5-yl Ester

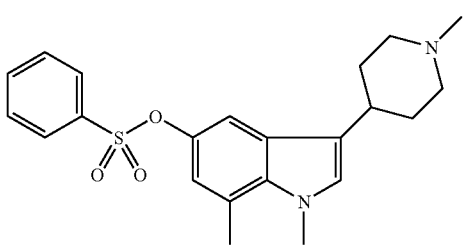

By a method similar to Example 56, using 1,7-dimethyl-3-(1-methylpiperdin-4-yl)-5-hydroxy-1H-indol (1.98 mmol, 0.511 g) in THF (5.0 mL), sodium hydride (2.37 mmol, 0.095 g, 60% dispersion in mineral oil), and benzenesulfonyl chloride (2.18 mmol, 0.384 g), afforded 0.501 g (64%): ms (ion spray): m/z=399 (M+1); $^1$H NMR (DMSOd$_6$): 7.85-7.77 (m, 3H), 7.67-7.62 (m, 2H), 7.01 (s, 1H), 6.64 (d, J=2.56 Hz, 1H), 6.55 (d, J=1.83 Hz, 1H), 3.94 (s, 3H), 2.82-2.72 (bd, 2H), 2.60 (s, 3H), 2.39 (tt, J=3.72 Hz, 1H), 2.18 (s, 3H), 1.91 (m, 2H), 1.67-1.54 (m, 2H), 1.47 (m, 2H); Calculated for C$_{22}$H$_{26}$N$_2$O$_3$S: C, 66.31; H, 6.58; N, 7.03. Found: C, 66.18; H, 6.58; N, 7.08.

EXAMPLE 62

Benzenesulfonic Acid 7-methyl-3-(1-methylpiperidin-4-yl)-1H-indol-5-yl Ester

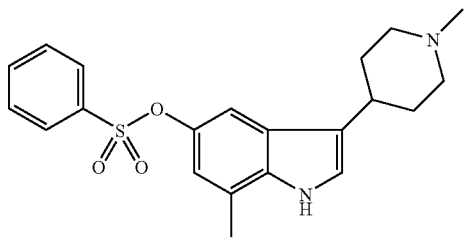

To a suspension of 1-methyl-3-(1-methylpiperdin-4-yl)-5-hydroxy-1H-indole (2.52 mmol, 0.616 g) in THF (6.4 mL) at room temperature was added 60% sodium hydride (3.03 mmol, 0.121 g). After stirring 15 minutes, benzenesulfonyl chloride (2.77 mmol, 0.490 g) was added. Reaction stirred at room temperature for 24 hours. Reaction then treated with ethyl acetate (25 mL) and washed with water (2×25 mL) then brine (25 mL). The organic phase was dried over sodium sulfate, filtered, concentrated in vacuo to afford an oil. The oil was subjected to normal phase radial chromatography, 4 mm plate eluting with 9:1 chloroform:2M ammonia in methanol. Fractions containing product combined, concentrated in vacuo to afford an oil. The oil was dissolved in diethyl ether. The solution was cooled at −4° C. which resulted in crystal formation. Crystals collected by filtration to afford 0.639 g (66%) of the title compound: mp=118° C.; mass spectrum (ion spray): m/z=385 (M); $^1$H NMR (DMSOd$_6$): 7.85-7.77 (m, 3H), 7.67-7.62 (m, 2H), 7.12 (d, J=2.20 Hz, 1H), 6.69 (d, J=2.20 Hz, 1H), 6.60 (d, J=1.46 Hz, 1H), 2.77-2.68 (bd, 2H), 2.43 (m, 1H), 2.37 (s, 3H), 2.19 (s, 3H), 1.92 (m, 2H), 1.71-1.62 (m, 2H), 1.52 (m, 2H); Calculated for C$_{21}$H$_{24}$N$_2$O$_3$S: C, 65.60; H, 6.29; N, 7.29. Found: C, 65.64; H, 6.45; N, 7.19.

EXAMPLE 63

2,6-Dichlorobenzenesulfonic Acid 7-methyl-3-(1-methylpiperidin-4-yl)-1H-indol-5-yl Ester

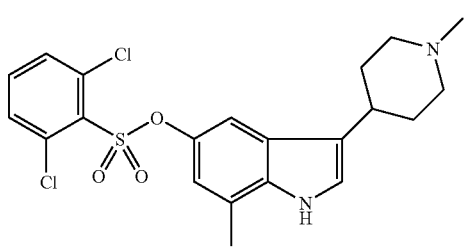

By a method similar to Example 62, using 1-methyl-3-(1-methylpiperdin-4-yl)-5-hydroxy-1H-indole (2.54 mmol, 0.620 g), sodium hydride (3.04 mmol, 0.122 g, 60% dispersion in mineral oil), and 2,6-dichlorobenzenesulfonyl chloride (2.79 mmol, 0.685 g) afforded the title compound which crystallized at room temperature to afford 0.845 g (73%) of the title compound: mp=179° C.; MS (ion spray): m/z=453 (M), 455 (M+2); $^1$H NMR (DMSOd$_6$): 7.77-7.68 (m, 3H), 7.14 (d, J=1.46 Hz, 1H), 6.87 (d, J=1.83 Hz, 1H), 6.70 (d, J=1.10 Hz, 1H), 2.84-2.77 (bd, 2H), 2.50 (m, 1H), 2.38 (s, 3H), 2.20 (s, 3H), 1.95 (m, 2H), 1.72-1.63 (m, 2H), 1.59-1.46 (m, 2H); Calculated for $C_{21}H_{22}ClN_2O_3S$: C, 55.63; H, 4.89; N, 6.18. Found: C, 55.48; H, 4.87; N, 6.12.

EXAMPLE 64

Benzenesulfonic Acid 9-(1-methylpiperidin-4-yl)-2,3-dihydro-1H-pyrrolo[1,2-a]indol-7-yl Ester Hydrochloride

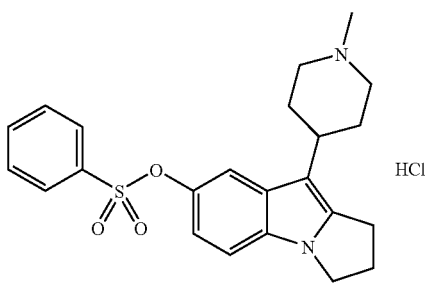

By a method similar to Example 31, using 9-(1-methylpiperidin-4-yl)-2,3-dihydro-1H-pyrrolo[1,2-a]indol-7-ol (135 mg, 0.5 mmol), NaOH (3.25 mL, 0.65 mmol, 0.2 N), benzenesulfonyl chloride (99 mg, 0.564 mmol), and THF (1.5 mL) gave a crude residue which was purified by PCTLC (silica gel GF rotor; 95:5 $CHCl_3$:2M $NH_3$ in MeOH) and the hydrochloride was formed in EtOAc affording 196 mg (88%) of the title compound as an off-white powder: mp=202-204° C.; MS (ES+): m/e 411.0 (M+1); Calculated for $C_{23}H_{26}N_2O_3S \cdot HCl$: C, 61.80; H, 6.09; N, 6.27. Found: C, 61.49; H, 6.10; N, 6.27.

EXAMPLE 65

Benzenesulfonic acid 2-methyl-3-(1-methylpiperidin-4-yl)-1H-indol-5-yl Ester

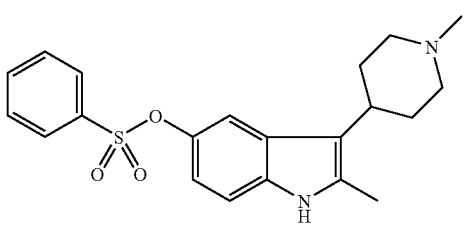

By a method similar to Example 31, using 2-methyl-3-(1-methylpiperidin-4-yl)-5-hydroxy-1H-indole (250 mg, 1.03 mmol), benzenesulfonyl chloride (0.22 g, 1.25 mmol), 0.2N sodium hydroxide and THF (2 mL) gave 96 mg (24%) of the title compound: mass spectrum (ES+)=385.1.

EXAMPLE 66

2,6-Difluorobenzenesulfonic Acid 1-isopropyl-3-(1-methylpiperidin-4-yl)-1H-indol-5-yl Ester Oxalate

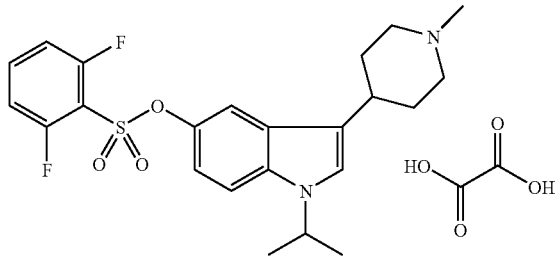

By a method similar to Example 27, using 2,6-Difluorobenzenesulfonic acid 3-(1-methylpiperidin-4-yl)-1H-indol-5-yl ester (400 mg, 0.98 mmol), isopropyl tosylate (2.11 g, 0.8 mmol) and dimethylformamide (20 mL) and sodium hydride (60% dispersion in mineral oil, 43 mg, 1.08 mmol) to afford 54 mg (12%) of the free base of the title compound which was converted to the oxalic salt (58 mg): mp=248-251° C.

EXAMPLE 67

Benzenesulfonic Acid 1-cyclohexyl-3-(1-methylpiperidin-4-yl)-1H-indol-5-yl Ester Oxalate

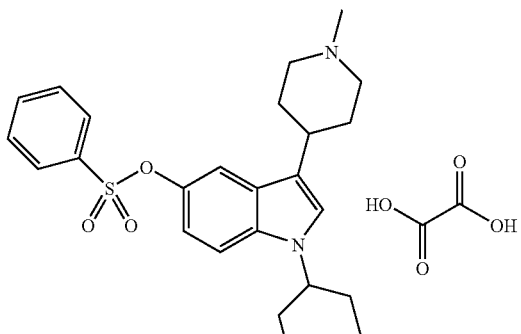

By a method similar to Example 27, using benzenesulfonic acid 3-(1-methylpiperidin-4-yl)-1H-indol-5-yl ester (400 mg, 1.07 mmol), toluene-4-sulfonic acid cyclohexyl ester (2.75 g, 10.7 mmol) and dimethylformamide (20 mL) and sodium hydride (60% dispersion in mineral oil, 47 mg, 1.18 mmol) to afford 189 mg (39%) of the free base of the title compound which was converted to the oxalic salt (110 mg): mp=96-102° C.

EXAMPLE 68

Benzenesulfonic Acid 7-bromo-3-(1-methyl-1,2,3,6-tetrahydropyridin-4-yl)-1H-indol-5-yl Ester

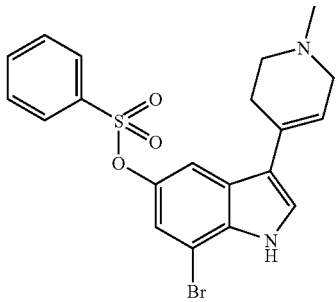

Combine benzenesulfonic acid 7-bromo-1H-indole-5-yl ester and 1-methyl-4-piperidone (4 eq.) in acetic acid. Heat to about 75° C. before adding 2.0 N $H_3PO_4$ (3 eq.). After about 6 hours, cool to room temperature and pour into a mixture of ammonium hydroxide in ice water. Separate the organic layer and dry over $Na_2SO_4$ and concentrated. Purify to give the title compound.

EXAMPLE 69

Benzenesulfonic Acid 7-bromo-3-(1-methylpiperidin-4-yl)-1H-indol-5-yl Ester

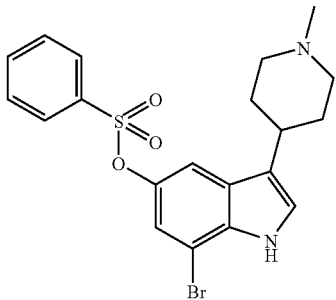

A method similar to Preparation 20, using benzenesulfonic acid 7-bromo-3-(1-methyl-1,2,3,6-tetrahydropyridin-4-yl)-1H-indol-5-yl ester gives the title compound.

EXAMPLE 70

Benzenesulfonic Acid 7-vinyl-3-(1-methylpiperidin-4-yl)-1H-indol-5-yl Ester

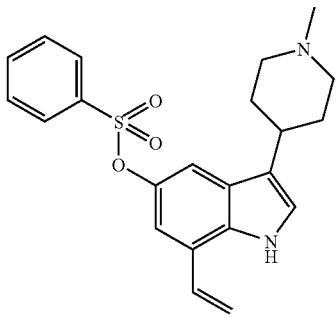

A mixture of benzenesulfonic acid 7-bromo-3-(1-methylpyridin-4-yl)-1H-indol-5-yl ester and Pd $(PPh_3)_4$ (0.2 eq.) in dry toluene was degassed and then treated with vinyl tributyltin (1.1 eq.). Heat the reaction mixture to reflux. After 5 hours, cool to room temperature, pour into ethyl acetate, wash with brine, dry the organic layer over $Na_2SO_4$, and concentrate. Purify to give the title compound.

The compounds of the present invention can be administered alone or in the form of a pharmaceutical composition, that is, combined with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience, solubility, and the like. In practice, the compounds of formula I are usually administered in the form of pharmaceutical compositions, that is, in admixture with pharmaceutically acceptable carriers or diluents.

Thus, the present invention provides pharmaceutical compositions comprising a compound of the formula I and a pharmaceutically acceptable diluent.

The compounds of formula I can be administered by a variety of routes. In effecting treatment of a patient afflicted with disorders described herein, a compound of formula I can be administered in any form or mode which makes the compound bioavailable in an effective amount, including oral and parenteral routes. For example, compounds of formula I can be administered orally, by inhalation, subcutaneously, intramuscularly, intravenously, transdermally, intranasally, rectally, occularly, topically, sublingually, buccally, and the like. Oral administration is generally preferred for treatment of the disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the formula I or its pharmaceutical salt from about 0.1 to about 10% w/v (weight per unit volume).

The compounds of formula I are antagonists of $5\text{-HT}_6$ receptors. Moreover the compounds of formula I are selective antagonists of that particular serotonin receptor. Such antagonism can be identified by the methods below.

EXAMPLE A

Assay Description for $5\text{HT}_6$ Binding

The assay buffer used is 50 mM Tris-HCl pH 7.4, 120 mM NaCl, 5 mM KCl, 5 mM MgCl2, 1 mM EDTA. The radioligand used is $^3$H-LSD from New England Nuclear Cat. # NET 638-75.9 Ci/mmol. The membranes used are from Receptor Biology, Cat. No. RB-HS6. These are membranes from HEK-293 cells expressing the Human $5\text{HT}_6$ receptor.

Test compounds are obtained as 10 mM stocks in 100% DMSO. They are diluted to 1 mM in 100% DMSO by adding 180 μl DMSO to 20 μl of stock in 96 well plates using a multidrop. The 1 mM stocks are then diluted to make an 11 point concentration range from 125 μM down to 1.25 nM in half log increments using 10% DMSO as diluent. This is done using a TECAN robot. The final DMSO at this stage is 21.25%.

Radioligand is diluted in assay buffer to make a 125 nM solution and each vial of membranes is diluted up to 92 mL in assay buffer. The final assay volume is 250 μl consisting of 210 μl of diluted membranes, 20 μl of compound or 21.25% DMSO for total binding, and 20 μl of diluted radioligand. The compounds are transferred from drug dilution plates into corning 96 well assay plates using a 96 well Multimek pipettor. Radioligand and membranes are added to assay plates using multidrop pipettors. Non-specific binding is determined in wells containing a final serotonin concentration of 10 μM. In the final assay volume the radioligand is 10 nM and the membrane protein is approximately 25 μg/well. The final drug concentration range in half logs is from 10 μM down to 0.1 nM. The final DMSO in the assay is 1.7%.

After addition of drug, membrane, and ligand, the plates are incubated for one hour at room temperature. During this time 96 well Millipore filter plates (MAFBNOB50) are soaked for a least 30 minutes with 200 μl per well of 0.5% polyethyleneimine.

The 0.5% PEI is removed from filterplate wells using a TiterTek MAP aspirator and 200 μl of the incubation mixture is transferred from the incubation plate to the filterplate after mixing. This transfer is done using the 96 tip Mutimek pipettor. After transfer to the filterplate filterplates are extracted and washed twice with 220 μl per well of cold buffer on the MAP aspirator. The peel away bottoms are removed from the filterplates and 100 μl per well of microscint 20 scintillation fluid is added per well using a multidrop. Plates are placed into suitable holders and are left at room temperature for three hours and are counted for $^3$H in either a Wallac Microbeta counter or on a Packard Topcount.

In one embodiment, the present invention provides methods of treating disorders associated with the $5\text{-HT}_6$ receptor, comprising: administering to a patient in need thereof an effective amount of a compound of formula I. Thus, the present invention contemplates the various disorders described to be treated herein and others which can be treated by such antagonists as are appreciated by those skilled in the art.

In particular, because of their ability to antagonize the $5\text{-HT}_6$ receptor, it is recognized that the compounds of the present invention are useful for treating cognitive disorders, that is, disorders involving cognitive deficits. A number of the disorders which can be treated by $5\text{-HT}_6$ antagonists are known according to established and accepted classifications, while others are not.

Some of the disorders to be treated according to the present invention are not well categorized and classified because cognition is a complicated and sometimes poorly defined phenomenon. It is, however, widely recognized that cognition includes various "domains." These domains include short term memory, long term memory, working memory, executive function, and attention.

While many of the disorders which can be treated according to the present invention are not uniformly described and classified in the art, it is understood that the compounds of the present invention are useful for treatment of disorders characterized by a deficit in any of the cognitive domains listed above or in other aspects of cognition. Thus the term "cognitive disorders" is meant to encompass any disorder characterized by a deficit in one or more cognitive domain, including but not limited to short term memory, long term memory, working memory, executive function, and attention.

One cognitive disorder to be treated by the present invention is age-related cognitive decline. This disorder is not well defined, but includes decline in the cognitive domains, particularly the memory and attention domains, which accompany aging. Another is mild cognitive impairment. Again, this disorder is not well defined in the art, but involves decline in the cognitive domains, and is believed to represent a group of patients the majority of which have incipient Alzheimer's disease. Also, a wide variety of insults, including stroke, ischemia, hypoxia, inflammation, and infectious processes can result in cognitive deficits as a sequella which can be treated according to the present invention.

Where the disorders which can be treated by $5\text{-}HT_6$ antagonists are known according to established and accepted classifications, these classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision, (ICD-10) provides classifications for many of the disorders described herein. The skilled artisan will recognize that there are alternative nomenclatures, nosologies, and classification systems for disorders described herein, including those as described in the DMS-IV and ICD-10, and that terminology and classification systems evolve with medical scientific progress.

In one embodiment, the present invention provides methods of treating disorders selected from the group consisting of: age-related cognitive disorder, mild cognitive impairment, mood disorders (including depression, mania, bipolar disorders), psychosis (in particular schizophrenia), anxiety (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, and hypoglycemic neuronal damage, vascular dementia, multi-infarct dementia, amylotrophic lateral sclerosis, and multiple sclerosis, comprising: administering to a patient in need thereof an effective amount of a compound of formula I. That is, the present invention provides for the use of a compound of formula I or pharmaceutical composition thereof for the treatment disorders associated with the $5\text{-}HT_6$ receptor.

It is recognized that the terms "treatment" and "treating" are intended to include improvement of the cognitive deficit associated with each of the disorders associated with the $5\text{-}HT_6$ receptor described herein. Also, it is also recognized that one skilled in the art may affect the disorders by treating a patient presently afflicted with the disorders or by prophylactically treating a patient believed to be susceptible to such disorders with an effective amount of the compound of formula I. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms, and is intended to include prophylactic treatment of such disorders. For example, the present invention specifically encompasses the treatment of the cognitive deficits associated with schizophrenia, stroke, Alzheimer's disease, and the other disorders described herein. Thus, it is understood that the present invention includes adjunctive treatment of the disorders described herein. More specifically, the compounds of formula I are useful to treat schizophrenia in combination with typical and atypical antipsychotics; to treat stroke in combination with a variety of agents such as mGluR agonists, NMDA antagonists, IL 1-6 inhibitors, and the like; to treat Alzheimer's disease in combination with cholinergics, including cholinesterase inhibitors, and compounds that inhibit amyloid protein processing.

As used herein, the term "patient" refers to a warm blooded animal such as a mammal which is afflicted with one or more disorders associated with the $5\text{-}HT_6$ receptor. It is understood that guinea pigs, dogs, cats, rats, mice, horses, cattle, sheep, pigs, and humans are examples of animals within the scope of the meaning of the term. It is also understood that this invention relates specifically to the antagonists of the $5\text{-}HT_6$ receptor.

As used herein, the term "effective amount" of a compound of formula I refers to an amount, that is, the dosage which is effective in treating the disorders described herein.

An effective amount can be readily determined by the attending diagnostician, as one skilled in the art, by the use of conventional techniques and by observing results obtained under analogous circumstances. In determining an effective amount, the dose of a compound of formula I, a number of factors are considered by the attending diagnostician, including, but not limited to: the compound of formula I to be administered; the co-administration of other therapies, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of formula I is expected to vary from about 0.1 milligram per kilogram of body weight per day (mg/kg/day) to about 100 mg/kg/day. Preferred amounts are able to be determined by one skilled in the art.

Of the disorders to be treated according to the present invention a number are particularly preferred.

In a preferred embodiment the present invention provides a method of treating cognitive disorders, comprising: administering to a patient in need thereof an effective amount of a compound of claim 1.

In another preferred embodiment the present invention provides a method for treating Alzheimer's disease, comprising: administering to a patient in need thereof an effective amount of a compound of formula I.

In a preferred embodiment the present invention provides a method for treating schizophrenia, comprising: administering to a patient in need thereof an effective amount of a compound of formula I.

The fourth edition of the Diagnostic and Statistical Manual of Mental Disorders (DSM-IV™) (1994, American Psychiatric Association, Washington, D.C.), provides a diagnostic tool including schizophrenia and related disorders.

In a preferred embodiment the present invention provides a method for treating migraine, comprising: administering to a patient in need thereof an effective amount of a compound of formula I or a pharmaceutical composition thereof.

In one of the available sources of diagnostic tools, *Dorland's Medical Dictionary* (23$^{rd}$ Ed., 1982, W. B. Saunders Company, Philidelphia, Pa.), migraine is defined as a symptom complex of periodic headaches, usually temporal and unilateral, often with irritability, nausea, vomiting, constipation or diarrhea, and photophobia. As used herein the term "migraine" includes to these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In a preferred embodiment the present invention provides a method for treating anxiety disorders, including generalized anxiety disorder, panic disorder, and obsessive compulsive disorder, comprising: administering to a patient in need thereof an effective amount of a compound of formula I.

At present, the fourth edition of the Diagnostic and Statistical Manual of Mental Disorders (DSM-IV™) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

A number of preclinical laboratory animal models have been described for the disorders described herein.

EXAMPLE B

Animal Model of Dural Protein Extravasation

Harlan Sprague-Dawley rats (250-350 g) were anesthetized with sodium pentobarbital intraperitoneally (65 mg/kg) and placed in a stereotaxic frame (David Kopf Instruments) with the incisor bar set at −3.5 mm. Following a midline sagital scalp incision, two pairs of bilateral holes were drilled through the skull (6 mm posteriorly, 2.0 and 4.0 mm laterally, all coordinates referenced to bregma). Pairs of stainless steel stimulating electrodes, insulated except at the tips (Rhodes Medical Systems, Inc.), were lowered through the holes in both hemispheres to a depth of 9 mm.

The femoral vein was exposed and a dose of the test compound was injected intravenously (i.v.) at a dosing volume of 1 mL/kg or, in the alternative, test compound was administered orally (p.o.) via gavage at a volume of 2 mL/kg. Approximately 8 minutes post i.v. injection, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 40 mL of saline. The top of the skull was removed to facilitate the collection of the dural membranes. The membrane samples were removed from both hemispheres, rinsed with water, and spread flat on microscopic slides. Once dried, the tissues were coverslipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 mm steps) on each dural sample. The mean and standard deviation of the measurements were determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side, over the amount of extravasation in the unstimulated side, was calculated. Control animals dosed only with saline, yielded a ratio of approximately 1.9. In contrast, a compound which effectively prevented the extravasation in the dura from the stimulated side would yield a ratio of approximately 1.0.

The fear potentiated startle response model has been extensively used as a model of anxiety and can be used to evaluate the present compounds. Davis, *Psychopharmacol.*, 62: 1 (1979); Davis, *Behav. Neurosci.*, 100: 814 (1986); Davis, *Tr. Pharmacol. Sci.*, 13: 35 (1992).

EXAMPLE C

Fear Potentiated Startle Paradigm

Male Sprague-Dawley rats weighing 325-400 g were purchased from Harlan Sprague-Dawley, Inc. (Cumberland, Ind.) and given a one week acclimation period before testing. Rats were individually housed with food and water ad libitum in an animal room on a 12-hour light/dark cycle with lights on between 6:00 A.M. and 6:00 P.M. The compound of Example 16 was prepared in a suspension of 5% ethanol, 0.5% CMC, 0.5% Tween 80 and 99% water. 2S-2-amino-2-(1S,2S-2-carboxycyclopropan-1-yl)-3-(xanth-9-yl) propionic acid was prepared in sterile water. Control rats were given the respective vehicle.

The fear potentiated startle paradigm is conducted over three consecutive days. All three days begin with a 5-minute adaptation period before the trial starts. On day one (baseline startle) after the adaptation period, the animal receives 30 trials of 120 dB auditory noise. The mean startle amplitude ($V_{max}$) is used to assign animals to groups with similar means before conditioning begins. Day two consists of conditioning the animals. Each animal receives 0.5 mA of shock for 500 msec preceded by a 5 second presentation of light which remains on for the duration of the shock. Ten presentations of the light and shock are administered. Day three is the testing trial where drug administration occurs prior to testing. Twenty-four hours after conditioning, startle testing sessions are conducted. Ten trials of acoustic startle (120 dB), non-light paired, are presented at the beginning of the session. This is followed by 20 random trials of the noise alone and 20 random trials of noise preceded by light. Excluding the first 10 trials, the startle response amplitudes for each trial type are averaged for each animal. Data is presented as the difference between light+noise and noise-alone. Differences in startle response amplitudes were analyzed by JMP statistical software using a One-way Anova (analysis of variance, t-test). Group differences were considered to be significant at p<0.05.

The radial arm maze model can be used as a model of cognition and can be used to evaluate the present compounds.

EXAMPLE D

Radial Arm Maze

The delayed non-match to sample task has been used to study the effect of drugs on memory retention (Pussinen, R. and Sirvio, J. *J of Psychopharm* 13: 171-179 (1999); Staubli, U., et al. *Proc Natl Acad Sci* 91: 777-781 (1994)) in the eight arm radial maze.

Well-trained rats were allowed to retrieve food rewards from four randomly selected arms of the maze (sampling phase). Some time later, the rats were exposed to eight open arms and were tested for their ability to remember and avoid the arms they had previously entered to obtain food. Re-entry into an arm that was baited during the sampling session was counted as a reference error, whereas entry into the same arm more than once during the retention session was counted as working error. The total (reference+working) number of errors made during the retention test increases with increasing delay periods. For example, young male rats made 0.66 (+0.4) errors at a 1 minute delay, 2 (+0.5) errors at a one hour delay, and 3.95 (+0.2) errors at a seven hour delay (observations of this lab).

Male Sprague-Dawley rats were individually housed and maintained on a 12 h light-dark cycle (lights on at 6 am). The rats were given free access to water and maintained at 85% of their free-feeding weight by supplemental feedings of Purina Lab Chow.

The rats were initially trained to search for food at the end of each of the eight arms. Once the rats had reached the criteria of no more than two errors (i.e. entering the same arm more than once during a session) on three consecutive days, a delay of one minute was imposed between the fourth and the fifth arm choices. This training ensured that the rats were thoroughly familiar with the procedural aspects of the task before any drugs were administered. Once stable performance had been obtained on the delay task (i.e. no more than one error was made on three consecutive days), drug and vehicle tests commenced using a seven hour delay period. A novel set of arms was baited each day for each rat and the maze was thoroughly cleaned during the delay period.

During the sampling session, each rat was placed on the center platform with access to all eight arms of the maze blocked. Four of the eight arms were randomly selected and baited with food. The gates of the baited arms were raised and the rat was allowed five minutes to obtain the food at the end of each of the four arms. As soon as the rat had obtained the food, it was removed, administered vehicle or various doses of compounds, and placed back in its home cage. Seven hours later (retention session), the rat was placed back onto the center platform with access to all eight arms blocked. The four arms that were previously baited during the sampling session, were baited and the gates to all eight arms were raised. The rat was allowed five minutes to obtain the remaining four pieces of food. An entry into a non-baited arm or a re-entry into a previously visited arm was counted as an error. Significance (p<0.05) was determined using a repeated measure ANOVA followed by a Dunnett's test for comparison with control.

In order to compare test compounds with standards, scopolamine and tacrine were administered s.c. immediately after the sampling phase. The effects of scopolamine, a known amnesic, were tested after a three-hour delay, whereas the effect of tacrine, a cholinesterase inhibitor used in the treatment of Alzheimer's disease was tested after a six-hour delay. Scopolamine disrupted retention after a three-hour delay in a dose-related fashion. Tacrine significantly improved retention after a six-hour delay at 10, but not at 3 mg/kg.

EXAMPLE E

Acquisition in the Radial Maze 8-arm Radial Maze Acquisition

A prominent early feature of Alzheimer's disease (AD) symptomology is a pronounced deficit in declarative memory (R. W. Parks, R. F. Zec & R. S. Wilson (Eds.), *Neuropsychology of Alzheimer's disease and other dementias*. NY: Oxford University Press pp. 3-80 (1993).

As the disease progresses, other domains of cognition become severely affected as well. Among the brain regions affected early in the progression of AD is the hippocampus, which is a critical neural substrate for declarative memory (West M. J., Coleman P. D., Flood D. G. & Troncoso J. C.. Differences in the pattern of hippocampal neuronal loss in normal aging and Alzheimer's disease. *Lancet*, 344: 769-772(1994). One behavioral test that is often used to assess hippocampal function in animal models is the 8-arm radial maze (Olton D. S. The radial arm maze as a tool in behavioral pharmacology. Physiology & Behavior, 40: 793-797 (1986)).

Lesions or pharmacological blockade of the hippocampus disrupt performance of this task. Moreover, aged animals generally show deficits in this task (Porsolt R. D., Roux S. & Wettstein J. G. Animal models of dementia. Drug Development Research, 35: 214-229(1995)).

In this test of spatial learning and memory, a hungry rat is placed in the center of the maze and allowed to traverse the maze in search of food located at the end of each runway arm. In this version of the maze, the rat learns a win-shift strategy in, which a visited arm is not replaced. Therefore, the most efficient foraging strategy is to visit each arm once. The version of the maze also taps into general learning processes as the rat is naive to the maze on day one of the four day experiment.

Upon arrival, male Sprague Dawley®, rats were individually housed in a regular light-cycle colony room and allowed to acclimate for at least 4 days prior to testing. Each rat was reduced to and maintained at 85% of their target body weight throughout the experiment. Proper body weight was maintained by adjusting the allotment of lab chow based on a combination of age and the rat's daily bodyweight reading.

A session began with an individual rat being placed into the hub of the maze and then all guillotine doors were raised, allowing free access to all areas of the maze. A food hopper was located at the end of each of the 8 runway arms and a single food pellet was placed in each food hopper. Each daily session terminated when either all 8 food-hoppers had been visited or when the rat timed out (15 min on Day 1: 5 min on Days 2-4). The number of arm entries was recorded. Errors were counted as repeat arm entries or failures to visit an arm in the session period. An animal was excluded from the study if it failed to visit at least one arm on Day 1, 2 arms on Day 2, and at least 4 arms on Days 3 & 4.

Each rat was pseudo-randomly assigned to either a vehicle or drug group and received the same treatment throughout the experimental period. Vehicle consisted of 5% acacia within sterile water. Injections were administered subcutaneously 20-30 minutes prior to each daily session.

In this acquisition task, vehicle-treated animals do not consistently show significant acquisition of maze learning as compared to the number of errors committed on Day 1. We have found that in compounds that facilitate acquisition of maze learning, the effects are often not observed until the fourth day of training. Therefore, results consisted of total Day 4 errors across treatment groups.

What is claimed is:

1. A compound of the formula

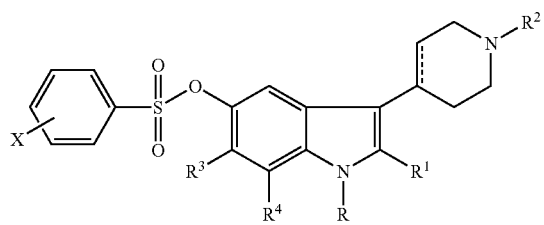

wherein
R is hydrogen, $C_1$-$C_6$ alkyl, or $C_3$-$C_6$ cycloalkyl;
which $C_1$-$C_6$ alkyl is unsubstituted or is substituted with 1 or 2 substituents selected from the group consisting of $C_3$-$C_6$ cycloalkyl, phenyl, substituted phenyl, pyridyl, and trifluoromethyl;
which phenyl is unsubstituted or is substituted with 1 to 3 groups independently selected from the group consisting of hydrogen, $C_1$-$C_6$ alkyl, $C_1$-$C_6$ alkoxy, halogen, cyano, trifluoromethyl, nitro, and phenyl;
$R^1$ is hydrogen or $C_1$-$C_3$ alkyl
$R^2$ is hydrogen or $C_1$-$C_6$ alkyl;
$R^3$ is hydrogen or halo;
$R^4$ is hydrogen, $C_1$-$C_6$ alkyl, vinyl, allyl, $C_2$-$C_6$ alkynyl, or halo;
X is 1 to 3 substituents independently selected from the group consisting of hydrogen, halo, $C_1$-$C_6$ alkyl, $C_1$-$C_6$ alkoxy, nitro, amino, $C_1$-$C_6$ alkylsulfonylamino, and cyano, or X is 5 halo substituents;

represents either a single or a double bond;
or a pharmaceutically acceptable addition salt thereof.

2. A compound according to claim 1 wherein R is hydrogen, or $C_1$-$C_6$ alkyl;
which $C_1$-$C_6$ alkyl is unsubstituted or is substituted with 1 or 2 substituents selected from the group consisting of $C_3$-$C_6$ cycloalkyl, phenyl, substituted phenyl, pyridyl, and trifluoromethyl.

3. A compound according to claim 2 wherein R is hydrogen or $C_1$-$C_6$ alkyl.

4. A compound according to claim 3 wherein $R^2$ is $C_1$-$C_6$ alkyl.

5. A compound according to claim 4 wherein $R^2$ is methyl.

6. A compound according to claim 5 wherein X is halo.

7. A compound according to claim 6 wherein X is fluoro.

8. A compound according to claim 7 wherein X is 2,6-difluoro.

9. A pharmaceutical composition comprising a compound of claim 1 and a pharmaceutically acceptable diluent.

10. The compound 2,6-Difluorobenzenesulfonic acid 1-methyl-3-(1-methylpiperidin-4-yl)-1H-indol-5-yl ester, or a pharmaceutically acceptable salt thereof.

11. The compound of claim 10 which is 2,6-Difluorobenzenesulfonic acid 1-methyl-3-(1-methylpiperidin-4-yl)-1H-indol-5-yl ester mesylate.

* * * * *